US008778990B2

(12) United States Patent
Honda et al.

(10) Patent No.: US 8,778,990 B2
(45) Date of Patent: Jul. 15, 2014

(54) BETULINIC ACID DERIVATIVES AND METHODS OF USE THEREOF

(75) Inventors: Tadashi Honda, Port Jefferson Station, NY (US); Michael B. Sporn, Tunbridge, VT (US); Karen T. Liby, West Lebanon, NH (US); Gordon W. Gribble, Lebanon, NH (US); Robert M. Kral, Jr., Grapevine, TX (US); Melean Visnick, Irving, TX (US)

(73) Assignees: Trustees of Dartmouth College, Hanover, NH (US); Reata Pharmaceuticals, Inc., Irving, TX (US)

( * ) Notice: Subject to any disclaimer, the term of this patent is extended or adjusted under 35 U.S.C. 154(b) by 286 days.

(21) Appl. No.: 13/127,551

(22) PCT Filed: Oct. 29, 2009

(86) PCT No.: PCT/US2009/062456
§ 371 (c)(1),
(2), (4) Date: Jul. 19, 2011

(87) PCT Pub. No.: WO2010/053817
PCT Pub. Date: May 14, 2010

(65) Prior Publication Data
US 2012/0101149 A1 Apr. 26, 2012

Related U.S. Application Data

(60) Provisional application No. 61/111,274, filed on Nov. 4, 2008.

(51) Int. Cl.
*A61K 31/277* (2006.01)
*A61K 48/00* (2006.01)
*A61N 5/00* (2006.01)
*A61P 35/00* (2006.01)

(52) U.S. Cl.
USPC ............ 514/510; 558/429; 560/120; 560/252

(58) Field of Classification Search
USPC .......................... 552/510; 560/120, 253, 252
See application file for complete search history.

(56) References Cited

U.S. PATENT DOCUMENTS

| 6,303,589 | B1 * | 10/2001 | Glinski et al. | 514/169 |
| 6,369,101 | B1 * | 4/2002 | Carlson | 514/468 |
| 6,433,010 | B2 * | 8/2002 | Glinski et al. | 514/510 |
| 6,458,834 | B2 * | 10/2002 | Glinski et al. | 514/510 |
| 2007/0232577 | A1 * | 10/2007 | Xu et al. | 514/169 |
| 2009/0060873 | A1 | 3/2009 | Sporn et al. | 424/85.6 |

FOREIGN PATENT DOCUMENTS

WO    WO 2007/112043    * 10/2007

OTHER PUBLICATIONS

Honda, Tadashi et al. (DN 146:142851, HCAPLUS, abstract of Bioorganic & Medicinal Chemistry Letters (2006), 16(24), 6306-6309.*
Evers, Michael et al. (DN 124:146499, AN 1996:95598, HCAPLUS, abstract of Journal of Medicinal Chemistry (1996), 39(5), 1056-68).*
Honda et al. "Design, Synthesis, and Anti-inflammatory Activity Both in vitro and in vivo of New Betulinic Acid Analogues Having an Enone Functionality in Ring A" Bioorganic & Medicinal Chemistry Letters 2006 16(24):6306-6309.
Liby et al. "Novel Semisynthetic Analogues of Betulinic Acid with Diverse Cytoprotective, Antiproliferative, and Proapoptotic Activities" Molecular Cancer Therapeutics 2007 6(7):2113-2119.
Pisha et al. "Discovery of Betulinic Acid as a Selective Inhibitor of Human Melanoma that Functions by Induction of Apoptosis" Nature Medicine 1995 1(10):1046-1051.
Schmidt et al. "Betulinic Acid Induces Apoptosis in Human Neuroblastoma Cell Lines" European Journal of Cancer 1997 33(12):2007-2010.
You et al. "Synthesis and Cytotoxic Activity of A-ring Modified Betulinic Acid Derivatives" Bioorganic & Medicinal Chemistry Letters 2003 13(19):3137-3140.
Zuco et al. "Selective Cytotoxicity of Betulinic Acid on Tumor Cell Lines, but Not on Normal Cells" Cancer Letters 2002 175:17-25.

* cited by examiner

Primary Examiner — Sabiha N Qazi
(74) Attorney, Agent, or Firm — Licata & Tyrrell P.C.

(57) ABSTRACT

This invention features betulinic acid derivatives having the formula: wherein the variables are defined herein. The invention also provides related compounds and intermediates thereof, as well as pharmaceutical compositions, kits, and articles of manufacture comprising such compounds. Treatment methods and methods of manufacture are also provided.

5 Claims, 3 Drawing Sheets

BETULINIC ACID DERIVATIVES AND METHODS OF USE THEREOF

INTRODUCTION

This application is the national phase under 35 U.S.C. §371 of PCT International Application No. PCT/US2009/062456, filed Oct. 29, 2009, which claims benefit of U.S. Provisional Patent Application Ser. No. 61/111,274 filed Nov. 4, 2008, the content of which is incorporated herein by reference in its entirety.

BACKGROUND OF THE INVENTION

Many serious and intractable human diseases are associated with dysregulation of inflammatory processes, including diseases such as cancer, atherosclerosis, and diabetes, which were not traditionally viewed as inflammatory conditions. Similarly, autoimmune diseases such as rheumatoid arthritis, lupus, psoriasis, and multiple sclerosis involve inappropriate and chronic activation of inflammatory processes in affected tissues, arising from dysfunction of self vs. non-self recognition and response mechanisms in the immune system. In neurodegenerative diseases such as Alzheimer's and Parkinson's diseases, neural damage is correlated with activation of microglia and elevated levels of pro-inflammatory proteins such as inducible nitric oxide synthase (iNOS).

One aspect of inflammation is the production of inflammatory prostaglandins such as prostaglandin E, whose precursors are produced by the enzyme cyclo-oxygenase (COX-2). High levels of COX-2 are found in inflamed tissues. Consequently, inhibition of COX-2 is known to reduce many symptoms of inflammation and a number of important anti-inflammatory drugs (e.g., ibuprofen and celecoxib) act by inhibiting COX-2 activity. Recent research, however, has demonstrated that a class of cyclopentenone prostaglandins (e.g., 15-deoxy prostaglandin J2, a.k.a. PGJ2) plays a role in stimulating the orchestrated resolution of inflammation. COX-2 is also associated with the production of cyclopentenone prostaglandins. Consequently, inhibition of COX-2 may interfere with the full resolution of inflammation, potentially promoting the persistence of activated immune cells in tissues and leading to chronic, "smoldering" inflammation. This effect may be responsible for the increased incidence of cardiovascular disease in patients using selective COX-2 inhibitors for long periods of time. Corticosteroids, another important class of anti-inflammatory drugs, have many undesirable side effects and frequently are not suitable for chronic use. Newer protein-based drugs, such as anti-TNF monoclonal antibodies, have proven to be effective for the treatment of certain autoimmune diseases such as rheumatoid arthritis. However, these compounds must be administered by injection, are not effective in all patients, and may have severe side effects. In many severe forms of inflammation (e.g., sepsis, acute pancreatitis), existing drugs are ineffective. In addition, currently available drugs do not have significant antioxidant properties, and are not effective in reducing oxidative stress associated with excessive production of reactive oxygen species and related molecules such as peroxynitrite. Accordingly, there is a need for improved therapeutics with antioxidant and anti-inflammatory properties.

Betulinic acid (BA) is a pentacyclic lupane-type triterpene isolated from various plants. Both in vitro and in vivo results are consistent with low potency anti-cancer activity (Pisha, et al. (1995) *Nat. Med.* 1:1046; Schmidt, et al. (1997) *Eur. J. Cancer* 33:2007; Zuco et al. (2002) *Cancer Lett.* 175:17). Attempts have been made to improve the anti-inflammatory and anti-proliferative properties of betulinic acid (You, et al. (2003) *Bioorg. Med. Chem. Lett.* 13(19):3137-3140; Honda, et al. (2006) *Bioorg. Med. Chem. Lett.* 16(24):6306-9; Liby, et al. (2007) *Mol. Cancer Ther.* 6(7):2113-9), however, there are no approved drugs based on the betulinic acid or a derivative thereof. Accordingly, there is a need for further improved betulinic acid derivatives.

SUMMARY OF THE INVENTION

The present invention provides compounds with antioxidant and anti-inflammatory properties, methods for their manufacture, and methods for their use. Compounds covered by the generic or specific formulas below or specifically named are referred to as "compounds of the invention," "compounds of the present invention," or "betulinic acid derivatives" in the present application.

In one embodiment, the present invention features a compound of the formula:

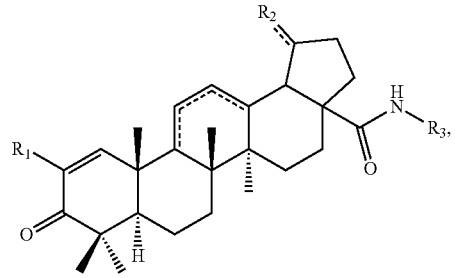

wherein:

$R_1$ is cyano, halo, hydroxy, alkoxy$_{(C\leq 8)}$, substituted alkoxy$_{(C\leq 8)}$, acyl$_{(C\leq 8)}$, or substituted acyl$_{(C\leq 8)}$;

$R_2$ is hydrogen, cyano, hydroxy, halo, amino or oxo; or alkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heteroaralkyl$_{(C\leq 12)}$, acyl$_{(C\leq 12)}$, alkylidene$_{(C\leq 12)}$, alkoxy$_{(C\leq 12)}$, alkenyloxy$_{(C\leq 12)}$, alkynyloxy$_{(C\leq 12)}$, aryloxy$_{(C\leq 12)}$, aralkoxy$_{(C\leq 12)}$, heteroaryloxy$_{(C\leq 12)}$, heteroaralkoxy$_{(C\leq 12)}$, acyloxy$_{(C\leq 12)}$, alkylamino$_{(C\leq 12)}$, dialkylamino$_{(C\leq 12)}$, alkoxyamino$_{(C\leq 12)}$, alkenylamino$_{(C\leq 12)}$, alkynylamino$_{(C\leq 12)}$, arylamino$_{(C\leq 12)}$, aralkylamino$_{(C\leq 12)}$, heteroarylamino$_{(C\leq 12)}$, heteroaralkylamino$_{(C\leq 12)}$, alkylsulfonylamino$_{(C\leq 12)}$, amido$_{(C\leq 12)}$, alkylimino$_{(C\leq 12)}$, alkenylimino$_{(C\leq 12)}$, alkynylimino$_{(C\leq 12)}$, arylimino$_{(C\leq 12)}$, aralkylimino$_{(C\leq 12)}$, heteroarylimino$_{(C\leq 12)}$, heteroaralkylimino$_{(C\leq 12)}$, acylimino$_{(C\leq 12)}$, alkylthio$_{(C\leq 8)}$, alkenylthio$_{(C\leq 12)}$, alkynylthio$_{(C\leq 12)}$, arylthio$_{(C\leq 12)}$, aralkylthio$_{(C\leq 12)}$, heteroarylthio$_{(C\leq 12)}$, heteroaralkylthio$_{(C\leq 12)}$, acyl-thio$_{(C\leq 12)}$, thioacyl$_{(C\leq 12)}$, alkylsulfonyl$_{(C\leq 12)}$, alkenylsulfonyl$_{(C\leq 12)}$, alkynylsulfonyl$_{(C\leq 12)}$, arylsulfonyl$_{(C\leq 12)}$, aralkylsulfonyl$_{(C\leq 12)}$, heteroarylsulfonyl$_{(C\leq 12)}$, heteroaralkylsulfonyl$_{(C\leq 12)}$, alkylammonium$_{(C\leq 12)}$, alkylsulfonium$_{(C\leq 12)}$, or alkylsilyl$_{(C\leq 12)}$, or a substituted version of any of these groups; and $R_3$ is a substituted alkyl$_{(C\leq 8)}$; or pharmaceutically acceptable salts, hydrates, solvates, tautomers, prodrugs, or optical isomers thereof.

In another embodiment, the present invention features a compound of the formula:

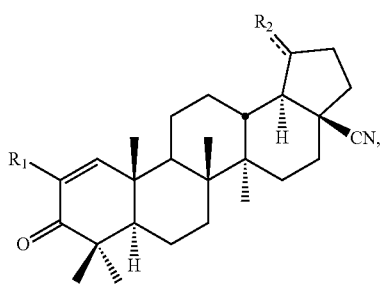

wherein:

R₁ is cyano, halo, hydroxy, alkoxy$_{(C≤8)}$, substituted alkoxy$_{(C≤8)}$, acyl$_{(C≤8)}$, or substituted acyl$_{(C≤8)}$; and R₂ is hydrogen, cyano, hydroxy, halo, amino, alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, acyl$_{(C≤12)}$, alkylidene$_{(C≤12)}$, alkoxy$_{(C≤12)}$, alkenyloxy$_{(C≤12)}$, alkynyloxy$_{(C≤12)}$, aryloxy$_{(C≤12)}$, aralkoxy$_{(C≤12)}$, heteroaryloxy$_{(C≤12)}$, heteroaralkoxy$_{(C≤12)}$, acyloxy$_{(C≤12)}$, alkylamino$_{(C≤12)}$, dialkylamino$_{(C≤12)}$, alkoxyamino$_{(C≤12)}$, alkenylamino$_{(C≤12)}$, alkynylamino$_{(C≤12)}$, arylamino$_{(C≤12)}$, aralkylamino$_{(C≤12)}$, heteroarylamino$_{(C≤12)}$, heteroaralkylamino$_{(C≤12)}$, alkylsulfonylamino$_{(C≤12)}$, amido$_{(C≤12)}$, alkylimino$_{(C≤12)}$, alkenylimino$_{(C≤12)}$, alkynylimino$_{(C≤12)}$, arylimino$_{(C≤12)}$, aralkylimino$_{(C≤12)}$, heteroarylimino$_{(C≤12)}$, heteroaralkylimino$_{(C≤12)}$, acylimino$_{(C≤12)}$, alkylthio$_{(C≤12)}$, alkenylthio$_{(C≤12)}$, alkynylthio$_{(C≤12)}$, arylthio$_{(C≤12)}$, aralkylthio$_{(C≤12)}$, heteroarylthio$_{(C≤12)}$, heteroaralkylthio$_{(C≤12)}$, acylthio$_{(C≤12)}$, thioacyl$_{(C≤12)}$, alkylsulfonyl$_{(C≤12)}$, alkenylsulfonyl$_{(C≤12)}$, alkynylsulfonyl$_{(C≤12)}$, arylsulfonyl$_{(C≤12)}$, aralkylsulfonyl$_{(C≤12)}$, heteroarylsulfonyl$_{(C≤12)}$, heteroaralkylsulfonyl$_{(C≤12)}$, alkylammonium$_{(C≤12)}$, alkylsulfonium$_{(C≤12)}$, or alkylsilyl$_{(C≤12)}$, or a substituted version of any of these groups;

or pharmaceutically acceptable salts, hydrates, solvates, tautomers, prodrugs, or optical isomers thereof.

In certain embodiments, R₁ is cyano, halo, or a substituted acyl$_{(C≤8)}$. In other embodiments, R₂ is an alkyl$_{(C≤8)}$ or alkenyl$_{(C≤8)}$, or a substituted version thereof. In yet further embodiments, R₃ is a substituted alkyl$_{(C≤4)}$.

In particular embodiments, the compound of the invention is selected from the group of:

(1R,3aS,5aR,5bR,7aR,11aR,13aR,13bR)-10-cyano-5a,5b,8,8,11a-pentamethyl-9-oxo-1-(prop-1-en-2-yl)-N-(2,2,2-trifluoroethyl)-2,3,3a,4,5,5a,5b,6,7,7a,8,9,11a,11b,12,13,13a,13b-octadecahydro-1H-cyclopenta[a]chrysene-3a-carboxamide;

(1R,3aS,5aR,5bR,7aR,11aR,13aR,13bR)-10-cyano-N-(2,2-difluoroethyl)-5a,5b,8,8,11a-pentamethyl-9-oxo-1-(prop-1-en-2-yl)-2,3,3a,4,5,5a,5b,6,7,7a,8,9,11a,11b,12,13,13a,13b-octadecahydro-1H-cyclopenta[a]chrysene-3a-carboxamide;

(1R,3aS,5aR,5bR,7aR,11aR,13aR,13bR)-10-cyano-N-(2-fluoroethyl)-5a,5b,8,8,11a-pentamethyl-9-oxo-1-(prop-1-en-2-yl)-2,3,3a,4,5,5a,5b,6,7,7a,8,9,11a,11b,12,13,13a,13b-octadecahydro-1H-cyclopenta[a]chrysene-3a-carboxamide;

(1R,3aS,5aR,5bR,7aR,11aR,13aR,13bR)-5a,5b,8,8,11a-pentamethyl-9-oxo-1-(prop-1-en-2-yl)-2,3,3a,4,5,5a,5b,6,7,7a,8,9,11a,11b,12,13,13a,13b-octadecahydro-1H-cyclopenta[a]chrysene-3a,10-dicarbonitrile; and (1R,3aS,5aR,5bR,7aR,11aR,13aR,13bR)-10-cyano-5a,5b,8,8,11a-pentamethyl-9-oxo-1-(prop-1-en-2-yl)-2,3,3a,4,5,5a,5b,6,7,7a,8,9,11a,11b,12,13,13a,13b-octadecahydro-1H-cyclopenta[a]chrysene-3a-carboxylic anhydride.

The present invention also features a pharmaceutical composition containing, as an active ingredient, a compound of the invention and a pharmaceutically acceptable carrier.

Methods for treating cancer such as a carcinoma, sarcoma, lymphoma, leukemia, melanoma, mesothelioma, multiple myeloma, or seminoma or cancer of the bladder, blood, bone, brain, breast, central nervous system, colon, endometrium, esophagus, genitourinary tract, head, larynx, liver, lung, neck, ovary, pancreas, prostate, spleen, small intestine, large intestine, stomach, or testicle are provided as are methods for preventing or treating a disease with an inflammatory component, preventing or treating a neurodegenerative disease; preventing or treating a disorder characterized by overexpression of iNOS genes; inhibiting IFN-γ-induced nitric oxide production in cells; preventing or treating a disorder characterized by overexpression of COX-2 genes; and improving glomerular filtration rate or creatinine clearance. According to some embodiments, the methods of the invention embrace combination therapies.

Kits and articles of manufacture containing a compound of the invention are also provided, wherein some embodiments embrace the compound in a multiple dose form.

DETAILED DESCRIPTION OF THE INVENTION

Figure 1A:
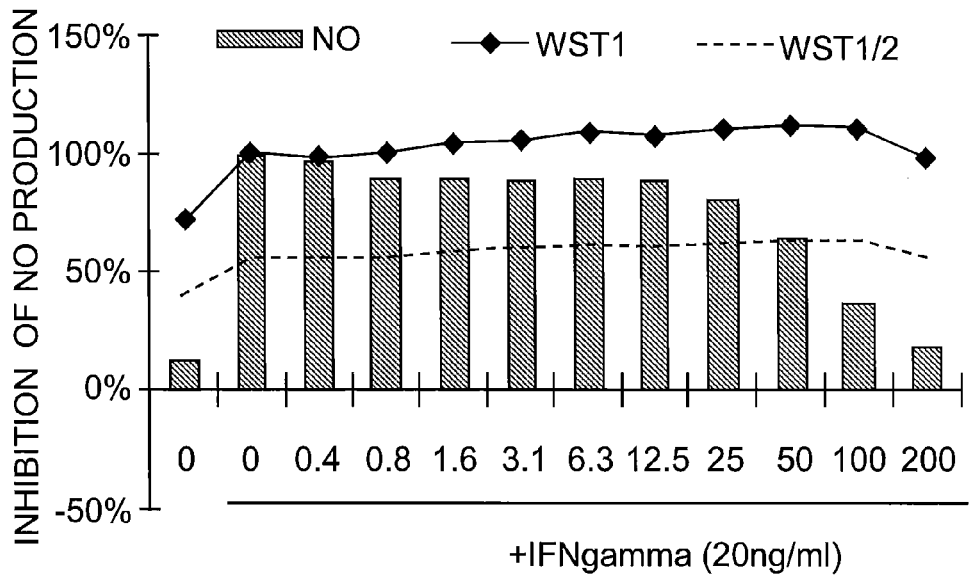
FIG. 1 shows inhibition of NO production by TP-321B (FIG. 1A), TP-342A (FIG. 1B), TP-343A (FIG. 1C) and TP-344A (FIG. 1D). RAW264.7 macrophages were pretreated with DMSO or drugs at various concentrations (nM) for 2 hours, and subsequently treated with 20 ng/ml IFNγ for 24 hours. NO concentration in media was determined using a Griess reagent system; cell viability was determined using WST-1 reagent. The betulinic acid derivatives are identified by their TP numbers, as shown herein and described in Example 5.
Figure 1B:
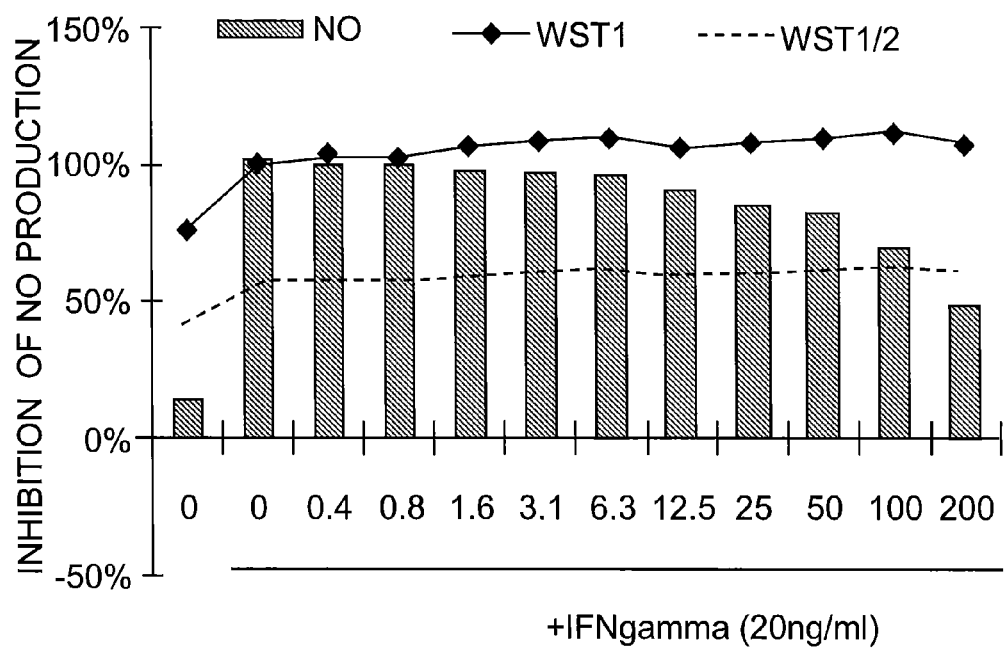
Figure 1C:
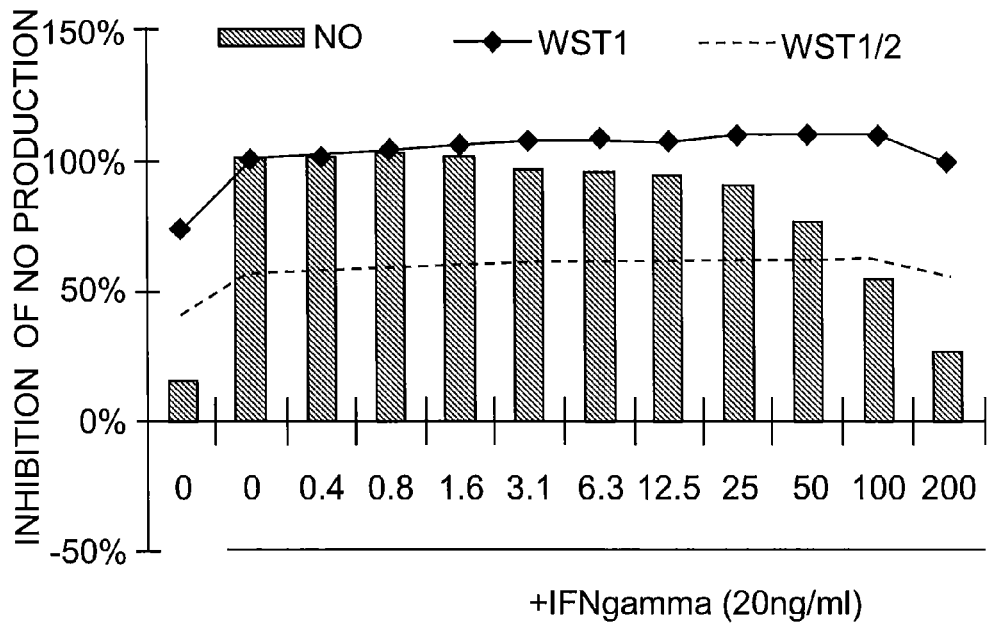
Figure 1D:
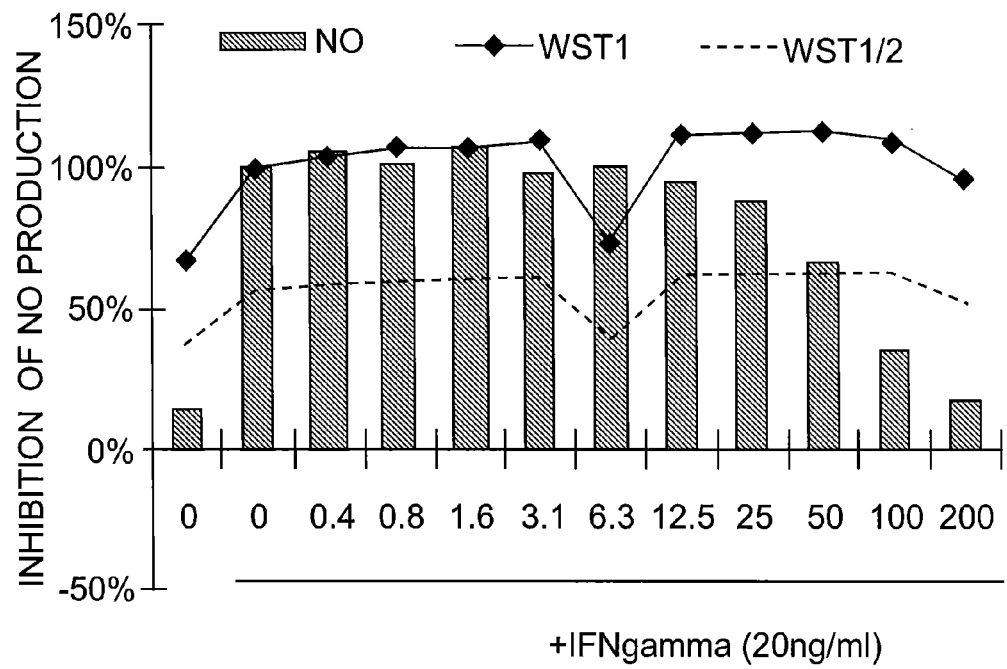

The present invention features new compounds and use of the same in methods for the treatment and prevention of cancer and diseases, including those characterized by the presence of oxidative stress or dysregulation of inflammation.

Compounds embraced by the present invention include those of the formula:

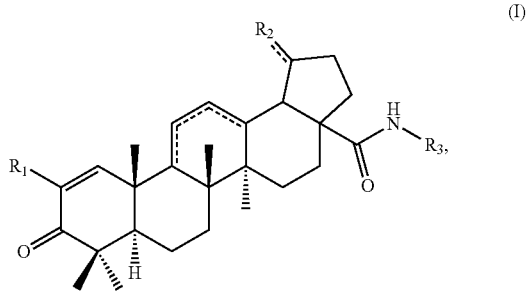

(I)

wherein, R₁ is cyano, halo, hydroxy, alkoxy$_{(C≤8)}$, substituted alkoxy$_{(C≤8)}$, acyl$_{(C≤8)}$, or substituted acyl$_{(C≤8)}$; R₂ is hydrogen, cyano, hydroxy, halo, amino or oxo, or alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, acyl$_{(C≤12)}$, alkylidene$_{(C≤12)}$, alkoxy$_{(C≤12)}$, alkenyloxy$_{(C≤12)}$, alkynyloxy$_{(C≤12)}$, aryloxy$_{(C≤12)}$, aralkoxy$_{(C≤12)}$, heteroaryloxy$_{(C≤12)}$, heteroaralkoxy$_{(C≤12)}$, acyloxy$_{(C≤12)}$, alkylamino$_{(C≤12)}$, dialkylamino$_{(C≤12)}$, alkoxyamino$_{(C≤12)}$, alkenylamino$_{(C≤12)}$, alkynylamino$_{(C≤12)}$, arylamino$_{(C≤12)}$, aralkylamino$_{(C≤12)}$, heteroarylamino$_{(C≤12)}$, heteroaralkylamino$_{(C≤12)}$, alkylsulfonylamino$_{(C≤12)}$, amido$_{(C≤12)}$, alkylimino$_{(C≤12)}$, alkenylimino$_{(C≤12)}$, alkynylimino$_{(C≤12)}$, arylimino$_{(C≤12)}$, aralkylimino$_{(C≤12)}$, heteroarylimino$_{(C≤12)}$, heteroaralkylimino$_{(C≤12)}$, acylimino$_{(C≤12)}$, alkylthio$_{(C≤12)}$, alkenylthio$_{(C≤12)}$, alkynylthio$_{(C≤12)}$, arylthio$_{(C≤12)}$, aralkylthio$_{(C≤12)}$, heteroarylthio$_{(C≤12)}$, heteroaralkylthio$_{(C≤12)}$, acylthio$_{(C≤12)}$, thioacyl$_{(C≤12)}$, alkylsulfonyl$_{(C≤12)}$, alkenylsulfonyl$_{(C≤12)}$, alkynylsulfonyl$_{(C≤12)}$, arylsulfonyl$_{(C≤12)}$, aralkylsulfonyl$_{(C≤12)}$, heteroarylsulfonyl$_{(C≤12)}$, heteroaralkylsulfonyl$_{(C≤12)}$, alkyl-ammonium$_{(C≤12)}$, alkylsulfonium$_{(C≤12)}$, or alkylsilyl$_{(C≤12)}$, or a substituted version of any of these groups; and $R_3$ is a substituted alkyl$_{(C≤8)}$; or pharmaceutically acceptable salts, hydrates, solvates, tautomers, prodrugs, or optical isomers thereof.

In one embodiment, compounds of the invention have the formula:

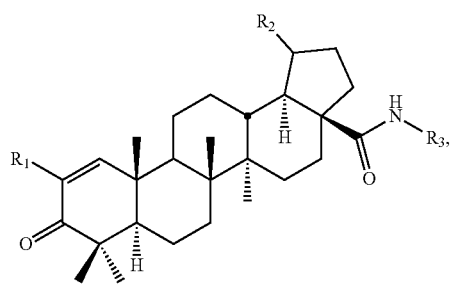

(II)

wherein, $R_1$ is cyano, halo, hydroxy, alkoxy$_{(C≤8)}$, substituted alkoxy$_{(C≤8)}$, acyl$_{(C≤8)}$, or substituted acyl$_{(C≤8)}$; $R_2$ is alkyl$_{(C≤8)}$, alkenyl$_{(C≤8)}$, aralkyl$_{(C≤8)}$, heteroaralkyl$_{(C≤8)}$, acyl$_{(C≤8)}$, alkylidene$_{(C≤8)}$, alkoxy$_{(C≤8)}$, aryloxy$_{(C≤8)}$, aralkoxy$_{(C≤8)}$, heteroaryloxy$_{(C≤8)}$, heteroaralkoxy$_{(C≤8)}$, acyloxy$_{(C≤8)}$, alkylamino$_{(C≤8)}$, dialkylamino$_{(C≤8)}$, alkoxyamino$_{(C≤8)}$, arylamino$_{(C≤8)}$, aralkylamino$_{(C≤8)}$, heteroarylamino$_{(C≤8)}$, heteroaralkylamino$_{(C≤8)}$, amido$_{(C≤8)}$, or a substituted version of any of these groups; and $R_3$ is a substituted alkyl$_{(C≤8)}$; or pharmaceutically acceptable salts, hydrates, solvates, tautomers, prodrugs, or optical isomers thereof.

In another embodiment, compounds of the invention have the formula:

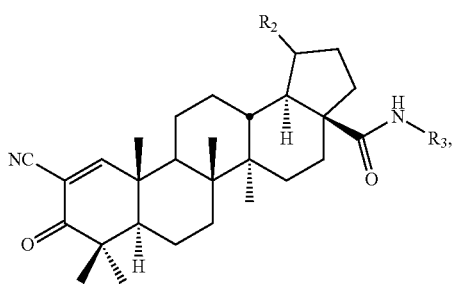

(III)

wherein, $R_2$ is alkyl$_{(C≤8)}$, alkenyl$_{(C≤8)}$, aralkyl$_{(C≤8)}$, heteroaralkyl$_{(C≤8)}$, acyl$_{(C≤8)}$, alkylidene$_{(C≤8)}$, alkoxy$_{(C≤8)}$, aryloxy$_{(C≤8)}$, aralkoxy$_{(C≤8)}$, heteroaryloxy$_{(C≤8)}$, heteroaralkoxy$_{(C≤8)}$, acyloxy$_{(C≤8)}$, alkylamino$_{(C≤8)}$, dialkylamino$_{(C≤8)}$, alkoxyamino$_{(C≤8)}$, arylamino$_{(C≤8)}$, aralkylamino$_{(C≤8)}$, heteroarylamino$_{(C≤8)}$, heteroaralkylamino$_{(C≤8)}$, amido$_{(C≤8)}$, or a substituted version of any of these groups; and $R_3$ is a substituted alkyl$_{(C≤8)}$; or pharmaceutically acceptable salts, hydrates, solvates, tautomers, prodrugs, or optical isomers thereof.

In a further embodiment, compounds of the invention have the formula:

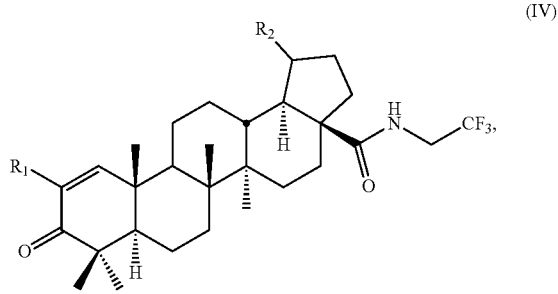

(IV)

wherein, $R_1$ is cyano, halo, hydroxy, alkoxy$_{(C≤8)}$, substituted alkoxy$_{(C≤8)}$, acyl$_{(C≤8)}$, or substituted acyl$_{(C≤8)}$; and $R_2$ is alkyl$_{(C≤8)}$, alkenyl$_{(C≤8)}$, aralkyl$_{(C≤8)}$, heteroaralkyl$_{(C≤8)}$, acyl$_{(C≤8)}$, alkylidene$_{(C≤8)}$, alkoxy$_{(C≤8)}$, aryloxy$_{(C≤8)}$, aralkoxy$_{(C≤8)}$, heteroaryloxy$_{(C≤8)}$, heteroaralkoxy$_{(C≤8)}$, acyloxy$_{(C≤8)}$, alkylamino$_{(C≤8)}$, dialkylamino$_{(C≤8)}$, heteroarylamino$_{(C≤8)}$, heteroaralkylamino$_{(C≤8)}$, amido$_{(C≤8)}$, or a substituted version of any of these groups; or pharmaceutically acceptable salts, hydrates, solvates, tautomers, prodrugs, or optical isomers thereof.

In yet further embodiments, compounds of the invention have the formula:

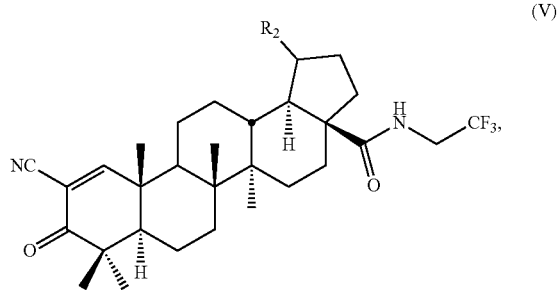

(V)

wherein $R_2$ is alkyl$_{(C≤8)}$, alkenyl$_{(C≤8)}$, aralkyl$_{(C≤8)}$, heteroaralkyl$_{(C≤8)}$, acyl$_{(C≤8)}$, alkylidene$_{(C≤8)}$, alkoxy$_{(C≤8)}$, aryloxy$_{(C≤8)}$, aralkoxy$_{(C≤8)}$, heteroaryloxy$_{(C≤8)}$, heteroaralkoxy$_{(C≤8)}$, acyloxy$_{(C≤8)}$, alkylamino$_{(C≤8)}$, dialkylamino$_{(C≤8)}$, alkoxyamino$_{(C≤8)}$, arylamino$_{(C≤8)}$, aralkylamino$_{(C≤8)}$, heteroarylamino$_{(C≤8)}$, heteroaralkylamino$_{(C≤8)}$, amido$_{(C≤8)}$, or a substituted version of any of these groups; or pharmaceutically acceptable salts, hydrates, solvates, tautomers, prodrugs, or optical isomers thereof.

In still further embodiments, compounds of the invention have the formula:

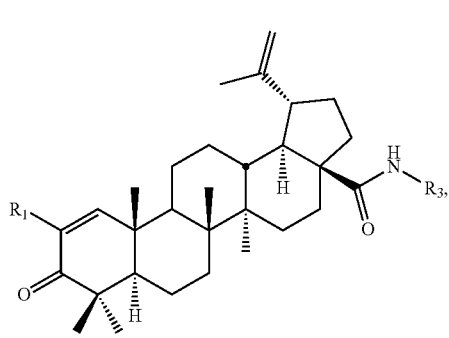

(VI)

wherein, $R_1$ is cyano, halo, hydroxy, alkoxy$_{(C\leq8)}$, substituted alkoxy$_{(C\leq8)}$, acyl$_{(C\leq8)}$, or substituted acyl$_{(C\leq8)}$; and $R_3$ is a substituted alkyl$_{(C\leq8)}$; or pharmaceutically acceptable salts, hydrates, solvates, tautomers, prodrugs, or optical isomers thereof.

The present invention also embraces compounds having the formula:

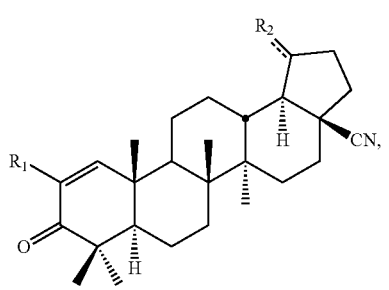

(VII)

wherein, $R_1$ is cyano, halo, hydroxy, alkoxy$_{(C\leq8)}$, substituted alkoxy$_{(C\leq8)}$, acyl$_{(C\leq8)}$, or substituted acyl$_{(C\leq8)}$; and $R_2$ is: hydrogen, cyano, hydroxy, halo or amino; or alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, acyl$_{(C\leq12)}$, alkylidene$_{(C\leq12)}$, alkoxy$_{(C\leq12)}$, alkenyloxy$_{(C\leq12)}$, alkynloxy$_{(C\leq12)}$, aryloxy$_{(C\leq12)}$, aralkoxy$_{(C\leq12)}$, heteroaryloxy$_{(C\leq12)}$, heteroaralkoxy$_{(C\leq12)}$, acyloxy$_{(C\leq12)}$, alkylamino$_{(C\leq12)}$, dialkylamino$_{(C\leq12)}$, alkoxyamino$_{(C\leq12)}$, alkenylamino$_{(C\leq12)}$, alkynylamino$_{(C\leq12)}$, arylamino$_{(C\leq12)}$, aralkylamino$_{(C\leq12)}$, heteroarylamino$_{(C\leq12)}$, heteroaralkylamino$_{(C\leq12)}$, alkyl-sulfonylamino$_{(C\leq12)}$, amido$_{(C\leq12)}$, alkylimino$_{(C\leq12)}$, alkenylimino$_{(C\leq12)}$, alkynylimino$_{(C\leq12)}$, arylimino$_{(C\leq12)}$, aralkylimino$_{(C\leq12)}$, heteroarylimino$_{(C\leq12)}$, heteroaralkylimino$_{(C\leq12)}$, acylimino$_{(C\leq12)}$, alkylthio$_{(C\leq12)}$, alkenylthio$_{(C\leq12)}$, alkynylthio$_{(C\leq12)}$, arylthio$_{(C\leq12)}$, aralkylthio$_{(C\leq12)}$, heteroarylthio$_{(C\leq12)}$, heteroaralkylthio$_{(C\leq12)}$, acylthio$_{(C\leq12)}$, thioacyl$_{(C\leq12)}$, alkylsulfonyl$_{(C\leq12)}$, alkenylsulfonyl$_{(C\leq12)}$, alkynylsulfonyl$_{(C\leq12)}$, arylsulfonyl$_{(C\leq12)}$, aralkylsulfonyl$_{(C\leq12)}$, heteroarylsulfonyl$_{(C\leq12)}$, heteroaralkylsulfonyl$_{(C\leq12)}$, alkylammonium$_{(C\leq12)}$, alkylsulfonium$_{(C\leq12)}$, or alkylsilyl$_{(C\leq12)}$, or a substituted version of any of these groups; or pharmaceutically acceptable salts, hydrates, solvates, tautomers, prodrugs, or optical isomers thereof.

In one embodiment, compounds of the invention have the formula:

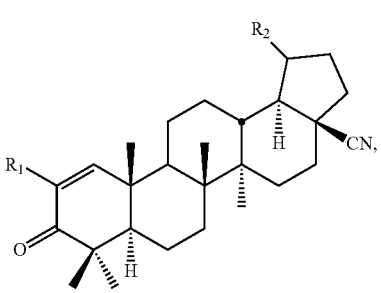

(VIII)

wherein, $R_1$ is cyano, halo, hydroxy, alkoxy$_{(C\leq8)}$, substituted alkoxy$_{(C\leq8)}$, acyl$_{(C\leq8)}$, or substituted acyl$_{(C\leq8)}$; and $R_2$ is alkyl$_{(C\leq8)}$, alkenyl$_{(C\leq8)}$, aralkyl$_{(C\leq8)}$, heteroaralkyl$_{(C\leq8)}$, acyl$_{(C\leq8)}$, alkylidene$_{(C\leq8)}$, alkoxy$_{(C\leq8)}$, aryloxy$_{(C\leq8)}$, aralkoxy$_{(C\leq8)}$, heteroaryloxy$_{(C\leq8)}$, heteroaralkoxy$_{(C\leq8)}$, acyloxy$_{(C\leq8)}$, alkylamino$_{(C\leq8)}$, dialkylamino$_{(C\leq8)}$, alkoxyamino$_{(C\leq8)}$, arylamino$_{(C\leq8)}$, aralkylamino$_{(C\leq8)}$, heteroarylamino$_{(C\leq8)}$, heteroaralkylamino$_{(C\leq8)}$, amido$_{(C\leq8)}$, or a substituted version of any of these groups; or pharmaceutically acceptable salts, hydrates, solvates, tautomers, prodrugs, or optical isomers thereof.

In particular embodiments of the formulae disclosed herein, $R_1$ is cyano. In other variations, $R_1$ is halo. In still other variations, $R_1$ is chloro. In further variations, $R_1$ is a substituted acyl$_{(C\leq8)}$. For example, $R_1$ can be a substituted acyl$_{(C\leq3)}$. For example, $R_1$ can be —C(O)OH or —C(O)OMe.

In particular embodiments of the formulae disclosed herein, $R_2$ is an alkyl$_{(C\leq8)}$ or alkenyl$_{(C\leq8)}$, or a substituted version of either of these groups. In some variations, $R_2$ is an alkyl$_{(C\leq4)}$ or alkenyl$_{(C\leq4)}$, or a substituted version of either of these groups. In further variations, $R_2$ is an alkyl$_{(C\leq3)}$ or alkenyl$_{(C\leq3)}$, or a substituted version of either of these groups. For example, $R_2$ can be isopropyl, isopropenyl, hydroxy-substituted isopropenyl or a fluoro-substituted isopropenyl.

In particular embodiments of the formulae disclosed herein, $R_3$ is a substituted alkyl$_{(C\leq4)}$. In some variations, $R_3$ is a substituted alkyl$_{(C\leq2)}$. In some variations, $R_3$ is a fluoro substituted alkyl$_{(C\leq4)}$, for example, 2,2,2-trifluoroethyl, 2,2-difluoroethyl or 2-fluoroethyl.

As used herein, "hydrogen" means —H; "hydroxy" means —OH; "oxo" means =O; "halo" means independently —F, —Cl, —Br or —I; "amino" means —NH$_2$ (see definitions herein of groups containing the term amino, e.g., alkylamino); "hydroxyamino" means —NHOH; "nitro" means —NO$_2$; imino means =NH (see definitions herein of groups containing the term imino, e.g., alkylamino); "cyano" means —CN; "azido" means —N$_3$; "mercapto" means —SH; "thio" means =S; "sulfonamido" means —NHS(O)$_2$— (see definitions herein of groups containing the term sulfonamido, e.g., alkylsulfonamido); "sulfonyl" means —S(O)$_2$— (see definitions herein of groups containing the term sulfonyl, e.g., alkylsulfonyl); and "silyl" means —SiH$_3$ (see definitions herein of group(s) containing the term silyl, e.g., alkylsilyl).

For the groups that follow, the following parenthetical subscripts further define the groups as follows: "(Cn)" defines the exact number (n) of carbon atoms in the group; "(C≤n)" defines the maximum number (n) of carbon atoms that can be in the group; (Cn-n') defines both the minimum (n) and maximum number (n') of carbon atoms in the group. For example, "alkoxy$_{(C\leq10)}$" designates those alkoxy groups having from 1 to 10 carbon atoms (e.g., 1, 2, 3, 4, 5, 6, 7, 8, 9, or 10, or any range derivable therein (e.g., 3-10 carbon atoms)). Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3-10 carbon atoms)).

The term "alkyl," when used without the "substituted" modifier, refers to a non-aromatic monovalent group with a saturated carbon atom as the point of attachment, a linear or branched, cyclo, cyclic or acyclic structure, no carbon-carbon double or triple bonds, and no atoms other than carbon and hydrogen. The groups, —CH$_2$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "saturated" when referring to an atom means that the atom is connected to other atoms only by means of single bonds. The term "substituted alkyl" refers to a non-aromatic monovalent group with a saturated carbon atom as the point of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkyl groups: —CH$_2$OH, —CH$_2$Cl, —CH$_2$Br, —CH$_2$SH, —CF$_3$, —CH$_2$CN, —CH$_2$C(O)H, —CH$_2$C(O)OH, —CH$_2$C(O)OCH$_3$, —CH$_2$C(O)NH$_2$, —CH$_2$C(O)NHCH$_3$, —CH$_2$O(O)CH$_3$, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, —CH$_2$CF$_3$, —CH$_2$CH$_2$OC(O)CH$_3$, —CH$_2$CH$_2$NHCO$_2$C(CH$_3$)$_3$, and —CH$_2$Si(CH$_3$)$_3$. In particular embodiments of the invention, the alkyl is C$_{(3-12)}$.

The term "alkanediyl," when used without the "substituted" modifier, refers to a non-aromatic divalent group, wherein the alkanediyl group is attached with two σ-bonds, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

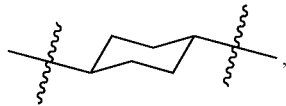 [SMILES: *C1CCC(*)CC1]

are non-limiting examples of alkanediyl groups. The term "substituted alkanediyl" refers to a non-aromatic monovalent group, wherein the alkynediyl group is attached with two σ-bonds, with one or two saturated carbon atom(s) as the point(s) of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkanediyl groups: —CH(F)—, —CF$_2$—, —CH(Cl)—, —CH(OH)—, —CH(OCH$_3$)—, and —CH$_2$CH(Cl)—.

The term "alkenyl," when used without the "substituted" modifier, refers to a monovalent group with a nonaromatic carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH═CH$_2$ (vinyl), —CH═CHCH$_3$, —CH═CHCH$_2$CH$_3$, —CH$_2$CH═CH$_2$ (allyl), —CH$_2$CH═CHCH$_3$, and —CH═CH—C$_6$H$_5$. The term "substituted alkenyl" refers to a monovalent group with a nonaromatic carbon atom as the point of attachment, at least one nonaromatic carbon-carbon double bond, no carbon-carbon triple bonds, a linear or branched, cyclo, cyclic or acyclic structure, and at least one atom independently selected from the group consisting of N, O, F, Cl, Br, I, Si, P, and S. The groups, —CH═CHF, —CH═CHCl and —CH═CHBr, are non-limiting examples of substituted alkenyl groups.

The term "alkenediyl," when used without the "substituted" modifier, refers to a non-aromatic divalent group, wherein the alkenediyl group is attached with two σ-bonds, with two carbon atoms as points of attachment, a linear or branched, cyclo, cyclic or acyclic structure, at least one non-aromatic carbon-carbon double bond, no carbon-carbon triple bonds, and no atoms other than carbon and hydrogen. The groups, —CH═CH—, —CH═C(CH$_3$)CH$_2$—, —CH═CHCH$_2$—, and

are non-limiting examples of alkenediyl groups. The term "substituted alkenediyl" refers to a non-aromatic divalent group, wherein the alkenediyl group is attached with two σ-bonds, with two carbon atoms as points of attachment, a linear or branched, cyclo, cyclic or acyclic structure, at least one nonaromatic carbon-carbon double bond, no carbon-carbon triple bonds, and at least one atom independently selected from the group consisting of N, O, F, Cl, Br, I, Si, P, and S. The following groups are non-limiting examples of substituted alkenediyl groups: —CF═CH—, —C(OH)═CH—, and —CH$_2$CH═C(Cl)—.

The term "alkynyl," when used without the "substituted" modifier, refers to a monovalent group with a nonaromatic carbon atom as the point of attachment, a linear or branched, cyclo, cyclic or acyclic structure, at least one carbon-carbon triple bond, and no atoms other than carbon and hydrogen. The groups, —C≡CH, —C≡CCH$_3$, —C≡CC$_6$H$_5$ and —CH$_2$C≡CCH$_3$, are non-limiting examples of alkynyl groups. The term "substituted alkynyl" refers to a monovalent group with a nonaromatic carbon atom as the point of attachment and at least one carbon-carbon triple bond, a linear or branched, cyclo, cyclic or acyclic structure, and at least one atom independently selected from the group consisting of N, O, F, Cl, Br, I, Si, P, and S. The group, —C≡C Si(CH$_3$)$_3$, is a non-limiting example of a substituted alkynyl group.

The term "alkynediyl," when used without the "substituted" modifier, refers to a non-aromatic divalent group, wherein the alkynediyl group is attached with two σ-bonds, with two carbon atoms as points of attachment, a linear or branched, cyclo, cyclic or acyclic structure, at least one carbon-carbon triple bond, and no atoms other than carbon and hydrogen. The groups, —C≡C—, —C≡CCH$_2$—, and —C≡CCH(CH$_3$)— are non-limiting examples of alkynediyl groups. The term "substituted alkynediyl" refers to a non-aromatic divalent group, wherein the alkynediyl group is attached with two σ-bonds, with two carbon atoms as points of attachment, a linear or branched, cyclo, cyclic or acyclic structure, at least one carbon-carbon triple bond, and at least one atom independently selected from the group consisting of N, O, F, Cl, Br, I, Si, P, and S. The groups —C≡CCFH— and —C≡CHCH(Cl)— are non-limiting examples of substituted alkynediyl groups.

The term "aryl," when used without the "substituted" modifier, refers to a monovalent group with an aromatic carbon atom as the point of attachment, said carbon atom forming part of a six-membered aromatic ring structure wherein the ring atoms are all carbon, and wherein the monovalent group consists of no atoms other than carbon and hydrogen. Non-limiting examples of aryl groups include phenyl (Ph), methylphenyl, (dimethyl)phenyl, —C$_6$H$_4$CH$_2$CH$_3$ (ethylphenyl), —C$_6$H$_4$CH$_2$CH$_2$CH$_3$ (propylphenyl), —C$_6$H$_4$CH(CH$_3$)$_2$, —C$_6$H$_4$CH(CH$_2$)$_2$, —C$_6$H$_3$(CH$_3$)CH$_2$CH$_3$ (methylethylphenyl), —C$_6$H$_4$CH=CH$_2$ (vinylphenyl), —C$_6$H$_4$CH=CHCH$_3$, —C$_6$H$_4$C≡CH, —C$_6$H$_4$C≡CCH$_3$, naphthyl, and the monovalent group derived from biphenyl. The term "substituted aryl" refers to a monovalent group with an aromatic carbon atom as the point of attachment, said carbon atom forming part of a six-membered aromatic ring structure wherein the ring atoms are all carbon, and wherein the monovalent group further has at least one atom independently selected from the group consisting of N, O, F, Cl, Br, I, Si, P, and S, Non-limiting examples of substituted aryl groups include the groups: —C$_6$H$_4$F, —C$_6$H$_4$Cl, —C$_6$H$_4$Br, —C$_6$H$_4$I, —C$_6$H$_4$OH, —C$_6$H$_4$OCH$_3$, —C$_6$H$_4$OCH$_2$CH$_3$, —C$_6$H$_4$OC(O)CH$_3$, —C$_6$H$_4$NH$_2$, —C$_6$H$_4$NHCH$_3$, —C$_6$H$_4$N(CH$_3$)$_2$, —C$_6$H$_4$CH$_2$OH, —C$_6$H$_4$CH$_2$OC(O)CH$_3$, —C$_6$H$_4$CH$_2$NH$_2$, —C$_6$H$_4$CF$_3$, —C$_6$H$_4$CN, —C$_6$H$_4$CHO, —C$_6$H$_4$CHO, —C$_6$H$_4$C(O)CH$_3$, —C$_6$H$_4$C(O)C$_6$H$_5$, —C$_6$H$_4$CO$_2$H, —C$_6$H$_4$CO$_2$CH$_3$, —C$_6$H$_4$CONH$_2$, —C$_6$H$_4$CONHCH$_3$, and —C$_6$H$_4$CON(CH$_3$)$_2$.

The term "arenediyl," when used without the "substituted" modifier, refers to a divalent group, wherein the arenediyl group is attached with two σ-bonds, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. Non-limiting examples of arenediyl groups include:

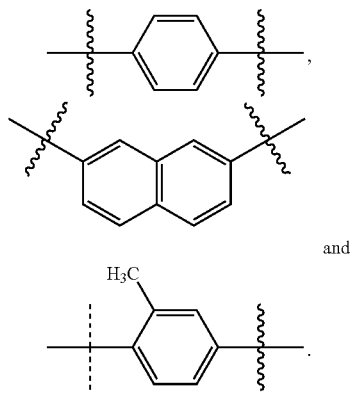

and

The term "substituted arenediyl" refers to a divalent group, wherein the arenediyl group is attached with two σ-bonds, with two aromatic carbon atoms as points of attachment, said carbon atoms forming part of one or more six-membered aromatic rings structure(s), wherein the ring atoms are all carbon, and wherein the divalent group further has at least one atom independently selected from the group consisting of N, O, F, Cl, Br, I, Si, P, and S.

The term "aralkyl," when used without the "substituted" modifier, refers to the monovalent group -alkanediyl-aryl, in which the terms alkanediyl and aryl are each used in a manner consistent with the definitions provided herein. Non-limiting examples of aralkyls are: phenylmethyl (benzyl, Bn), 1-phenyl-ethyl, 2-phenyl-ethyl, indenyl and 2,3-dihydro-indenyl, provided that indenyl and 2,3-dihydro-indenyl are only examples of aralkyl in so far as the point of attachment in each case is one of the saturated carbon atoms. When the term "aralkyl" is used with the "substituted" modifier, either one or both the alkanediyl and the aryl is substituted. Non-limiting examples of substituted aralkyls are: (3-chlorophenyl)-methyl, 2-oxo-2-phenyl-ethyl (phenylcarbonylmethyl), 2-chloro-2-phenyl-ethyl, chromanyl where the point of attachment is one of the saturated carbon atoms, and tetrahydroquinolinyl where the point of attachment is one of the saturated atoms.

The term "heteroaryl," when used without the "substituted" modifier, refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group consists of no atoms other than carbon, hydrogen, aromatic nitrogen, aromatic oxygen and aromatic sulfur. Non-limiting examples of aryl groups include acridinyl, furanyl, imidazoimidazolyl, imidazopyrazolyl, imidazopyridinyl, imidazopyrimidinyl, indolyl, indazolinyl, methylpyridyl, oxazolyl, phenylimidazolyl, pyridyl, pyrrolyl, pyrimidyl, pyrazinyl, quinolyl, quinazolyl, quinoxalinyl, tetrahydroquinolinyl, thienyl, triazinyl, pyrrolopyridinyl, pyrrolopyrimidinyl, pyrrolopyrazinyl, pyrrolotriazinyl, pyrroloimidazolyl, chromenyl (where the point of attachment is one of the aromatic atoms), and chromanyl (where the point of attachment is one of the aromatic atoms). The term "substituted heteroaryl" refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group further has at least one atom independently selected from the group consisting of non-aromatic nitrogen, non-aromatic oxygen, non aromatic sulfur F, Cl, Br, I, Si, and P.

The term "heteroarenediyl," when used without the "substituted" modifier, refers to a divalent group, wherein the heteroarenediyl group is attached with two σ-bonds, with an aromatic carbon atom or nitrogen atom as the point of attachment, said carbon atom or nitrogen atom two aromatic atoms as points of attachment, said carbon atoms forming part of one or more six-membered aromatic ring structure(s) wherein the ring atoms are all carbon, and wherein the monovalent group consists of no atoms other than carbon and hydrogen. Non-limiting examples of heteroarenediyl groups include:

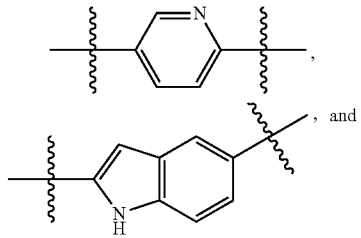

, and

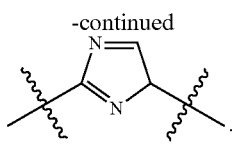

The term "substituted heteroarenediyl" refers to a divalent group, wherein the heteroarenediyl group is attached with two σ-bonds, with two aromatic carbon atoms as points of attachment, said carbon atoms forming part of one or more six-membered aromatic rings structure(s), wherein the ring atoms are all carbon, and wherein the divalent group further has at least one atom independently selected from the group consisting of N, O, F, Cl, Br, I, Si, P, and S.

The term "heteroaralkyl," when used without the "substituted" modifier, refers to the monovalent group -alkanediyl-heteroaryl, in which the terms alkanediyl and heteroaryl are each used in a manner consistent with the definitions provided above. Non-limiting examples of aralkyls are: pyridylmethyl, and thienylmethyl. When the term "heteroaralkyl" is used with the "substituted" modifier, either one or both the alkanediyl and the heteroaryl is substituted.

The term "acyl," when used without the "substituted" modifier, refers to a monovalent group with a carbon atom of a carbonyl group as the point of attachment, further having a linear or branched, cyclo, cyclic or acyclic structure, further having no additional atoms that are not carbon or hydrogen, beyond the oxygen atom of the carbonyl group. The groups, —CHO, —C(O)CH$_3$, —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)C$_6$H$_4$CH$_2$CH$_3$, —COC$_6$H$_3$(CH$_3$)$_2$, and —C(O)CH$_2$C$_6$H$_5$, are non-limiting examples of acyl groups. The term "acyl" therefore encompasses, but is not limited to, groups sometimes referred to as "alkyl carbonyl" and "aryl carbonyl" groups. The term "substituted acyl" refers to a monovalent group with a carbon atom of a carbonyl group as the point of attachment, further having a linear or branched, cyclo, cyclic or acyclic structure, further having at least one atom, in addition to the oxygen of the carbonyl group, independently selected from the group consisting of N, O, F, Cl, Br, I, Si, P, and S. The groups, —C(O)CH$_2$CF$_3$, —CO$_2$H (carboxyl), —CO$_2$CH$_3$ (methylcarboxyl), —CO$_2$CH$_2$CH$_3$, —CO$_2$CH$_2$CH$_2$CH$_3$, —CO$_2$C$_6$H$_5$, —CO$_2$CH(CH$_3$)$_2$, —CO$_2$CH(CH$_2$)$_2$, —C(O)NH$_2$ (carbamoyl)), —C(O)NHCH$_3$, —C(O)NHCH$_2$CH$_3$, —CONHCH(CH$_3$)$_2$, —CONHCH(CH$_2$)$_2$, —CON(CH$_3$)$_2$, —CONHCH$_2$CF$_3$, —CO-pyridyl, —CO-imidazoyl, and —C(O)N$_3$, are non-limiting examples of substituted acyl groups. The term "substituted acyl" encompasses, but is not limited to, "heteroaryl carbonyl" groups.

The term "alkylidene," when used without the "substituted" modifier, refers to the divalent group =CRR', wherein the alkylidene group is attached with one σ-bond and one π-bond, in which R and R' are independently hydrogen, alkyl, or R and R' are taken together to represent alkanediyl. Non-limiting examples of alkylidene groups include: =CH$_2$, =CH(CH$_2$CH$_3$), and =C(CH$_3$)$_2$. The term "substituted alkylidene" refers to the group =CRR', wherein the alkylidene group is attached with one σ-bond and one π-bond, in which R and R' are independently hydrogen, alkyl, substituted alkyl, or R and R' are taken together to represent a substituted alkanediyl, provided that either one of R and R' is a substituted alkyl or R and R' are taken together to represent a substituted alkanediyl.

The term "alkoxy," when used without the "substituted" modifier, refers to the group —OR, in which R is an alkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopentyl, and —O-cyclohexyl. The term "substituted alkoxy" refers to the group —OR, in which R is a substituted alkyl, as that term is defined above. For example, —OCH$_2$CF$_3$ is a substituted alkoxy group.

Similarly, the terms "alkenyloxy", "alkynyloxy", "aryloxy", "aralkoxy", "heteroaryloxy", "heteroaralkoxy" and "acyloxy," when used without the "substituted" modifier, refers to groups, defined as —OR, in which R is alkenyl, alkynyl, aryl, aralkyl, heteroaryl, heteroalkyl and acyl, respectively, as those terms are defined herein. When any of the terms alkenyloxy, alkynyloxy, aryloxy, aralkyloxy and acyloxy is modified by "substituted," it refers to the group —OR, in which R is substituted alkenyl, alkynyl, aryl, aralkyl, heteroaryl, heteroalkyl and acyl, respectively.

The term "alkylamino," when used without the "substituted" modifier, refers to the group —NHR, in which R is an alkyl, as that term is defined above. Non-limiting examples of alkylamino groups include: —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC(CH$_3$)$_3$, —NH-cyclopentyl, and —NH-cyclohexyl. The term "substituted alkylamino" refers to the group —NHR, in which R is a substituted alkyl, as that term is defined above. For example, —NHCH$_2$CF$_3$ is a substituted alkylamino group.

The term "dialkylamino," when used without the "substituted" modifier, refers to the group —NRR', in which R and R' can be the same or different alkyl groups, or R and R' can be taken together to represent an alkanediyl having two or more saturated carbon atoms, at least two of which are attached to the nitrogen atom. Non-limiting examples of dialkylamino groups include: —NHC(CH$_3$)$_3$, —N(CH$_3$)CH$_2$CH$_3$, —N(CH$_2$CH$_3$)$_2$, N-pyrrolidinyl, and N-piperidinyl. The term "substituted dialkylamino" refers to the group —NRR', in which R and R' can be the same or different substituted alkyl groups, one of R or R' is an alkyl and the other is a substituted alkyl, or R and R' can be taken together to represent a substituted alkanediyl with two or more saturated carbon atoms, at least two of which are attached to the nitrogen atom.

The terms "alkoxyamino", "alkenylamino", "alkynylamino", "arylamino", "aralkylamino", "heteroarylamino", "heteroaralkylamino", and "alkylsulfonylamino," when used without the "substituted" modifier, refer to groups, defined as —NHR, in which R is alkoxy, alkenyl, alkynyl, aryl, aralkyl, heteroaryl, heteroalkyl and alkylsulfonyl, respectively, as those terms are defined herein. A non-limiting example of an arylamino group is —NHC$_6$H$_5$. When any of the terms alkoxyamino, alkenylamino, alkynylamino, arylamino, aralkylamino, heteroarylamino, heteroaralkylamino and alkylsulfonylamino is modified by "substituted," it refers to the group —NHR, in which R is substituted alkoxy, alkenyl, alkynyl, aryl, aralkyl, heteroaryl, heteroalkyl and alkylsulfonyl, respectively.

The term "amido" (acylamino), when used without the "substituted" modifier, refers to the group —NHR, in which R is acyl, as that term is defined herein. A non-limiting example of an acylamino group is —NHC(O)CH$_3$. When the term amido is used with the "substituted" modifier, it refers to groups, defined as —NHR, in which R is substituted acyl, as that term is defined herein. The groups —NHC(O)OCH$_3$ and —NHC(O)NHCH$_3$ are non-limiting examples of substituted amido groups.

The term "alkylimino," when used without the "substituted" modifier, refers to the group =NR, wherein the alkylimino group is attached with one σ-bond and one π-bond, in which R is an alkyl, as that term is defined herein. Non-limiting examples of alkylimino groups include: =NCH$_3$, =NCH$_2$CH$_3$ and =N-cyclohexyl. The term "substituted alkylimino" refers to the group =NR, wherein the alkylimino group is attached with one σ-bond and one π-bond, in which R is a substituted alkyl, as that term is defined above. For example, =NCH$_2$CF$_3$ is a substituted alkylimino group.

Similarly, the terms "alkenylimino", "alkynylimino", "arylimino", "aralkylimino", "heteroarylimino", "heteroaralkylimino" and "acylimino," when used without the "substituted" modifier, refer to groups, defined as =NR, wherein the alkylimino group is attached with one σ-bond and one π-bond, in which R is alkenyl, alkynyl, aryl, aralkyl, heteroaryl, heteroaralkyl and acyl, respectively, as those terms are defined herein. When any of the terms alkenylimino, alkynylimino, arylimino, aralkylimino and acylimino is modified by "substituted," it refers to the group =NR, wherein the alkylimino group is attached with one σ-bond and one π-bond, in which R is substituted alkenyl, alkynyl, aryl, aralkyl, heteroaryl, heteroaralkyl and acyl, respectively.

The term "alkylthio," when used without the "substituted" modifier, refers to the group —SR, in which R is an alkyl, as that term is defined herein. Non-limiting examples of alkylthio groups include: —SCH$_3$, —SCH$_2$CH$_3$, —SCH$_2$CH$_2$CH$_3$, —SCH(CH$_3$)$_2$, —SCH(CH$_2$)$_2$, —S-cyclopentyl, and —S-cyclohexyl. The term "substituted alkylthio" refers to the group —SR, in which R is a substituted alkyl, as that term is defined herein. For example, —SCH$_2$CF$_3$ is a substituted alkylthio group.

Similarly, the terms "alkenylthio", "alkynylthio", "arylthio", "aralkylthio", "heteroarylthio", "heteroaralkylthio", and "acylthio," when used without the "substituted" modifier, refer to groups, defined as —SR, in which R is alkenyl, alkynyl, aryl, aralkyl, heteroaryl, heteroaralkyl and acyl, respectively, as those terms are defined herein. When any of the terms alkenylthio, alkynylthio, arylthio, aralkylthio, heteroarylthio, heteroaralkylthio, and acylthio is modified by "substituted," it refers to the group —SR, in which R is substituted alkenyl, alkynyl, aryl, aralkyl, heteroaryl, heteroaralkyl and acyl, respectively.

The term "thioacyl," when used without the "substituted" modifier, refers to a monovalent group with a carbon atom of a thiocarbonyl group as the point of attachment, further having a linear or branched, cyclo, cyclic or acyclic structure, further having no additional atoms that are not carbon or hydrogen, beyond the sulfur atom of the carbonyl group. The groups, —CHS, —C(S)CH$_3$, —C(S)CH$_2$CH$_3$, —C(S)CH$_2$CH$_2$CH$_3$, —C(S)CH(CH$_3$)$_2$, —C(S)CH(CH$_2$)$_2$, —C(S)C$_6$H$_5$, —C(S)C$_6$H$_4$CH$_3$, —C(S)C$_6$H$_4$CH$_2$CH$_3$, —C(S)C$_6$H$_3$(CH$_3$)$_2$, and —C(S)CH$_2$C$_6$H$_5$, are non-limiting examples of thioacyl groups. The term "thioacyl" therefore encompasses, but is not limited to, groups sometimes referred to as "alkyl thiocarbonyl" and "aryl thiocarbonyl" groups. The term "substituted thioacyl" refers to a radical with a carbon atom as the point of attachment, the carbon atom being part of a thiocarbonyl group, further having a linear or branched, cyclo, cyclic or acyclic structure, further having at least one atom, in addition to the sulfur atom of the carbonyl group, independently selected from the group of N, O, F, Cl, Br, I, Si, P, and S. The groups, —C(S)CH$_2$CF$_3$, —C(S)O$_2$H, —C(S)OCH$_3$, —C(S)OCH$_2$CH$_3$, —C(S)OCH$_2$CH$_2$CH$_3$, —C(S)OC$_6$H$_5$, —C(S)OCH(CH$_3$)$_2$, —C(S)OCH(CH$_2$)$_2$, —C(S)NH$_2$, and —C(S)NHCH$_3$, are non-limiting examples of substituted thioacyl groups. The term "substituted thioacyl" encompasses, but is not limited to, "heteroaryl thiocarbonyl" groups.

The term "alkylsulfonyl," when used without the "substituted" modifier, refers to the group —S(O)$_2$R, in which R is an alkyl, as that term is defined herein. Non-limiting examples of alkylsulfonyl groups include: —S(O)$_2$CH$_3$, —S(O)$_2$CH$_2$CH$_3$, —S(O)$_2$CH$_2$CH$_2$CH$_3$, —S(O)$_2$CH(CH$_3$)$_2$, —S(O)$_2$CH(CH$_2$)$_2$, —S(O)$_2$-cyclopentyl, and —S(O)$_2$-cyclohexyl. The term "substituted alkylsulfonyl" refers to the group —S(O)$_2$R, in which R is a substituted alkyl, as that term is defined herein. For example, —S(O)$_2$CH$_2$CF$_3$ is a substituted alkylsulfonyl group.

Similarly, the terms "alkenylsulfonyl", "alkynylsulfonyl", "arylsulfonyl", "aralkylsulfonyl", "heteroarylsulfonyl", and "heteroaralkylsulfonyl," when used without the "substituted" modifier, refer to groups, defined as —S(O)$_2$R, in which R is alkenyl, alkynyl, aryl, aralkyl, heteroaryl, and heteroaralkyl, respectively, as those terms are defined herein. When any of the terms alkenylsulfonyl, alkynylsulfonyl, arylsulfonyl, aralkylsulfonyl, heteroarylsulfonyl, and heteroaralkylsulfonyl is modified by "substituted," it refers to the group —S(O)$_2$R, in which R is substituted alkenyl, alkynyl, aryl, aralkyl, heteroaryl and heteroaralkyl, respectively.

The term "alkylammonium," when used without the "substituted" modifier, refers to a group, defined as —NH$_2$R$^+$, —NHRR'$^+$, or —NRR'R''$^+$, in which R, R' and R'' are the same or different alkyl groups, or any combination of two of R, R' and R'' can be taken together to represent an alkanediyl. Non-limiting examples of alkylammonium cation groups include: —NH$_2$(CH$_3$)$^+$, —NH$_2$(CH$_2$CH$_3$)$+$, —NH$_2$(CH$_2$CH$_2$CH$_3$)$+$, —NH(CH$_3$)$_2$$^+$, —NH(CH$_2$CH$_3$)$_2$$^+$, —NH(CH$_2$CH$_2$CH$_3$)$_2$$^+$, —N(CH$_3$)$_3$$^+$, —N(CH$_3$)(CH$_2$CH$_3$)$_2$$^+$, —N(CH$_3$)$_2$(CH$_2$CH$_3$)$^+$, —NH$_2$C(CH$_3$)$_3$$^+$, —NH(cyclopentyl)$_2$$^+$, and —NH$_2$(cyclohexyl)$^+$. The term "substituted alkylammonium" refers —NH$_2$R$^+$, —NHRR'$^+$, or —NRR'R''$^+$, in which at least one of R, R' and R'' is a substituted alkyl or two of R, R' and R'' can be taken together to represent a substituted alkanediyl. When more than one of R, R' and R'' is a substituted alkyl, they can be the same of different. Any of R, R' and R'' that are not either substituted alkyl or substituted alkanediyl, can be either alkyl, either the same or different, or can be taken together to represent an alkanediyl with two or more carbon atoms, at least two of which are attached to the nitrogen atom shown in the formula.

The term "alkylsulfonium," when used without the "substituted" modifier, refers to the group —SRR'$^+$, in which R and R' can be the same or different alkyl groups, or R and R' can be taken together to represent an alkanediyl. Non-limiting examples of alkylsulfonium groups include: —SH(CH$_3$)$^+$, —SH(CH$_2$CH$_3$)$^+$, —SH(CH$_2$CH$_2$CH$_3$)$^+$, —S(CH$_3$)$_2$$^+$, —S(CH$_2$CH$_3$)$_2$$^+$, —S(CH$_2$CH$_2$CH$_3$)$_2$$^+$, —SH(cyclopentyl)$^+$, and —SH(cyclohexyl)$^+$. The term "substituted alkylsulfonium" refers to the group —SRR'$^+$, in which R and R' can be the same or different substituted alkyl groups, one of R or R' is an alkyl and the other is a substituted alkyl, of R and R' can be taken together to represent a substituted alkanediyl. For example, —SH(CH$_2$CF$_3$)$^+$ is a substituted alkylsulfonium group.

The term "alkylsilyl," when used without the "substituted" modifier, refers to a monovalent group, defined as —SiH$_2$R, —SiHRR', or —SiRR'R'', in which R, R' and R'' can be the same or different alkyl groups, or any combination of two of R, R' and R'' can be taken together to represent an alkanediyl. The groups, —SiH$_2$CH$_3$, —SiH(CH$_3$)$_2$, —Si(CH$_3$)$_3$ and —Si(CH$_3$)$_2$C(CH$_3$)$_3$, are non-limiting examples of unsubstituted alkylsilyl groups. The term "substituted alkylsilyl" refers —SiH$_2$R, —SiHRR', or —SiRR'R'', in which at least one of R, R' and R'' is a substituted alkyl or two of R, R' and R'' can be taken together to represent a substituted alkanediyl. When more than one of R, R' and R" is a substituted alkyl, they can be the same of different. Any of R, R' and R" that are not either substituted alkyl or substituted alkanediyl, can be either alkyl, either the same or different, or can be taken together to represent an alkanediyl with two or more saturated carbon atoms, at least two of which are attached to the silicon atom.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

A compound having a formula that is represented with a dashed bond is intended to include the formulae optionally having zero, one or more double bonds. Thus, for example, the structure

includes the structures

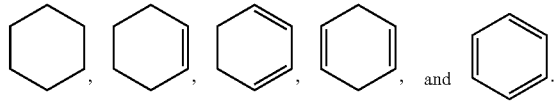

As will be understood by a person of skill in the art, no one such ring atom forms part of more than one double bond.

Any undefined valency on an atom of a structure shown in this application implicitly represents a hydrogen atom bonded to the atom.

A ring structure shown with an unconnected "R" group, indicates that any implicit hydrogen atom on that ring can be replaced with that R group. In the case of a divalent R group (e.g., oxo, imino, thio, alkylidene, etc.), any pair of implicit hydrogen atoms attached to one atom of that ring can be replaced by that R group. This concept is as exemplified by:

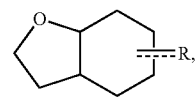

which represents

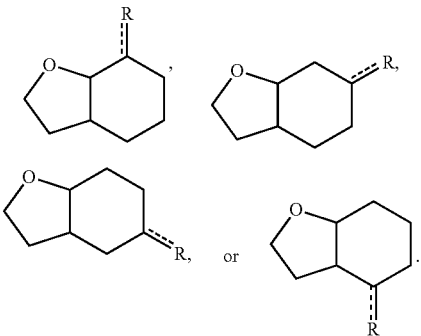

As used herein, a "chiral auxiliary" refers to a removable chiral group that is capable of influencing the stereoselectivity of a reaction. Persons of skill in the art are familiar with such compounds, and many are commercially available.

Non-limiting examples of compounds provided by this invention include the compounds according to the formulae shown below, as well as or pharmaceutically acceptable salts, hydrates, solvates, tautomers, or optical isomers thereof.

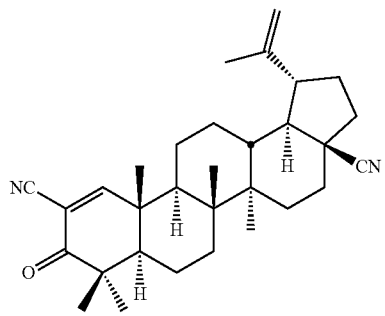

TP-342

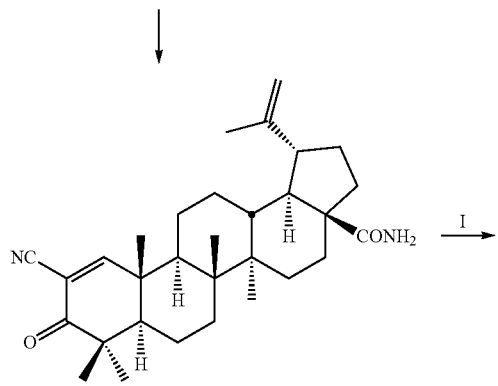

I →

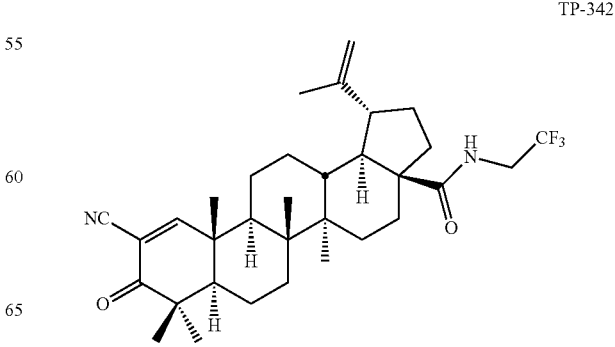

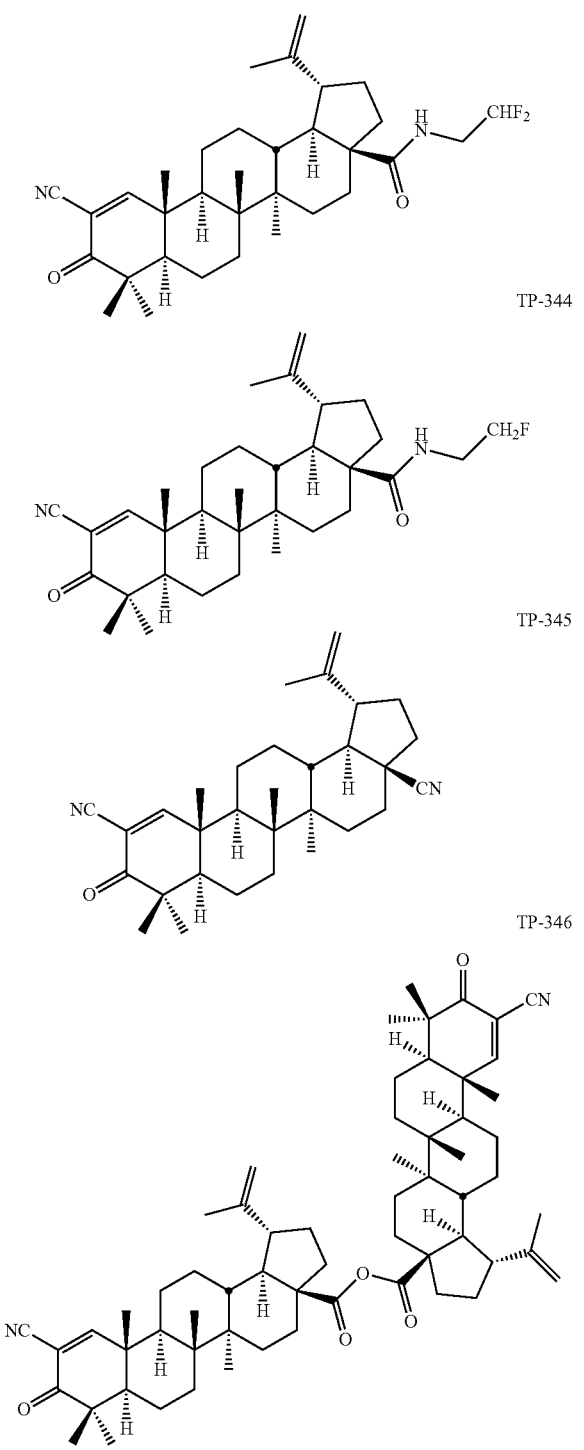

The term "hydrate," when used as a modifier to a compound, means that the compound has less than one (e.g., hemihydrate), one (e.g., monohydrate), or more than one (e.g., dehydrate) water molecules associated with each compound molecule, such as in solid forms of the compound.

In some embodiments, the compounds of the present invention are in the form of pharmaceutically acceptable salts. In other embodiments, the compounds are not salts. "Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylicacids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002).

In some embodiments, the compounds of the present invention are present as a mixture of stereoisomers. In other embodiments, the compounds are predominantly present as a single stereoisomer. An "isomer" of a first compound is a separate compound in which each molecule contains the same constituent atoms as the first compound, but where the configuration of those atoms in three dimensions differs. In particular embodiments, these compounds are substantially free from other optical isomers thereof. A "stereoisomer" or "optical isomer" is an isomer of a given compound in which the same atoms are bonded to the same other atoms, but where the configuration of those atoms in three dimensions differs. As used herein, "predominantly one enantiomer" means that a compound contains at least about 85% of one enantiomer, or more preferably at least about 90% of one enantiomer, or even more preferably at least about 95% of one enantiomer, or most preferably at least about 99% of one enantiomer. Similarly, the phrase "substantially free from other optical isomers" means that the composition contains at most about 15% of another enantiomer or diastereomer, more preferably at most about 10% of another enantiomer or diastereomer, even more preferably at most about 5% of another enantiomer or diastereomer, and most preferably at most about 1% of another enantiomer or diastereomer. "Enantiomers" are stereoisomers of a given compound that are mirror images of each other, like left and right hands. "Diastereomers" are stereoisomers of a given compound that are not enantiomers.

In some embodiments, the compounds of the present invention are effective for inhibiting IFN-γ-induced NO production in macrophages, further wherein the compound has an $IC_{50}$ value of less than 0.2 μM. As used herein, the term "$IC_{50}$" refers to an inhibitory dose which is 50% of the maximum response obtained.

Prodrugs are also embraced by this invention, where "prodrug" means a compound that is convertible in vivo metabolically into an inhibitor according to the present invention. The prodrug itself may or may not also have activity with respect to a given target protein. For example, a compound including a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methane-sulfonates, ethanesulfonates, benzenesulfonates, p-toluenesulfonates, cyclohexyl-sulfamates, quinates, esters of amino acids, and the like. Similarly, a compound comprising an amine group may be administered as an amide that is converted by hydrolysis in vivo to the amine compound.

In some embodiments, the invention provides compounds selected from the group of:

(1R,3aS,5aR,5bR,7aR,11aR,13aR,13bR)-10-cyano-5a,5b,8,8,11a-pentamethyl-9-oxo-1-(prop-1-en-2-yl)-N-(2,2,2-trifluoroethyl)-2,3,3a,4,5,5a,5b,6,7,7a,8,9,11a,11b,12,13,13a,13b-octadecahydro-1H-cyclopenta[a]chrysene-3a-carboxamide;

(1R,3aS,5aR,5bR,7aR,11aR,13aR,13bR)-10-cyano-N-(2,2-difluoroethyl)-5a,5b,8,8,11a-pentamethyl-9-oxo-1-(prop-1-en-2-yl)-2,3,3a,4,5,5a,5b,6,7,7a,8,9,11a,11b,12,13,13a,13b-octadecahydro-1H-cyclopenta[a]chrysene-3a-carboxamide;

(1R,3aS,5aR,5bR,7aR,11aR,13aR,13bR)-10-cyano-N-(2-fluoroethyl)-5a,5b,8,8,11a-pentamethyl-9-oxo-1-(prop-1-en-2-yl)-2,3,3a,4,5,5a,5b,6,7,7a,8,9,11a,11b,12,13,13a,13b-octadecahydro-1H-cyclopenta[a]chrysene-3a-carboxamide;

(1R,3aS,5aR,5bR,7aR,11aR,13aR,13bR)-5a,5b,8,8,11a-pentamethyl-9-oxo-1-(prop-1-en-2-yl)-2,3,3a,4,5,5a,5b,6,7,7a,8,9,11a,11b,12,13,13a,13b-octadecahydro-1H-cyclopenta[a]chrysene-3a,10-dicarbonitrile; and (1R,3aS,5aR,5bR,7aR,11aR,13aR,13bR)-10-cyano-5a,5b,8,8,11a-pentamethyl-9-oxo-1-(prop-1-en-2-yl)-2,3,3a,4,5,5a,5b,6,7,7a,8,9,11a,11b,12,13,13a,13b-octadecahydro-1H-cyclopenta[a]chrysene-3a-carboxylic anhydride.

The compounds of the present invention were made using the synthetic methods outlined below in Schemes 1 and 2 and in Examples 1-4. Additional compounds of this invention, such as those contemplated by the generic formulas, can be synthesized according to the methods taught herein and as taught in Honda, et al. (2006) supra and Liby et al. (2007) supra. These methods can be further modified and optimized using the principles and techniques of organic chemistry as applied by a person skilled in the art. Such principles and techniques are taught, for example, in March's Advanced Organic Chemistry: Reactions Mechanisms and Structure (March's Advanced Organic Chemistry), Smith & March (Eds.) 2007.

SCHEME 1

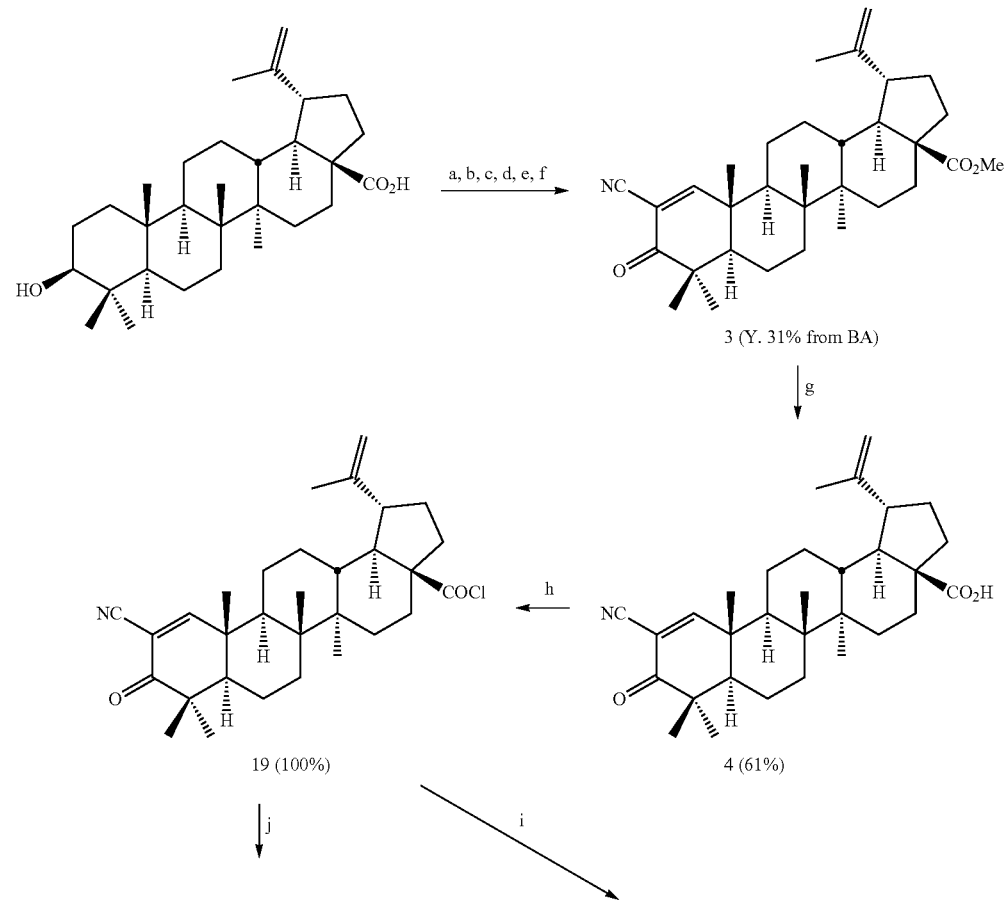

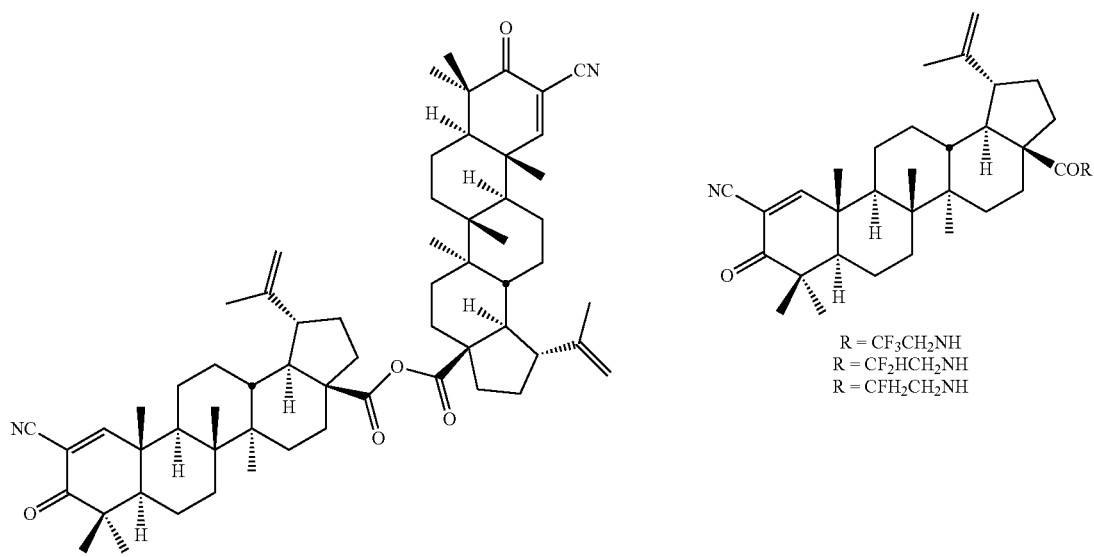
(a) CH₂N₂, THF; (b) Jone's; (c) HCO₂Et, NaOMe, PhH; (d) NH₂OH·HCl, EtOH; (e) NaOMe, MeOH, Et₂O; (f) DDQ, PhH; (g) AlCl₃, Me₂S; (h) (COCl)₂, CH₂Cl₂; (i) RNH₂, NaHCO₃ PhH (reflux) or RNH₂·HCl, NaHCO₃, water, PhH (reflux); (j) n-BuLi, ZnCl₂, N-methylimidazole, THF.
SCHEME 2
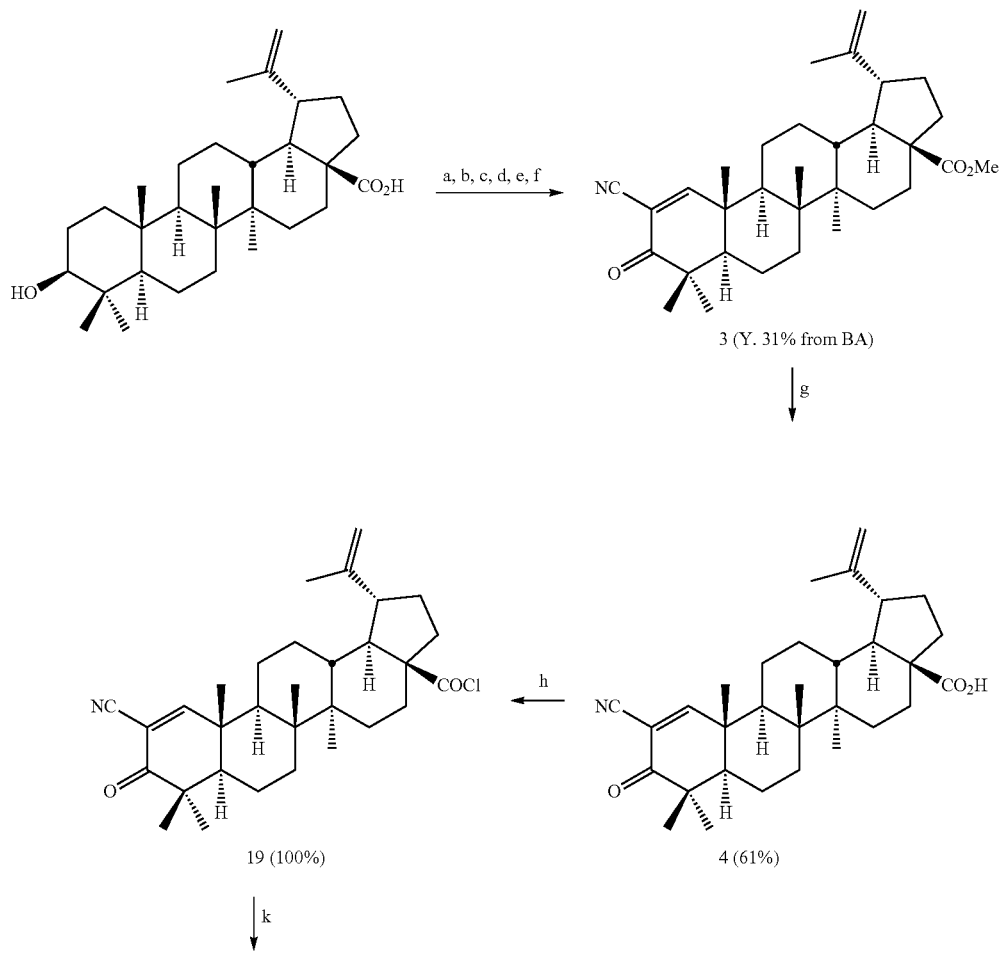

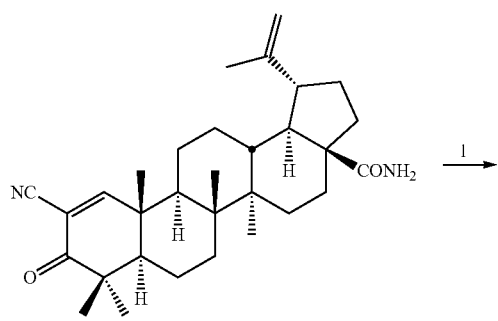 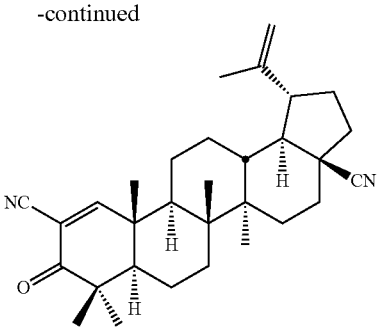

(a) CH₂N₂, THF; (b) Jone's; (c) HCO₂Et, NaOMe, PhH; (d) NH₂OH· HCl, EtOH; (e) NaOMe, MeOH, Et₂O; (f) DDQ, PhH; (g) AlCl₃, Me₂S; (h) (COCl)₂, CH₂Cl₂; (k) NH₃, PhH; (l) SOCl₂.

The data presented herein demonstrate that compounds of the present invention can effectively inhibit nitric oxide production. Accordingly, the present invention embraces the use of the compounds disclosed herein for preventing or treating a disease associated with inflammation and/or oxidative stress. As is conventional in the art, inflammation is a biological process that provides resistance to infectious or parasitic organisms and the repair of damaged tissue. Inflammation is commonly characterized by localized vasodilation, redness, swelling, and pain, the recruitment of leukocytes to the site of infection or injury, production of inflammatory cytokines such as TNF-α and IL-1, and production of reactive oxygen or nitrogen species such as hydrogen peroxide, superoxide and peroxynitrite. In later stages of inflammation, tissue remodeling, angiogenesis, and scar formation (fibrosis) may occur as part of the wound healing process. Under normal circumstances, the inflammatory response is regulated and temporary, and is resolved in an orchestrated fashion once the infection or injury has been dealt with adequately. However, acute inflammation can become excessive and life-threatening if regulatory mechanisms fail. Alternatively, inflammation can become chronic and cause cumulative tissue damage or systemic complications.

Many serious and intractable human diseases involve dysregulation of inflammatory processes, including diseases such as cancer, atherosclerosis, and diabetes, which were not traditionally viewed as inflammatory conditions. In the case of cancer, the inflammatory processes are associated with tumor formation, progression, metastasis, and resistance to therapy. Atherosclerosis, long viewed as a disorder of lipid metabolism, is now understood to be primarily an inflammatory condition, with activated macrophages playing an important role in the formation and eventual rupture of atherosclerotic plaques. Activation of inflammatory signaling pathways has also been shown to play a role in the development of insulin resistance, as well as in the peripheral tissue damage associated with diabetic hyperglycemia. Excessive production of reactive oxygen species and reactive nitrogen species such as superoxide, hydrogen peroxide, nitric oxide, and peroxynitrite is a hallmark of inflammatory conditions. Evidence of dysregulated peroxynitrite production has been reported in a wide variety of diseases (Szabo, et al. (2007) Nature Rev. Drug Disc. 6:662-680; Schulz, et al. (2008) Antioxid. Redox. Sig. 10:115; Forstermann (2006) Biol. Chem. 387:1521; Pall (2007) Med. Hypoth. 69:821-825).

Autoimmune diseases such as rheumatoid arthritis, lupus, psoriasis, and multiple sclerosis involve inappropriate and chronic activation of inflammatory processes in affected tissues, arising from dysfunction of self vs. non-self recognition and response mechanisms in the immune system. In neurodegenerative diseases such as Alzheimer's and Parkinson's diseases, neural damage is correlated with activation of microglia and elevated levels of pro-inflammatory proteins such as inducible nitric oxide synthase (iNOS). Chronic organ failure such as renal failure, heart failure, and chronic obstructive pulmonary disease is closely associated with the presence of chronic oxidative stress and inflammation, leading to the development of fibrosis and eventual loss of organ function.

Many other disorders involve oxidative stress and inflammation in affected tissues, including inflammatory bowel disease; inflammatory skin diseases; mucositis related to radiation therapy and chemotherapy; eye diseases such as uveitis, glaucoma, macular degeneration, and various forms of retinopathy; transplant failure and rejection; ischemia-reperfusion injury; chronic pain; degenerative conditions of the bones and joints including osteoarthritis and osteoporosis; asthma and cystic fibrosis; seizure disorders; and neuropsychiatric conditions including schizophrenia, depression, bipolar disorder, post-traumatic stress disorder, attention deficit disorders, autism-spectrum disorders, and eating disorders such as anorexia nervosa. Dysregulation of inflammatory signaling pathways is believed to be a major factor in the pathology of muscle wasting diseases including muscular dystrophy and various forms of cachexia.

A variety of life-threatening acute disorders also involve dysregulated inflammatory signaling, including acute organ failure involving the pancreas, kidneys, liver, or lungs, myocardial infarction or acute coronary syndrome, stroke, septic shock, trauma, severe burns, and anaphylaxis.

Many complications of infectious diseases also involve dysregulation of inflammatory responses. Although an inflammatory response can kill invading pathogens, an excessive inflammatory response can also be quite destructive and in some cases can be a primary source of damage in infected tissues. Furthermore, an excessive inflammatory response can also lead to systemic complications due to overproduction of inflammatory cytokines such as TNF-α and IL-1. This is believed to be a factor in mortality arising from severe influenza, severe acute respiratory syndrome, and sepsis.

The aberrant or excessive expression of either iNOS or cyclooxygenase-2 (COX-2) has been implicated in the pathogenesis of many disease processes. For example, it is clear that NO is a potent mutagen (Tamir & Tannebaum (1996) Biochim. Biophys. Acta. 1288:F31-F36), and that nitric oxide can also activate COX-2 (Salvemini, et al. (1994) J. Clin. Invest. 93:1940-1947). Furthermore, there is a marked increase in iNOS in rat colon tumors induced by the carcinogen, azoxymethane (Takahashi, et al. (1997) Cancer Res. 57:1233-1237). A series of synthetic triterpenoid analogs of oleanolic acid have been shown to be powerful inhibitors of cellular inflammatory processes, such as the induction by IFN-γ of inducible nitric oxide synthase (iNOS) and of COX-2 in mouse macrophages. See, Honda, et al. (2000) *J. Med. Chem.* 43:1866-1877; Honda, et al. (2000) *J. Med. Chem.* 43:4233-4246 and Honda, et al. (2002) *Bioorg. Med. Chem. Lett.* 12:1027-1030.

In one aspect, compounds of the invention are characterized by their ability to inhibit the production of nitric oxide in macrophage-derived RAW 264.7 cells induced by exposure to γ-interferon. They are further characterized by their ability to induce the expression of antioxidant proteins such as NQO1 and reduce the expression of pro-inflammatory proteins such as COX-2 and inducible nitric oxide synthase (iNOS). These properties are relevant to the treatment of a wide array of diseases involving oxidative stress and dysregulation of inflammatory processes including cancer, mucositis resulting from radiation therapy or chemotherapy, autoimmune diseases, cardiovascular diseases, ischemia-reperfusion injury, acute and chronic organ failure including renal failure and heart failure, respiratory diseases, diabetes and complications of diabetes, severe allergies, transplant rejection, graft-versus-host disease, neurodegenerative diseases, diseases of the eye and retina, acute and chronic pain, degenerative bone diseases including osteoarthritis and osteoporosis, inflammatory bowel diseases, dermatitis and other skin diseases, cardiovascular diseases including atherosclerosis, sepsis, burns, seizure disorders, and neuropsychiatric disorders.

Without being bound by theory, the activation of the anti-oxidant/anti-inflammatory Keap1/Nrf2/ARE pathway is believed to be implicated in both the anti-inflammatory and anti-carcinogenic properties of the present betulinic acid derivatives.

In another aspect, compounds of the invention find application in treating a subject having a condition caused by elevated levels of oxidative stress in one or more tissues. Oxidative stress results from abnormally high or prolonged levels of reactive oxygen species such as superoxide, hydrogen peroxide, nitric oxide, and peroxynitrite (formed by the reaction of nitric oxide and superoxide). The oxidative stress may be accompanied by either acute or chronic inflammation. The oxidative stress may be caused by mitochondrial dysfunction, by activation of immune cells such as macrophages and neutrophils, by acute exposure to an external agent such as ionizing radiation or a cytotoxic chemotherapy agent (e.g., doxorubicin), by trauma or other acute tissue injury, by ischemia/reperfusion, by poor circulation or anemia, by localized or systemic hypoxia or hyperoxia, by elevated levels of inflammatory cytokines and other inflammation-related proteins, and/or by other abnormal physiological states such as hyperglycemia or hypoglycemia.

In animal models of many such conditions, stimulating expression of inducible heme oxygenase (HO-1), a target gene of the Nrf2 pathway, has been shown to have a significant therapeutic effect including models of myocardial infarction, renal failure, transplant failure and rejection, stroke, cardiovascular disease, and autoimmune disease (e.g., Sacerdoti, et al. (2005) *Curr Neurovasc Res.* 2(2):103-111; Abraham & Kappas (2005) *Free Radic. Biol. Med.* 39(1):1-25; Bach (2006) *Hum. Immunol.* 67(6):430-432; Araujo, et al. (2003) *J. Immunol.* 171(3):1572-1580; Liu, et al. (2006) *FASEB J.* 20(2):207-216; Ishikawa, et al. (2001) *Circulation* 104(15):1831-1836; Kruger, et al. (2006) *J. Pharmacol. Exp. Ther.* 319(3):1144-1152; Satoh, et al. (2006) *Proc. Natl. Acad. Sci. USA* 103(3):768-773; Zhou, et al. (2005) *Am. J. Pathol.* 166(1):27-37; Morse & Choi (2005) *Am. J. Respir. Crit. Care Med.* 172(6):660-670; Morse & Choi (2002) *Am. J. Respir. Crit. Care Med.* 27(1):8-16). This enzyme breaks free heme down into iron, carbon monoxide (CO), and biliverdin (which is subsequently converted to the potent antioxidant molecule, bilirubin).

In another aspect, compounds of this invention may be used in preventing or treating tissue damage or organ failure, acute and chronic, resulting from oxidative stress exacerbated by inflammation. Examples of diseases that fall in this category include: heart failure, liver failure, transplant failure and rejection, renal failure, pancreatitis, fibrotic lung diseases (cystic fibrosis and COPD, among others), diabetes (including complications), atherosclerosis, ischemia-reperfusion injury, glaucoma, stroke, autoimmune disease, autism, macular degeneration, and muscular dystrophy. For example, in the case of autism, studies suggest that increased oxidative stress in the central nervous system may contribute to the development of the disease (Chauhan & Chauhan (2006) *Pathophysiology* 13(3):171-181).

Evidence also links oxidative stress and inflammation to the development and pathology of many other disorders of the central nervous system, including psychiatric disorders such as psychosis, major depression, and bipolar disorder; seizure disorders such as epilepsy; pain and sensory syndromes such as migraine, neuropathic pain or tinnitus; and behavioral syndromes such as the attention deficit disorders. See, e.g., Dickerson, et al. (2007) *Prog Neuropsychopharmacol Biol. Psychiatry* March 6; Hanson, et al. (2005) *BMC Medical Genetics* 6(7); Kendall-Tackett (2007) *Trauma Violence Abuse* 8(2):117-126; Lencz, et al. (2007) *Mol. Psychiatry* 12(6):572-80; Dudhgaonkar, et al. (2006) *Eur. J. Pain* 10(7): 573-9; Lee, et al. (2007) *Glia.* 55(7):712-22; Morris, et al. (2002) *J. Mol. Med.* 80(2):96-104; Ruster, et al. (2005) *Scand. J. Rheumatol.* 34(6):460-3; McIver, et al. (2005) *Pain* 120(1-2):161-9; Sarchielli, et al. (2006) *Cephalalgia* 26(9):1071-1079; Kawakami, et al. (2006) *Brain Dev.* 28(4):243-246; Ross, et al. (2003) *Nutr. Neurosci.* 6(5):277-81. For example, elevated levels of inflammatory cytokines, including TNF, interferon-γ, and IL-6, are associated with major mental illness (Dickerson, et al. (2007) supra). Microglial activation has also been linked to major mental illness. Therefore, downregulating inflammatory cytokines and inhibiting excessive activation of microglia could be beneficial in patients with schizophrenia, major depression, bipolar disorder, autism-spectrum disorders, and other neuropsychiatric disorders.

Accordingly, in pathologies involving oxidative stress alone or oxidative stress exacerbated by inflammation, treatment can include administering to a subject a therapeutically effective amount of a compound of this invention, such as those described throughout this specification. Treatment may be administered preventively, in advance of a predictable state of oxidative stress (e.g., organ transplantation or the administration of radiation therapy to a cancer patient), or it may be administered therapeutically in settings involving established oxidative stress and inflammation.

The compounds of the invention may be generally applied to the treatment of inflammatory conditions, such as sepsis, dermatitis, autoimmune disease and osteoarthritis. In one aspect, the compounds of this invention may be used to treat inflammatory pain and/or neuropathic pain, for example, by inducing Nrf2 and/or inhibiting NF-κB.

In one embodiment, the compounds of the invention may be used to function as antioxidant inflammation modulators (AIMs) having potent anti-inflammatory properties that mimic the biological activity of cyclopentenone prostaglandins (cyPGs). In certain embodiments, the compounds of the invention may be used to control the production of pro-inflammatory cytokines by selectively targeting regulatory cysteine residues (RCRs) on proteins that regulate the transcriptional activity of redox-sensitive transcription factors. Activation of RCRs by cyPGs or AIMs has been shown to initiate a pro-resolution program in which the activity of the antioxidant and cytoprotective transcription factor Nrf2 is potently induced, and the activities of the pro-oxidant and pro-inflammatory transcription factors NF-□B and the STATs are suppressed. This increases the production of antioxidant and reductive molecules (e.g., NQO1, HO-1, SOD1, and/or γ-GCS) and/or decreases oxidative stress and the production of pro-oxidant and pro-inflammatory molecules (e.g., iNOS, COX-2, and/or TNF-α).

In some embodiments, the compounds of the invention may be used in the treatment and prevention of diseases such as cancer, inflammation, Alzheimer's disease, Parkinson's disease, multiple sclerosis, autism, amyotrophic lateral sclerosis, autoimmune diseases such as rheumatoid arthritis, lupus, and MS, inflammatory bowel disease, all other diseases whose pathogenesis is believed to involve excessive production of either nitric oxide or prostaglandins, and pathologies involving oxidative stress alone or oxidative stress exacerbated by inflammation.

Another aspect of inflammation is the production of inflammatory prostaglandins such as prostaglandin E. These molecules promote vasodilation, plasma extravasation, localized pain, elevated temperature, and other symptoms of inflammation. The inducible form of the enzyme COX-2 is associated with their production, and high levels of COX-2 are found in inflamed tissues. Consequently, inhibition of COX-2 may relieve many symptoms of inflammation and a number of important anti-inflammatory drugs (e.g., ibuprofen and celecoxib) act by inhibiting COX-2 activity. Research, however, has demonstrated that a class of cyclopentenone prostaglandins (cyPGs) (e.g., 15-deoxy prostaglandin J2, a.k.a. PGJ2) plays a role in stimulating the orchestrated resolution of inflammation. COX-2 is also associated with the production of cyclopentenone prostaglandins. Consequently, inhibition of COX-2 may interfere with the full resolution of inflammation, potentially promoting the persistence of activated immune cells in tissues and leading to chronic, "smoldering" inflammation. This effect may be responsible for the increased incidence of cardiovascular disease in patients using selective COX-2 inhibitors for long periods of time.

In one aspect, the compounds of the invention may be used to control the production of pro-inflammatory cytokines within the cell by selectively activating regulatory cysteine residues (RCRs) on proteins that regulate the activity of redox-sensitive transcription factors. Activation of RCRs by cyPGs has been shown to initiate a pro-resolution program in which the activity of the antioxidant and cytoprotective transcription factor Nrf2 is potently induced and the activities of the pro-oxidant and pro-inflammatory transcription factors NF-κB and the STATs are suppressed. In some embodiments, this increases the production of antioxidant and reductive molecules (NQO1, HO-1, SOD1, γ-GCS) and decreases oxidative stress and the production of pro-oxidant and pro-inflammatory molecules (iNOS, COX-2, TNF-α). In some embodiments, the compounds of this invention may cause the cells that host the inflammatory event to revert to a non-inflammatory state by promoting the resolution of inflammation and limits excessive tissue damage to the host.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject of patient which may be at risk and/or predisposed to the disease but does not yet experience or display any or all of the pathology or symptomatology of the disease.

Cancer. Further, the compounds of the present invention may be used to induce apoptosis in tumor cells, to induce cell differentiation, to inhibit cancer cell proliferation, to inhibit an inflammatory response, and/or to function in a chemopreventative capacity. For example, the invention provides new compounds that have one or more of the following properties: (1) an ability to induce apoptosis and differentiate both malignant and non-malignant cells, (2) an activity at sub-micromolar or nanomolar levels as an inhibitor of proliferation of many malignant or premalignant cells, (3) an ability to suppress the de novo synthesis of the inflammatory enzyme inducible nitric oxide synthase (iNOS), (4) an ability to inhibit NF-κB activation, and (5) an ability to induce the expression of heme oxygenase-1 (HO-1).

The levels of iNOS and COX-2 are elevated in certain cancers and have been implicated in carcinogenesis and COX-2 inhibitors have been shown to reduce the incidence of primary colonic adenomas in humans (Rostom, et al. (2007) *Ann. Intern. Med.* 146 376-389; Brown & DuBois (2005) *J. Clin. Oncol.* 23:2840-2855; Crowel, et al. (2003) *Mol. Cancer Ther.* 2:815-823). iNOS is expressed in myeloid-derived tumor suppressor cells (MDSCs) (Angulo, et al. (2000) *Eur. J. Immunol.* 30:1263-1271) and COX-2 activity in cancer cells has been shown to result in the production of prostaglandin $E_2$ ($PGE_2$), which has been shown to induce the expression of arginase in MDSCs (Sinha, et al. (2007) *Cancer Res.* 67:4507-4513). Arginase and iNOS are enzymes that utilize L-arginine as a substrate and produce L-ornithine and urea, and L-citrulline and NO, respectively. The depletion of arginine from the tumor microenvironment by MDSCs, combined with the production of NO and peroxynitrite has been shown to inhibit proliferation and induce apoptosis of T cells (Bronte, et al. (2003) *J. Immunol.* 70(1):270-8). Inhibition of COX-2 and iNOS has been shown to reduce the accumulation of MDSCs, restore cytotoxic activity of tumor-associated T cells, and delay tumor growth (Sinha, et al. (2007) supra; Mazzoni, et al. (2002) *J. Immunol.* 168:689-695; Zhou, et al. (2007) *Cancer Sci.* 98:882-889).

Inhibition of the NF-κB and JAK/STAT signaling pathways has been implicated as a strategy to inhibit proliferation of cancer epithelial cells and induce their apoptosis. Activation of STAT3 and NF-κB has been shown to result in suppression of apoptosis in cancer cells, and promotion of proliferation, invasion, and metastasis. Many of the target genes involved in these processes have been shown to be transcriptionally regulated by both NF-κB and STAT3 (Yu, et al. (2007) *Nat. Rev. Immunol.* 7:41-51).

In addition to their direct roles in cancer epithelial cells, NF-κB and STAT3 also have important roles in other cells found within the tumor microenvironment. Experiments in animal models have demonstrated that NF-κB is required in both cancer cells and hematopoeitic cells to propagate the effects of inflammation on cancer initiation and progression (Greten, et al. (2004) *Cell* 118:285-296). NF-κB inhibition in cancer and myeloid cells reduces the number and size, respectively, of the resultant tumors. Activation of STAT3 in cancer cells results in the production of several cytokines (IL-6, IL-10) which suppress the maturation of tumor-associated dendritic cells. Furthermore, STAT3 is activated by these cytokines in the dendritic cells themselves. Inhibition of STAT3 in mouse models of cancer restores DC maturation, promotes antitumor immunity, and inhibits tumor growth (Kortylewski, et al. (2005) *Nat. Med.* 11:1314-1321).

Treatment of Multiple Sclerosis and Other Neurodegenerative Conditions. The compounds and methods of this invention may be used for treating patients for multiple sclerosis (MS). The use of one or more of the compounds of the present invention as improved candidates for treatment for of MS and other neurodegenerative diseases results at least in part due to the expected ability of one or more of the compounds of the present invention to penetrate the blood-brain barrier. For example, TP-342 is expected to achieve a higher concentration in the brain than TP-321 based on experienced gained comparing the tissue distribution of two oleanolic acid derivatives that vary structurally in a similar manner. Compare TP-319 (CDDO-EA) and TP-500 (CDDO-TFEA).

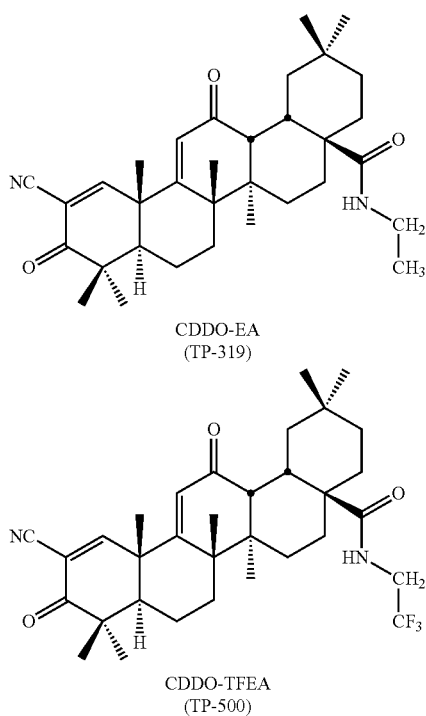

CDDO-EA
(TP-319)

CDDO-TFEA
(TP-500)

Figure 2:
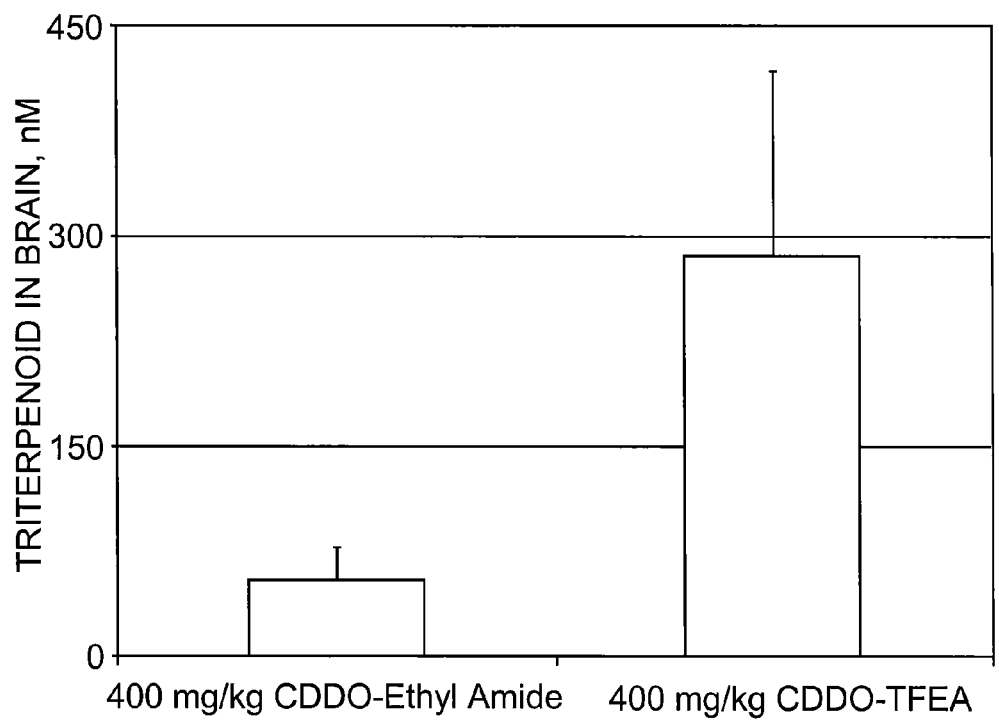
FIG. 2 shows that CDDO-TFEA (TP-500) is detected at higher levels in mouse brain compared to CDDO-EA (TP-319). CD-1 mice were fed either 200 or 400 mg/kg diet of either TP-319 or TP-500 for 3.5 days, and TP levels in the brains of the mice were analyzed by LC/MS. The structures of TP-319 and TP-500 are provided herein.

As shown in FIG. 2, TP-500 is able to achieve a significantly higher concentration in the brain than TP-319. A similar effect is expected for TP-342. Further details on these experiments may be found in U.S. Provisional Application No. 60/916,273 and U.S. Ser. No. 12/151,425.

Multiple sclerosis (MS) is known to be an inflammatory condition of the central nervous system (Williams, et al. (1994) *Clin. Neurosci.* 2(3-4):229-245; Merrill & Benvenist (1996) *Trends Neurosci.* 19:331-338; Genain & Nauser (1997) *J. Mol. Med.* 75:187-197). In general, inflammatory, oxidative, or immune mechanisms may be involved in the pathogenesis of Alzheimer's disease (AD), Parkinson's disease (PD), amyotrophic lateral sclerosis (ALS), and MS (Bagasra, et al. (1995) *Proc. Natl. Acad. Sci. USA* 92:12041-12045; McGeer & McGeer (1995) *Brain Res. Brain Res. Rev.* 21:195-218; Simonian & Coyle (1996) *Annu. Rev. Pharmacol. Toxicol.* 36:83-106; Kaltschmidt, et al. (1997) *Proc. Natl. Acad. Sci. USA* 94:2642-2647). Both reactive astrocytes and activated microglia have been implicated in causation of neurodegenerative disease (NDD) and neuroinflammatory disease (NID); there has been a particular emphasis on microglia as cells that synthesize both NO and prostaglandins as products of the respective enzymes, iNOS and COX-2. De novo formation of these enzymes may be driven by inflammatory cytokines such as interferon-γ or interleukin-1. In turn, excessive production of NO may lead to inflammatory cascades and/or oxidative damage in cells and tissues of many organs, including neurons and oligodendrocytes of the nervous system, with consequent manifestations in AD and MS, and possible PD and ALS (Coyle & Puttfarcken (1993) *Science* 262:689-695; Beal (1996) *Curr. Opin. Neurobiol.* 6:661-666; Merrill & Benvenist (1996) supra; Simonian & Coyle (1996) supra; Vodovotz, et al. (1996) In; *Handbook of Experimental Immunology* Volumes I-IV). Epidemiologic data indicate that chronic use of NSAID's which block synthesis of prostaglandins from arachidonate, markedly lower the risk for development of AD (McGeer, et al. (1996) *Neurology* 19:331-338; Stewart, et al. (1997) *Neurology* 48:626-632). Thus, agents that block formation of NO and prostaglandins, may be used in approaches to prevention and treatment of NDD.

Neuroinflammation. The compounds and methods of this invention may be used for treating patients with neuroinflammation. Neuroinflammation encapsulates the idea that microglial and astrocytic responses and actions in the central nervous system have a fundamentally inflammation-like character, and that these responses are central to the pathogenesis and progression of a wide variety of neurological disorders. This idea originated in the field of Alzheimer's disease (Griffin, et al. (1989) *Proc. Natl. Acad. Sci. USA* 86(19):7611-7615; Rogers, et al. (1988) *Neurobiol Aging* 9(4):339-349), where it has revolutionized our understanding of this disease (Akiyama, et al. (2000) *Alzheimer Dis. Assoc. Disord.* 14(1):S47-53). These ideas have been extended to other neurodegenerative diseases (Eikelenboom, et al. (2002) *Glia* 40(2):232-239; Ishizawa & Dickson (2001) *J. Neuropathol. Exp. Neurol.* 60(6):647-657), to ischemic/toxic diseases (Gehrmann, et al. (1995) *Glia* 15(2):141-151; Touzani, et al. (1999) *J. Neuroimmunol.* 100(1-2):203-215), to tumor biology (Graeber, et al. (2002) *Glia* 40(2):252-259) and even to normal brain development.

Neuroinflammation incorporates a wide spectrum of complex cellular responses that include activation of microglia and astrocytes and induction of cytokines, chemokines, complement proteins, acute phase proteins, oxidative injury, and related molecular processes. These events may have detrimental effects on neuronal function, leading to neuronal injury, further glial activation, and ultimately neurodegeneration.

Treatment of Renal Failure. The compounds and methods of this invention may be used for treating patients with renal failure. Thus, another aspect of the present invention concerns new methods and compounds for the treatment and prevention of renal disease. Renal failure, resulting in inadequate clearance of metabolic waste products from the blood and abnormal concentrations of electrolytes in the blood, is a significant medical problem throughout the world, especially in developed countries. Diabetes and hypertension are among the most important causes of chronic renal failure, also known as chronic kidney disease (CKD), but it is also associated with other conditions such as lupus. Acute renal failure may arise from exposure to certain drugs (e.g., acetaminophen) or toxic chemicals, or from ischemia-reperfusion injury associated with shock or surgical procedures such as transplantation, and may result in chronic renal failure. In many patients, renal failure advances to a stage in which the patient requires regular dialysis or kidney transplantation to continue living. Both of these procedures are highly invasive and associated with significant side effects and quality of life issues. Although there are effective treatments for some complications of renal failure, such as hyperparathyroidism and hyperphosphatemia, no available treatment has been shown to halt or reverse the underlying progression of renal failure. Thus, agents that can improve compromised renal function would represent a significant advance in the treatment of renal failure.

Inflammation contributes significantly to the pathology of CKD. There is also a strong mechanistic link between oxidative stress and renal dysfunction. The NF-κB signaling pathway plays an important role in the progression of CKD as NF-κB regulates the transcription of MCP-1, a chemokine that is responsible for the recruitment of monocytes/macrophages resulting in an inflammatory response that ultimately injures the kidney (Wardle (2001) *Nephrol. Dial. Transplant.* 16(9):1764-8). The Keap1/Nrf2/ARE pathway controls the transcription of several genes encoding antioxidant enzymes, including heme oxygenase-1 (HO-1). Ablation of the Nrf2 gene in female mice results in the development of lupus-like glomerular nephritis (Yoh, et al. (2001) *Kidney Int.* 60(4):1343-1353). Furthermore, several studies have demonstrated that HO-1 expression is induced in response to renal damage and inflammation and that this enzyme and its products—bilirubin and carbon monoxide— play a protective role in the kidney (Nath, et al. (2006) *Neurology* 66(1):149-150).

The glomerulus and the surrounding Bowman's capsule constitute the basic functional unit of the kidney. Glomerular filtration rate (GFR) is the standard measure of renal function. Creatinine clearance is commonly used to measure GFR. However, the level of serum creatinine is commonly used as a surrogate measure of creatinine clearance. For instance, excessive levels of serum creatinine are generally accepted to indicate inadequate renal function and reductions in serum creatinine over time are accepted as an indication of improved renal function. Normal levels of creatinine in the blood are approximately 0.6 to 1.2 milligrams (mg) per deciliter (dl) in adult males and 0.5 to 1.1 milligrams per deciliter in adult females.

Acute kidney injury (AKI) can occur following ischemia-reperfusion, treatment with certain pharmacological agents such as cisplatin and rapamycin, and intravenous injection of radiocontrast media used in medical imaging. As in CKD, inflammation and oxidative stress contribute to the pathology of AKI. The molecular mechanisms underlying radiocontrast-induced nephropathy (RCN) are not well understood; however, it is likely that a combination of events including prolonged vasoconstriction, impaired kidney autoregulation, and direct toxicity of the contrast media all contribute to renal failure (Tumlin, et al. (2006) *Am. J. Cardiol.* 98(6A):14K-20K). Vasoconstriction results in decreased renal blood flow and causes ischemia-reperfusion and the production of reactive oxygen species. HO-1 is strongly induced under these conditions and has been demonstrated to prevent ischemia-reperfusion injury in several different organs, including the kidney (Nath, et al. (2006) supra). Specifically, induction of HO-1 has been shown to be protective in a rat model of RCN (Goodman, et al. (2007) *Kidney Int.* 72(8):945-953). Reperfusion also induces an inflammatory response, in part though activation of NF-κB signaling (Nichols (2004) *Drug News Perspect.* 17(2):99-104). Targeting NF-κB has been proposed as a therapeutic strategy to prevent organ damage (Zingarelli, et al. (*J. Immunol.* 171(12):6827-68372003).

Cardiovascular Disease. The compounds and methods of this invention may be used for treating patients with cardiovascular disease. Cardiovascular (CV) disease is among the most important causes of mortality worldwide, and is the leading cause of death in many developed nations. The etiology of CV disease is complex, but the majority of causes are related to inadequate or completely disrupted supply of blood to a critical organ or tissue. Frequently such a condition arises from the rupture of one or more atherosclerotic plaques, which leads to the formation of a thrombus that blocks blood flow in a critical vessel. Such thrombosis is the principal cause of heart attacks, in which one or more of the coronary arteries is blocked and blood flow to the heart itself is disrupted. The resulting ischemia is highly damaging to cardiac tissue, both from lack of oxygen during the ischemic event and from excessive formation of free radicals after blood flow is restored (a phenomenon known as ischemia-reperfusion injury). Similar damage occurs in the brain during a thrombotic stroke, when a cerebral artery or other major vessel is blocked by thrombosis. Hemorrhagic strokes, in contrast, involve rupture of a blood vessel and bleeding into the surrounding brain tissue. This creates oxidative stress in the immediate area of the hemorrhage, due to the presence of large amounts of free heme and other reactive species, and ischemia in other parts of the brain due to compromised blood flow. Subarachnoid hemorrhage, which is frequently accompanied by cerebral vasospasm, also causes ischemia/reperfusion injury in the brain.

Alternatively, atherosclerosis may be so extensive in critical blood vessels that stenosis (narrowing of the arteries) develops and blood flow to critical organs (including the heart) is chronically insufficient. Such chronic ischemia can lead to end-organ damage of many kinds, including the cardiac hypertrophy associated with congestive heart failure.

Atherosclerosis, the underlying defect leading to many forms of cardiovascular disease, occurs when a physical defect or injury to the lining (endothelium) of an artery triggers an inflammatory response involving the proliferation of vascular smooth muscle cells and the infiltration of leukocytes into the affected area. Ultimately, a complicated lesion known as an atherosclerotic plaque may form, composed of the above-mentioned cells combined with deposits of cholesterol-bearing lipoproteins and other materials.

Pharmaceutical treatments for cardiovascular disease include preventive treatments, such as the use of drugs intended to lower blood pressure or circulating levels of cholesterol and lipoproteins, as well as treatments designed to reduce the adherent tendencies of platelets and other blood cells (thereby reducing the rate of plaque progression and the risk of thrombus formation). More recently, drugs such as streptokinase and tissue plasminogen activator have been introduced and are used to dissolve the thrombus and restore blood flow. Surgical treatments include coronary artery bypass graftng to create an alternative blood supply, balloon angioplasty to compress plaque tissue and increase the diameter of the arterial lumen, and carotid endarterectomy to remove plaque tissue in the carotid artery. Such treatments, especially balloon angioplasty, may be accompanied by the use of stents, expandable mesh tubes designed to support the artery walls in the affected area and keep the vessel open. Recently, the use of drug-eluting stents has become common in order to prevent post-surgical restenosis (renarrowing of the artery) in the affected area. These devices are wire stents coated with a biocompatible polymer matrix containing a drug that inhibits cell proliferation (e.g., paclitaxel or rapamycin). The polymer allows a slow, localized release of the drug in the affected area with minimal exposure of non-target tissues. Despite the significant benefits offered by such treatments, mortality from cardiovascular disease remains high and significant unmet needs in the treatment of cardiovascular disease remain.

As noted above, induction of HO-1 has been shown to be beneficial in a variety of models of cardiovascular disease, and low levels of HO-1 expression have been clinically correlated with elevated risk of CV disease. Compounds of the invention, therefore, may be used in treating or preventing a variety of cardiovascular disorders including but not limited to atherosclerosis, hypertension, myocardial infarction, chronic heart failure, stroke, subarachnoid hemorrhage, and restenosis.

Diabetes. The compounds and methods of this invention may be used for treating patients with diabetes. Diabetes is a complex disease characterized by the body's failure to regulate circulating levels of glucose. This failure may result from a lack of insulin, a peptide hormone that regulates both the production and absorption of glucose in various tissues. Deficient insulin compromises the ability of muscle, fat, and other tissues to absorb glucose properly, leading to hyperglycemia (abnormally high levels of glucose in the blood). Most commonly, such insulin deficiency results from inadequate production in the islet cells of the pancreas. In the majority of cases this arises from autoimmune destruction of these cells, a condition known as type 1 or juvenile-onset diabetes, but may also be due to physical trauma or some other cause.

Diabetes may also arise when muscle and fat cells become less responsive to insulin and do not absorb glucose properly, resulting in hyperglycemia. This phenomenon is known as insulin resistance, and the resulting condition is known as Type 2 diabetes. Type 2 diabetes, the most common type, is highly associated with obesity and hypertension.

Diabetes is associated with damage to many tissues, largely because hyperglycemia (and hypoglycemia, which can result from excessive or poorly timed doses of insulin) is a significant source of oxidative stress. Chronic kidney failure, retinopathy, peripheral neuropathy, peripheral vasculitis, and the development of dermal ulcers that heal slowly or not at all are among the common complications of diabetes. Because of their ability to protect against oxidative stress, particularly by the induction of HO-1 expression, compounds of the invention may be used in treatments for many complications of diabetes. As noted herein (Cai, et al. (2005) *Nat. Med.* 11(2):183-190), chronic inflammation and oxidative stress in the liver are suspected to be primary contributing factors in the development of Type 2 diabetes. Furthermore, PPARγ agonists such as thiazolidinediones are capable of reducing insulin resistance and are known to be effective treatments for Type 2 diabetes.

The effect of treatment of diabetes may be evaluated as follows. Both the biological efficacy of the treatment modality as well as the clinical efficacy are evaluated, if possible. For example, because the disease manifests itself by increased blood sugar, the biological efficacy of the treatment therefore can be evaluated, for example, by observation of return of the evaluated blood glucose towards normal. Measurement of glycosylated hemoglobin, also called A1c or HbA1c, is another commonly used parameter of blood glucose control. Measuring a clinical endpoint which can give an indication of β-cell regeneration after, for example, a six-month period of time, can give an indication of the clinical efficacy of the treatment regimen.

Rheumatoid Arthritis. The compounds and methods of this invention may be used for treating patients with rheumatoid arthritis (RA). Typically the first signs of RA appear in the synovial lining layer, with proliferation of synovial fibroblasts and their attachment to the articular surface at the joint margin (Lipsky (1998) In: *Harrison's principles of internal medicine* Fauci et al. (Eds.) 14th Ed. NY McGraw-Hill 1880-1888). Subsequently, macrophages, T cells and other inflammatory cells are recruited into the joint, where they produce a number of mediators, including the cytokines interleukin-1 (IL-1), which contributes to the chronic sequelae leading to bone and cartilage destruction, and tumor necrosis factor (TNF-α), which plays a role in inflammation (Dinarello (1998) *Int. Rev. Immunol.* 16:457-499; Arend & Dayer (1995) *Arthritis Rheum.* 38:151-160; van den Berg (2001) *Semin. Arthritis Rheum.* 30(5S-2):7-16). The concentration of IL-1 in plasma is significantly higher in patients with RA than in healthy individuals and, notably, plasma IL-1 levels correlate with RA disease activity (Eastgate, et al. (1988) *Lancet* 2:706-709). Moreover, synovial fluid levels of IL-1 are correlated with various radiographic and histologic features of RA (Kahle, et al. (1992) *Ann. Rheum. Dis.* 51:731-734; Rooney, et al. (1990) *Rheumatol. Int.* 10:217-219).

In normal joints, the effects of these and other proinflammatory cytokines are balanced by a variety of anti-inflammatory cytokines and regulatory factors (Burger & Dayer (1995) *Neurology* 45(6S-6):S39-43). The significance of this cytokine balance is illustrated in juvenile RA patients, who have cyclical increases in fever throughout the day (Prieur, et al. (1987) *Lancet.* 2:1240-1242). After each peak in fever, a factor that blocks the effects of IL-1 is found in serum and urine. This factor has been isolated, cloned and identified as IL-1 receptor antagonist (IL-1ra), a member of the IL-1 gene family (Hannum, et al. (1990) *Nature* 343:336-340). IL-1ra, as its name indicates, is a natural receptor antagonist that competes with IL-1 for binding to type I IL-1 receptors and, as a result, blocks the effects of IL-1 (Arend, et al. (1998) *Annu. Rev. Immunol.* 16:27-55). A 10- to 100-fold excess of IL-1ra may be needed to block IL-1 effectively; however, synovial cells isolated from patients with RA do not appear to produce enough IL-1ra to counteract the effects of IL-1 (Firestein, et al. (1994) *Arthritis Rheum.* 37:644-652; Fujikawa, et al. (1995) *Ann. Rheum. Dis.* 54:318-320).

Psoriatic Arthritis. The compounds and methods of this invention may also be used for treating patients with psoriatic arthritis. Psoriasis is an inflammatory and proliferative skin disorder with a prevalence of 1.5-3%. Approximately 20% of patients with psoriasis develop a characteristic form of arthritis that has several patterns (Gladman (1992) *Rheum. Dis. Clin. North Am.* 18:247-256; Jones, et al. (1994) *Br. J. Rheumatol.* 33(9):834-839; Gladman, et al. (1995) *Br. J. Rheumatol.* 22:675-679). Some individuals present with joint symptoms first but in the majority, skin psoriasis presents first. About one-third of patients have simultaneous exacerbations of their skin and joint disease (Gladman, et al. (1987) *J. Med.* 62:127-141) and there is a topographic relationship between nail and distal interphalangeal joint disease (Jones, et al. (1994) supra; Wright (1956) *Ann. Rheum. Dis.* 15:348-356). Although the inflammatory processes which link skin, nail and joint disease remain elusive, an immune-mediated pathology is implicated.

Psoriatic arthritis (PsA) is a chronic inflammatory arthropathy characterized by the association of arthritis and psoriasis and was recognized as a clinical entity distinct from rheumatoid arthritis (RA) in 1964 (Blumberg, et al. (1964)

*Arthritis Rheum.* 7:93-97). Subsequent studies have revealed that PsA shares a number of genetic, pathogenic and clinical features with other spondyloarthropathies (SpAs), a group of diseases that comprise ankylosing spondylitis, reactive arthritis and enteropathic arthritis (Wright (1979) *Clin. Orthop. Related Res.* 143:8-14). The notion that PsA belongs to the SpA group has recently gained further support from imaging studies demonstrating widespread enthesitis in the, including PsA but not RA (McGonagle, et al. (1999) *Curr. Opin. Rheumatol.* 11:244-250; McGonagle, et al. (1998) *Arthritis Rheum.* 41:694-700). More specifically, enthesitis has been postulated to be one of the earliest events occurring in the SpAs, leading to bone remodeling and ankylosis in the spine, as well as to articular synovitis when the inflamed entheses are close to peripheral joints. However, the link between enthesitis and the clinical manifestations in PsA remains largely unclear, as PsA can present with fairly heterogeneous patterns of joint involvement with variable degrees of severity (Marsal, et al. (1999) *Rheumatology* 38:332-337; Salvarani, et al. (1998) *Curr. Opin. Rheumatol.* 10:299-305). Thus, other factors must be posited to account for the multifarious features of PsA, only a few of which (such as the expression of the HLA-B27 molecule, which is strongly associated with axial disease) have been identified. As a consequence, it remains difficult to map the disease manifestations to specific pathogenic mechanisms, which means that the treatment of this condition remains largely empirical.

Family studies have suggested a genetic contribution to the development of PsA (Moll & Wright (1973) Ann. Rheum. Dis. 32:181-201). Other chronic inflammatory forms of arthritis, such as ankylosing spondylitis and rheumatoid arthritis, are thought to have a complex genetic basis. However, the genetic component of PsA has been difficult to assess for several reasons. There is strong evidence for a genetic predisposition to psoriasis alone that may mask the genetic factors that are important for the development of PsA. Although most would accept PsA as a distinct disease entity, at times there is a phenotypic overlap with rheumatoid arthritis and ankylosing spondylitis. Also, PsA itself is not a homogeneous condition and various subgroups have been proposed.

Increased amounts of TNF-$\alpha$ have been reported in both psoriatic skin (Ettehadi, et al. (1994) *Clin. Exp. Immunol.* 96(1):146-151) and synovial fluid (Partsch, et al. (1997) *J. Rheumatol.* 4(3):518-23). Recent trials have shown a positive benefit of anti-TNF treatment in both PsA (Mease, et al. (2000) *Lancet* 356:385-390) and ankylosing spondylitis (Brandt, et al. (2000) *Arthritis Rheum.* 43:1346-1352).

Reactive Arthritis. The compounds and methods of this invention may be used for treating patients with reactive arthritis. In reactive arthritis (ReA) the mechanism of joint damage is unclear, but it is likely that cytokines play critical roles. A more prevalent Th1 profile high levels of interferon gamma (IFN-$\gamma$) and low levels of interleukin 4 (IL-4) has been reported (Lahesmaa, et al. (1992) *J. Immunol.* 148:3079-3085; Schlaak, et al. (1992) *Eur. J. Immunol.* 22:2771-2776; Simon, et al. (1993) *Clin. Exp. Immunol.* 94:122-126; Schlaak, et al. (1996) *Clin. Exp. Rheumatol.* 14:155-162; Kotake, et al. (1999) *Infect. Immun.* 67:2682-2686; Ribbens, et al. (2000) *Eur. Cytokine Netw.* 11:669-676), but several studies have shown relative predominance of IL-4 and IL-10 and relative lack of IFN-$\gamma$ and tumor necrosis factor alpha (TNF-$\alpha$) in the synovial membrane (Simon, et al. (1994) *Proc. Natl. Acad. Sci. USA* 91:8562-85666; Yin, et al. (1999) *Rheumatology* 38:1058-1067) and fluid (SF) (Yin, et al. (1999) supra; Yin, et al. (1997) *Arthritis Rheum.* 40:1788-1797) of reactive arthritis patients compared with rheumatoid arthritis (RA) patients. A lower level of TNF-$\alpha$ secretion in reactive arthritis than in RA patients has also been reported after ex vivo stimulation of peripheral blood mononuclear cells (PBMC) (Braun, et al. (1999) *Arthritis Rheum.* 42:2039-2044).

It has been argued that clearance of reactive arthritis-associated bacteria requires the production of appropriate levels of IFN-$\gamma$ and TNF-$\alpha$, while IL-10 acts by suppressing these responses (Autenrieth, et al. (1994) *Infect. Immun.* 62:2590-2599; Sieper & Braun (1995) *Arthritis Rheum.* 38:1547-1554). IL-10 is a regulatory cytokine that inhibits the synthesis of IL-12 and TNF-$\gamma$ by activated macrophages (de Waal, et al. (1991) *J. Exp. Med.* 174:1209-1220; Hart, et al. (1995) *Immunology* 84:536-542; Chomarat, et al. (1995) *Arthritis Rheum.* 38:1046-1054) and of IFN-$\gamma$ by T cells (Macatonia, et al. (1993) *J. Immunol.* 150:3755-3765).

Enteropathic Arthritis. The compounds and methods of this invention may be used for treating patients with enteropathic arthritis. Typically enteropathic arthritis (EA) occurs in combination with inflammatory bowel diseases (IBD) such as Crohn's disease or ulcerative colitis. It also can affect the spine and sacroiliac joints. Enteropathic arthritis involves the peripheral joints, usually in the lower extremities such as the knees or ankles. It commonly involves only a few or a limited number of joints and may closely follow the bowel condition. This occurs in approximately 11% of patients with ulcerative colitis and 21% of those with Crohn's disease. The synovitis is generally self-limited and non-deforming.

Enteropathic arthropathies include a collection of rheumatologic conditions that share a link to GI pathology. These conditions include reactive (i.e., infection-related) arthritis due to bacteria (e.g., *Shigella, Salmonella, Campylobacter, Yersinia* species, *Clostridium difficile*), parasites (e.g., *Strongyloides stercoralis, Taenia saginata, Giardia lamblia, Ascaris lumbricoides, Cryptosporidium* species), and spondyloarthropathies associated with inflammatory bowel disease (IBD). Other conditions and disorders include intestinal bypass (jejunoileal), arthritis, celiac disease, Whipple disease, and collagenous colitis.

Juvenile Rheumatoid Arthritis. The compounds and methods of this invention may be used for treating patients with JRA. Juvenile rheumatoid arthritis (JRA), a term for the most prevalent form of arthritis in children, is applied to a family of illnesses characterized by chronic inflammation and hypertrophy of the synovial membranes. The term overlaps, but is not completely synonymous, with the family of illnesses referred to as juvenile chronic arthritis and/or juvenile idiopathic arthritis in Europe.

Both innate and adaptive immune systems use multiple cell types, a vast array of cell surface and secreted proteins, and interconnected networks of positive and negative feedback (Lo, et al. (1999) *Curr. Dir. Autoimmun.* 1:226-246). Furthermore, while separable in thought, the innate and adaptive wings of the immune system are functionally intersected (Fearon & Locksley (1996) *Science* 272(5258):50-53), and pathologic events occurring at these intersecting points are likely to be highly relevant to our understanding of pathogenesis of adult and childhood forms of chronic arthritis (Warrington, et al. (2001) *Arthritis and Rheumatism* 44:13-20).

Polyarticular JRA is a distinct clinical subtype characterized by inflammation and synovial proliferation in multiple joints (four or more), including the small joints of the hands (Jarvis (2002) *Pediatr. Ann.* 31(7):437-446). This subtype of JRA may be severe, because of both its multiple joint involvement and its capacity to progress rapidly over time. Although clinically distinct, polyarticular JRA is not homogeneous, and patients vary in disease manifestations, age of onset, prognosis, and therapeutic response. These differences very likely reflect a spectrum of variation in the nature of the immune and inflammatory attack that can occur in this disease (Jarvis (1998) *Curr. Opin. Rheumatol.* 10(5):459-467).

Early Inflammatory Arthritis. The compounds and methods of this invention may also be used for treating patients with early inflammatory arthritis. The clinical presentation of different inflammatory arthropathies is similar early in the course of disease. As a result, it is often difficult to distinguish patients who are at risk of developing the severe and persistent synovitis that leads to erosive joint damage from those whose arthritis is more self-limited.

Recent efforts to identify predictors of poor outcome in early inflammatory arthritis have identified the presence of RA specific autoantibodies, in particular antibodies towards citrullinated peptides, to be associated with erosive and persistent disease in early inflammatory arthritis cohorts. On the basis of this, a cyclical citrullinated peptide (CCP) has been developed to assist in the identification of anti-CCP antibodies in patient sera. Using this approach, the presence of anti-CCP antibodies has been shown to be specific and sensitive for RA, can distinguish RA from other arthropathies, and can potentially predict persistent, erosive synovitis before these outcomes become clinically manifest (Schellekens, et al. (2000) *Arthritis Rheum.* 43(1):155-163). Importantly, anti-CCP antibodies are often detectable in sera many years prior to clinical symptoms suggesting that they may be reflective of subclinical immune events (Nielen, et al. (2004) *Arthritis Rheum.* 50(2):380-386; Rantapaa-Dahlqvist, et al. (2003) *Arthritis Rheum.* 48(10):2741-2749).

The clinical presentation of different inflammatory arthropathies is similar early in the course of disease. As a result, it is often difficult to distinguish patients who are at risk of developing the severe and persistent synovitis that leads to erosive joint damage from those whose arthritis is more self-limited. Such distinction is critical in order to target therapy appropriately, treating aggressively those with erosive disease and avoiding unnecessary toxicity in patients with more self-limited disease. Current clinical criteria for diagnosing erosive arthropathies such as rheumatoid arthritis (RA) are less effective in early disease and traditional markers of disease activity such as joint counts and acute phase response do not adequately identify patients likely to have poor outcomes (Harrison, et al. (1998) *J. Rheumatol.* 25(12):2324-2330). Parameters reflective of the pathologic events occurring in the synovium are most likely to be of significant prognostic value.

Recent efforts to identify predictors of poor outcome in early inflammatory arthritis have identified the presence of RA specific autoantibodies, in particular antibodies towards citrullinated peptides, to be associated with erosive and persistent disease in early inflammatory arthritis cohorts. On the basis of this, a cyclical citrullinated peptide (CCP) has been developed to assist in the identification of anti-CCP antibodies in patient sera. Using this approach, the presence of anti-CCP antibodies has been shown to be specific and sensitive for RA, can distinguish RA from other arthropathies, and can potentially predict persistent, erosive synovitis before these outcomes become clinically manifest. Importantly, anti-CCP antibodies are often detectable in sera many years prior to clinical symptoms suggesting that they may be reflective of subclinical immune events (Nielen, et al. (2004) supra; Rantapaa-Dahlqvist, et al. (2003) supra).

Ankylosing Spondylitis. The compounds and methods of this invention may be used for treating patients with ankylosing spondylitis. AS is a disease subset within a broader disease classification of spondyloarthropathy. Patients affected with the various subsets of spondyloarthropathy have disease etiologies that are often very different, ranging from bacterial infections to inheritance. Yet, in all subgroups, the end result of the disease process is axial arthritis. Despite the early clinically differences seen in the various patient populations, many of them end up nearly identical after a disease course of ten-to-twenty years. Recent studies suggest the mean time to clinical diagnosis of ankylosing spondylitis from disease onset of disease is 7.5 years (Khan (1998) *J. Neurochem.* 71:78-87). These same studies suggest that the spondyloarthropathies may have prevalence close to that of rheumatoid arthritis (Feldtkeller, et al. (2003) *Rheumatol. Int.* 23(2):61-66; Doran, et al. (2003) *J. Rheumatol.* 30(2):316-320).

AS is a chronic systemic inflammatory rheumatic disorder of the axial skeleton with or without extraskeletal manifestations. Sacroiliac joints and the spine are primarily affected, but hip and shoulder joints, and less commonly peripheral joints or certain extra-articular structures such as the eye, vasculature, nervous system, and gastrointestinal system may also be involved. Its etiology is not yet fully understood (Wordsworth (1995) In: *Genes and Arthritis* Brit. Medical Bulletin 51:249-266; Calin & Taurog (1998) In: *The Spondylarthritides* Calin et al. (Eds.) Oxford UK. Oxford University Press 179). It is strongly associated with the major histocompatibility class I (MHC I) HLA-B27 allele (Calin & Taurog (1998) supra). AS affects individuals in the prime of their life and is feared because of its potential to cause chronic pain and irreversible damage of tendons, ligaments, joints, and bones (Brewerton, et al. (1973) *Lancet.* 1:904-907; Brewerton, et al. (1973) *Lancet.* 1:956-957; Schlosstein, et al. (1973) *NE J. Medicine* 288:704-706). AS may occur alone or in association with another form of spondyloarthropathy such as reactive arthritis, psoriasis, psoriatic arthritis, enthesitis, ulcerative colitis, irritable bowel disease, or Crohn's disease, in which case it is classified as secondary AS.

Typically, the affected sites include the discovertebral, apophyseal, costovertebral, and costotransverse joints of the spine, and the paravertebral ligamentous structures. Inflammation of the entheses, which are sites of musculotendinous and ligamentous attachment to bones, is also prominent in this disease (Calin & Taurog (1998) supra). The site of enthesitis is known to be infiltrated by plasma cells, lymphocytes, and polymorphonuclear cells. The inflammatory process frequently results in gradual fibrous and bony ankylosis, (Ball (1971) *Ann. Rheum. Dis.* 30:213-223; Khan (1990) *Toxicol. Applied Pharmacol.* 103:482-490).

Delayed diagnosis is common because symptoms are often attributed to more common back problems. A dramatic loss of flexibility in the lumbar spine is an early sign of AS. Other common symptoms include chronic pain and stiffness in the lower back which usually starts where the lower spine is joined to the pelvis, or hip. Although most symptoms begin in the lumbar and sacroiliac areas, they may involve the neck and upper back as well. Arthritis may also occur in the shoulder, hips and feet. Some patients have eye inflammation, and more severe cases must be observed for heart valve involvement.

The most frequent presentation is back pain, but disease can begin atypically in peripheral joints, especially in children and women, and rarely with acute iritis (anterior uveitis). Additional early symptoms and signs are diminished chest expansion from diffuse costovertebral involvement, low-grade fever, fatigue, anorexia, weight loss, and anemia. Recurrent back pain—often nocturnal and of varying intensity—is an eventual complaint, as is morning stiffness typically relieved by activity. A flexed or bent-over posture eases back pain and paraspinal muscle spasm; thus, some degree of kyphosis is common in untreated patients.

Systemic manifestations occur in ⅓ of patients. Recurrent, usually self-limited, acute iritis (anterior uveitis) rarely is protracted and severe enough to impair vision. Neurologic signs can occasionally result from compression radiculitis or sciatica, vertebral fracture or subluxation, and cauda equina syndrome (which consists of impotence, nocturnal urinary incontinence, diminished bladder and rectal sensation, and absence of ankle jerks). Cardiovascular manifestations can include aortic insufficiency, angina, pericarditis, and ECG conduction abnormalities. A rare pulmonary finding is upper lobe fibrosis, occasionally with cavitation that may be mistaken for TB and can be complicated by infection with *Aspergillus*.

AS is characterized by mild or moderate flares of active spondylitis alternating with periods of almost or totally inactive inflammation. Proper treatment in most patients results in minimal or no disability and in full, productive lives despite back stiffness. Occasionally, the course is severe and progressive, resulting in pronounced incapacitating deformities. The prognosis is bleak for patients with refractory iritis and for the rare patient with secondary amyloidosis.

Ulcerative Colitis. The compounds and methods of this invention may be used for treating patients with ulcerative colitis. Ulcerative colitis is a disease that causes inflammation and sores, called ulcers, in the lining of the large intestine. The inflammation usually occurs in the rectum and lower part of the colon, but it may affect the entire colon. Ulcerative colitis rarely affects the small intestine except for the end section, called the terminal ileum. Ulcerative colitis may also be called colitis or proctitis. The inflammation makes the colon empty frequently, causing diarrhea. Ulcers form in places where the inflammation has killed the cells lining the colon; the ulcers bleed and produce pus.

Ulcerative colitis is an inflammatory bowel disease (IBD), the general name for diseases that cause inflammation in the small intestine and colon. Ulcerative colitis can be difficult to diagnose because its symptoms are similar to other intestinal disorders and to another type of IBD, Crohn's disease. Crohn's disease differs from ulcerative colitis because it causes inflammation deeper within the intestinal wall. Also, Crohn's disease usually occurs in the small intestine, although it can also occur in the mouth, esophagus, stomach, duodenum, large intestine, appendix, and anus.

Ulcerative colitis may occur in people of any age, but most often it starts between ages 15 and 30, or less frequently between ages 50 and 70. Children and adolescents sometimes develop the disease. Ulcerative colitis affects men and women equally and appears to run in some families. Theories about what causes ulcerative colitis abound, but none have been proven. The most popular theory is that the body's immune system reacts to a virus or a bacterium by causing ongoing inflammation in the intestinal wall. People with ulcerative colitis have abnormalities of the immune system, but doctors do not know whether these abnormalities are a cause or a result of the disease. Ulcerative colitis is not caused by emotional distress or sensitivity to certain foods or food products, but these factors may trigger symptoms in some people.

The most common symptoms of ulcerative colitis are abdominal pain and bloody diarrhea. Patients also may experience fatigue, weight loss, loss of appetite, rectal bleeding, and loss of body fluids and nutrients. About half of patients have mild symptoms. Others suffer frequent fever, bloody diarrhea, nausea, and severe abdominal cramps. Ulcerative colitis may also cause problems such as arthritis, inflammation of the eye, liver disease (hepatitis, cirrhosis, and primary sclerosing cholangitis), osteoporosis, skin rashes, and anemia. No one knows for sure why problems occur outside the colon. Scientists think these complications may occur when the immune system triggers inflammation in other parts of the body. Some of these problems go away when the colitis is treated.

A thorough physical exam and a series of tests may be required to diagnose ulcerative colitis. Blood tests may be done to check for anemia, which could indicate bleeding in the colon or rectum. Blood tests may also uncover a high white blood cell count, which is a sign of inflammation somewhere in the body. By testing a stool sample, the doctor can detect bleeding or infection in the colon or rectum. The doctor may do a colonoscopy or sigmoidoscopy. For either test, the doctor inserts an endoscope—a long, flexible, lighted tube connected to a computer and TV monitor—into the anus to see the inside of the colon and rectum. The doctor will be able to see any inflammation, bleeding, or ulcers on the colon wall. During the exam, the doctor may do a biopsy, which involves taking a sample of tissue from the lining of the colon to view with a microscope. A barium enema x ray of the colon may also be required. This procedure involves filling the colon with barium, a chalky white solution. The barium shows up white on x-ray film, allowing the doctor a clear view of the colon, including any ulcers or other abnormalities that might be there.

Treatment for ulcerative colitis depends on the seriousness of the disease. Most people are treated with medication. In severe cases, a patient may need surgery to remove the diseased colon. Surgery is the only cure for ulcerative colitis. Some people whose symptoms are triggered by certain foods are able to control the symptoms by avoiding foods that upset their intestines, like highly seasoned foods, raw fruits and vegetables, or milk sugar (lactose). Each person may experience ulcerative colitis differently, so treatment is adjusted for each individual. Emotional and psychological support is important. Some people have remissions—periods when the symptoms go away—that last for months or even years. However, most patients' symptoms eventually return. This changing pattern of the disease means one cannot always tell when a treatment has helped. Some people with ulcerative colitis may need medical care for some time, with regular doctor visits to monitor the condition.

Crohn's Disease. The compounds and methods of this invention may be used for treating patients with Crohn's disease. Another disorder for which immunosuppression has been tried is Crohn's disease. Crohn's disease symptoms include intestinal inflammation and the development of intestinal stenosis and fistulas; neuropathy often accompanies these symptoms. Anti-inflammatory drugs, such as 5-aminosalicylates (e.g., mesalamine) or corticosteroids, are typically prescribed, but are not always effective (reviewed in Botoman, et al. (1998) *Am. Fam. Physician* 57(1):57-68). Immunosuppression with cyclosporine is sometimes beneficial for patients resistant to or intolerant of corticosteroids (Brynskov, et al. (1989) *N. Engl. J. Med.* 321(13):845-850).

Efforts to develop diagnostic and treatment tools against Crohn's disease have focused on the central role of cytokines (Schreiber (1998) *Neth. J. Med.* 53(6):S24-31; van Hogezand & Verspaget (1998) *Drugs* 56(3):299-305). Cytokines are small secreted proteins or factors (5 to 20 kD) that have specific effects on cell-to-cell interactions, intercellular communication, or the behavior of other cells. Cytokines are produced by lymphocytes, especially $T_H1$ and $T_H2$ lymphocytes, monocytes, intestinal macrophages, granulocytes, epithelial cells, and fibroblasts (reviewed in Rogler & Andus (1998) *World J. Surg.* 22(4):382-389; Galley & Webster (1996) *Br. J. Anaesth.* 77:11-16). Some cytokines are pro-inflammatory (e.g., TNF-α, IL-1 (α and β), IL-6, IL-8, IL-12, or leukemia inhibitory factor [LIF]); others are anti-inflammatory (e.g., IL-1 receptor antagonist, IL-4, IL-10, IL-11, and TGF-β). However, there may be overlap and functional redundancy in their effects under certain inflammatory conditions.

In active cases of Crohn's disease, elevated concentrations of TNF-α and IL-6 are secreted into the blood circulation, and TNF-α, IL-1, IL-6, and IL-8 are produced in excess locally by mucosal cells (Funakoshi, et al. (1998) *Digestion* 59(1):73-78). These cytokines can have far-ranging effects on physiological systems including bone development, hematopoiesis, and liver, thyroid, and neuropsychiatric function. Also, an imbalance of the IL-1β/IL-1ra ratio, in favor of pro-inflammatory IL-1β, has been observed in patients with Crohn's disease (Rogler & Andus (1998) supra; Saiki, et al. (1998) *Scand. J. Gastroenterol.* 33(6):616-622; Dionne et al. (1998) *Clin. Exp. Immunol.* 112(3):435-442; Kuboyama (1998) *Kurume Med. J.* 45(1):33-37). One study suggested that cytokine profiles in stool samples could be a useful diagnostic tool for Crohn's disease (Saiki, et al. (1998) supra).

Treatments that have been proposed for Crohn's disease include the use of various cytokine antagonists (e.g., IL-1ra), inhibitors (e.g., of IL-1β converting enzyme and antioxidants) and anti-cytokine antibodies (Rogler & Andus (1998) supra; van Hogezand & Verspaget (1998); supra Reimund, et al. (1998) *Eur. J. Clin. Invest.* 28(2):145-150; Lugering, et al. (1998) *Ital. J. Gastroenterol. Hepatol.* 30(3):338-344; McAlindon, et al. (1998) *Gut* 42(2):214-219). In particular, monoclonal antibodies against TNF-α have been tried with some success in the treatment of Crohn's disease (Targan, et al. (1997) *N. Engl. J. Med.* 337(15):1029-1035; Stack, et al. (1997) *Lancet* 349(9051):521-524; van Dullemen, et al. (1995) *Gastroenterol.* 109(1):129-135). These compounds may be used in combination therapy with compounds of the present invention.

Another approach to the treatment of Crohn's disease has focused on at least partially eradicating the bacterial community that may be triggering the inflammatory response and replacing it with a non-pathogenic community. For example, U.S. Pat. No. 5,599,795 discloses a method for the prevention and treatment of Crohn's disease in human patients. Their method was directed to sterilizing the intestinal tract with at least one antibiotic and at least one anti-fungal agent to kill off the existing flora and replacing them with different, select, well-characterized bacteria taken from normal humans. Borody taught a method of treating Crohn's disease by at least partial removal of the existing intestinal microflora by lavage and replacement with a new bacterial community introduced by fecal inoculum from a disease-screened human donor or by a composition including *Bacteroides* and *Escherichia coli* species. (U.S. Pat. No. 5,443,826).

Systemic Lupus Erythematosus. The compounds and methods of this invention may be used for treating patients with SLE. There has also been no known cause for autoimmune diseases such as systemic lupus erythematosus. Systemic lupus erythematosus (SLE) is an autoimmune rheumatic disease characterized by deposition in tissues of autoantibodies and immune complexes leading to tissue injury (Kotzin (1996) *Cell* 85:303-306). In contrast to autoimmune diseases such as MS and type 1 diabetes mellitus, SLE potentially involves multiple organ systems directly, and its clinical manifestations are diverse and variable (reviewed by Kotzin & O'Dell (1995) In: *Samler's Immunologic Diseases* 5$^{th}$ Ed. Frank et al., (Eds.) Little Brown & Co. Boston 667-697). For example, some patients may demonstrate primarily skin rash and joint pain, show spontaneous remissions, and require little medication. At the other end of the spectrum are patients who demonstrate severe and progressive kidney involvement that requires therapy with high doses of steroids and cytotoxic drugs such as cyclophosphamide (Kotzin (1996) supra).

The serological hallmark of SLE, and the primary diagnostic test available, is elevated serum levels of IgG antibodies to constituents of the cell nucleus, such as double-stranded DNA (dsDNA), single-stranded DNA (ss-DNA), and chromatin. Among these autoantibodies, IgG anti-dsDNA antibodies play a major role in the development of lupus glomerulonephritis (GN) (Hahn & Tsao (1993) In: *Dubois' Lupus Erythematosus* 4$^{th}$ Ed Wallace and Hahn (Eds.) Lea and Febiger Philadelphia 195-201; Ohnishi, et al. (1994) *Int. Immunol.* 6:817-830). Glomerulonephritis is a serious condition in which the capillary walls of the kidney's blood purifying glomeruli become thickened by accretions on the epithelial side of glomerular basement membranes. The disease is often chronic and progressive and may lead to eventual renal failure.

Irritable Bowel Syndrome. The compounds and methods of this invention may be used for treating patients with Irritable bowel syndrome (IBS). IBS is a functional disorder characterized by abdominal pain and altered bowel habits. This syndrome may begin in young adulthood and can be associated with significant disability. This syndrome is not a homogeneous disorder. Rather, subtypes of IBS have been described on the basis of the predominant symptom—diarrhea, constipation, or pain. In the absence of "alarm" symptoms, such as fever, weight loss, and gastrointestinal bleeding, a limited workup is needed. Once a diagnosis of IBS is made, an integrated treatment approach can effectively reduce the severity of symptoms. IBS is a common disorder, although its prevalence rates have varied. In general, IBS affects about 15% of US adults and occurs about three times more often in women than in men (Jailwala, et al. (2000) *Ann. Intern. Med.* 133(2):136-147).

IBS accounts for between 2.4 million and 3.5 million visits to physicians each year. It not only is the most common condition seen by gastroenterologists but also is one of the most common gastrointestinal conditions seen by primary care physicians (Everhart, et al. (1991) *Gastroenterol.* 100 (4):998-1005; Sandler (1990) *Gastroenterol.* 99(2):409-415).

IBS is also a costly disorder. Compared with persons who do not have bowel symptoms, persons with IBS miss three times as many workdays and are more likely to report being too sick to work (Drossman, et al. (1993) *Dig. Dis. Sci.* 38(9):1569-1580; Drossman, et al. (1997) *Gastroenterol.* 112 (6):2120-2137). Moreover, those with IBS incur hundreds of dollars more in medical charges than persons without bowel disorders (Talley, et al. (1995) *Gastroenterol.* 109(6):1736-1741).

No specific abnormality accounts for the exacerbations and remissions of abdominal pain and altered bowel habits experienced by patients with IBS. The evolving theory of IBS suggests dysregulation at multiple levels of the brain-gut axis. Dysmotility, visceral hypersensitivity, abnormal modulation of the central nervous system (CNS), and infection have all been implicated. In addition, psychosocial factors play an important modifying role. Abnormal intestinal motility has long been considered a factor in the pathogenesis of IBS. Transit time through the small intestine after a meal has been shown to be shorter in patients with diarrhea-predominant IBS than in patients who have the constipation-predominant or pain-predominant subtype (Cann, et al. (1983) *Gut.* 24(12): 1135-1140).

In studies of the small intestine during fasting, the presence of both discrete, clustered contractions and prolonged, propagated contractions has been reported in patients with IBS (Kellow & Phillips (1987) *Gastroenterol.* 92(6):1885-1893). They also experience pain with irregular contractions more often than healthy persons (Kellow & Phillips (1987) supra; Horwitz & Fisher (2001) *N. Engl. J. Med.* 344(24):1846-1850)

These motility findings do not account for the entire symptom complex in patients with IBS; in fact, most of these patients do not have demonstrable abnormalities (Rothstein (2000) *Med. Clin. North Am.* 84(5):1247-1257). Patients with IBS have increased sensitivity to visceral pain. Studies involving balloon distention of the rectosigmoid colon have shown that patients with IBS experience pain and bloating at pressures and volumes much lower than control subjects (Whitehead, et al. (1990) *Gastroenterol.* 98(5 Pt 1):1187-1192). These patients maintain normal perception of somatic stimuli.

Multiple theories have been proposed to explain this phenomenon. For example, receptors in the viscera may have increased sensitivity in response to distention or intraluminal contents. Neurons in the dorsal horn of the spinal cord may have increased excitability. In addition, alteration in CNS processing of sensations may be involved (Drossman, et al. (1997) supra). Functional magnetic resonance imaging studies have recently shown that compared with control subjects, patients with IBS have increased activation of the anterior cingulate cortex, an important pain center, in response to a painful rectal stimulus (Mertz, et al. (2000) *Gastroenterol.* 118(5):842-848).

Increasingly, evidence suggests a relationship between infectious enteritis and subsequent development of IBS. Inflammatory cytokines may play a role. In a survey of patients with a history of confirmed bacterial gastroenteritis (Neal, et al. (1997) *BMJ* 314(7083):779-782), 25% reported persistent alteration of bowel habits. Persistence of symptoms may be due to psychologic stress at the time of acute infection (Gwee, et al. (1999) *Gut.* 44(3):400-406).

Recent data suggest that bacterial overgrowth in the small intestine may have a role in IBS symptoms. In one study (Pimentel, et al. (2000) *Am. J. Gastroenterol.* 95(12):3503-3506), 157 (78%) of 202 IBS patients referred for hydrogen breath testing had test findings that were positive for bacterial overgrowth. Of the 47 subjects who had follow-up testing, 25 (53%) reported improvement in symptoms (i.e., abdominal pain and diarrhea) with antibiotic treatment.

IBS may present with a range of symptoms. However, abdominal pain and altered bowel habits remain the primary features. Abdominal discomfort is often described as crampy in nature and located in the left lower quadrant, although the severity and location can differ greatly. Patients may report diarrhea, constipation, or alternating episodes of diarrhea and constipation. Diarrheal symptoms are typically described as small-volume, loose stools, and stool is sometimes accompanied by mucus discharge. Patients also may report bloating, fecal urgency, incomplete evacuation, and abdominal distention. Upper gastrointestinal symptoms, such as gastroesophageal reflux, dyspepsia, or nausea, may also be present (Lynn & Friedman (1993) *N. Engl. J. Med.* 329(26):1940-1945).

Persistence of symptoms is not an indication for further testing; it is a characteristic of IBS and is itself an expected symptom of the syndrome. More extensive diagnostic evaluation is indicated in patients whose symptoms are worsening or changing. Indications for further testing also include presence of alarm symptoms, onset of symptoms after age 50, and a family history of colon cancer. Tests may include colonoscopy, computed tomography of the abdomen and pelvis, and barium studies of the small or large intestine.

Sjögren's Syndrome. The compounds and methods of this invention may be used for treating patients with Sjögren's syndrome (SS). Primary SS is a chronic, slowly progressive, systemic autoimmune disease, which affects predominantly middle-aged women (female-to-male ratio 9:1), although it can be seen in all ages including childhood (Jonsson, et al. (2002) *Oral Dis.* 8(3):130-140). It is characterized by lymphocytic infiltration and destruction of the exocrine glands, which are infiltrated by mononuclear cells including CD4+, CD8+ lymphocytes and B-cells (Jonsson, et al. (2002) supra). In addition, extraglandular (systemic) manifestations are seen in one-third of patients (Jonsson, et al. (2001) *Trends Immunol.* 22(12):653-654).

The glandular lymphocytic infiltration is a progressive feature (Jonsson, et al. (1993) *Br. J. Rheumatol.* 32(7):578-581), which, when extensive, may replace large portions of the organs. Interestingly, the glandular infiltrates in some patients closely resemble ectopic lymphoid microstructures in the salivary glands (denoted as ectopic germinal centers) (Salomonsson, et al. (2002) *Scand. J. Immunol.* 55(4):336-342; Xanthou, et al. (2001) *Arthritis Rheum.* 44(2):408-418). In SS, ectopic GCs are defined as T and B cell aggregates of proliferating cells with a network of follicular dendritic cells and activated endothelial cells. These GC-like structures formed within the target tissue also portray functional properties with production of autoantibodies (anti-Ro/SSA and anti-La/SSB) (Salomonsson & Jonsson (2003) *Arthritis Rheum.* 48(11):3187-3201).

In other systemic autoimmune diseases, such as RA, factors critical for ectopic GCs have been identified. Rheumatoid synovial tissues with GCs were shown to produce chemokines CXCL13, CCL21 and lymphotoxin (LT)-β (detected on follicular center and mantle zone B cells). Multivariate regression analysis of these analytes identified CXCL13 and LT-β as the solitary cytokines predicting GCs in rheumatoid synovitis (Weyand & Goronzy (2003) *Ann. NY Acad. Sci.* 987:140-149). Recently CXCL13 and CXCR5 in salivary glands has been shown to play an essential role in the inflammatory process by recruiting B and T cells, therefore contributing to lymphoid neogenesis and ectopic GC formation in SS (Salomonsson, et al. (2002) supra).

Psoriasis. The compounds and methods of this invention may be used for treating patients with psoriasis. Psoriasis is a chronic skin disease of scaling and inflammation that affects 2 to 2.6 percent of the United States population, or between 5.8 and 7.5 million people. Although the disease occurs in all age groups, it primarily affects adults. It appears about equally in males and females. Psoriasis occurs when skin cells quickly rise from their origin below the surface of the skin and pile up on the surface before they have a chance to mature. Usually this movement (also called turnover) takes about a month, but in psoriasis it may occur in only a few days. In its typical form, psoriasis results in patches of thick, red (inflamed) skin covered with silvery scales. These patches, which are sometimes referred to as plaques, usually itch or feel sore. They most often occur on the elbows, knees, other parts of the legs, scalp, lower back, face, palms, and soles of the feet, but they can occur on skin anywhere on the body. The disease may also affect the fingernails, the toenails, and the soft tissues of the genitals and inside the mouth. While it is not unusual for the skin around affected joints to crack, approximately 1 million people with psoriasis experience joint inflammation that produces symptoms of arthritis. This condition is called psoriatic arthritis.

Psoriasis is a skin disorder driven by the immune system, especially involving a type of white blood cell called a T cell. Normally, T cells help protect the body against infection and disease. In the case of psoriasis, T cells are put into action by mistake and become so active that they trigger other immune responses, which lead to inflammation and to rapid turnover of skin cells. In about one-third of the cases, there is a family history of psoriasis. Researchers have studied a large number of families affected by psoriasis and identified genes linked to the disease. People with psoriasis may notice that there are times when their skin worsens, then improves. Conditions that may cause flareups include infections, stress, and changes in climate that dry the skin. Also, certain medicines, including lithium and beta-blockers, which are prescribed for high blood pressure, may trigger an outbreak or worsen the disease.

The compounds of the present invention may be administered by a variety of methods, e.g., orally or by injection (e.g. subcutaneous, intravenous, intraperitoneal, etc.). Desirably, compounds of the invention are in admixture with a pharmaceutically acceptable carrier. "Pharmaceutically acceptable" means that which is useful in preparing a pharmaceutical composition that is generally safe, non-toxic and neither biologically nor otherwise undesirable and includes that which is acceptable for veterinary use as well as human pharmaceutical use. Depending on the route of administration, the active compounds may be coated in a material to protect the compound from the action of acids and other natural conditions which may inactivate the compound. They may also be administered by continuous perfusion/infusion of a disease or wound site.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan, et al. (1984) *J. Neuroimmunol.* 7:27).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. As used herein, the term "water soluble" means that the compound dissolves in water at least to the extent of 0.010 mole/liter or is classified as soluble according to literature precedence. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

Active compounds are administered at a therapeutically effective dosage sufficient to treat a condition associated with a condition in a patient. As used herein, the term "patient" or "subject" refers to a living mammalian organism, such as a human, monkey, cow, sheep, goat, dogs, cat, mouse, rat, guinea pig, or transgenic species thereof. In certain embodiments, the patient or subject is a primate. Non-limiting examples of human subjects are adults, juveniles, infants and fetuses. The term "effective," as that term is used in the specification and/or claims, means adequate to accomplish a desired, expected, or intended result. "Therapeutically effective amount" or "pharmaceutically effective amount" means that amount which, when administered to a subject or patient for treating a disease, is sufficient to effect such treatment for the disease. A "therapeutically effective amount" preferably reduces the amount of symptoms of the condition in the infected patient by at least about 20%, more preferably by at least about 40%, even more preferably by at least about 60%, and still more preferably by at least about 80% relative to untreated subjects. For example, the efficacy of a compound can be evaluated in an animal model system that may be predictive of efficacy in treating the disease in humans, such as the model systems shown in the examples and drawings.

The actual dosage amount of a compound of the present invention or composition comprising a compound of the present invention administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day. For example, regarding treatment of diabetic patients, the unit dosage may be an amount that reduces blood glucose by at least 40% as compared to an untreated subject. In another embodiment, the unit dosage is an amount that reduces blood glucose to a level that is ±10% of the blood glucose level of a non-diabetic subject.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present invention may comprise, for example, at least about 0.1% of a compound of the present invention. In other embodiments, the compound of the present invention may comprise between about 2% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may taken orally and that the timing of which is or is not dependent upon food intake. Thus, for example, the agent can be taken every morning and/or every evening, regardless of when the subject has eaten or will eat.

In addition to being used as a monotherapy, the compounds of the present invention may also find use in combination therapies. Effective combination therapy may be achieved with a single composition or pharmacological formulation that includes both agents, or with two distinct compositions or formulations, at the same time, wherein one composition includes the betulinic acid derivative according to the methods of this invention, and the other includes the second agent(s). Alternatively, the therapy may precede or follow the other agent treatment by intervals ranging from minutes to months.

Various combinations may be employed, such as when a compound of the present invention is "A" and "B" represents a secondary agent, non-limiting examples of which include, but are not limited to, A/B/A, B/A/B, B/B/A, A/A/B, A/B/B, B/A/A, A/B/B/B, B/A/B/B, B/B/B/A, B/B/A/B, A/A/B/B, A/B/A/B, A/B/B/A, B/B/A/A, B/A/B/A, B/A/A/B, A/A/A/B, B/A/A/A, A/B/A/A, and A/A/B/A.

Administration of the compounds of the present invention to a patient will follow general protocols for the administration of pharmaceuticals, taking into account the toxicity, if any, of the drug. It is expected that the treatment cycles would be repeated as necessary.

Beta interferons may be suitable secondary agents. These are medications derived from human cytokines which help regulate the immune system. They include interferon β-1b and interferon β-1a. Betaseron has been approved by the FDA for relapsing forms of secondary progressive MS. Furthermore, the FDA has approved the use of several β-interferons as treatments for people who have experienced a single attack that suggests multiple sclerosis, and who may be at risk of future attacks and developing definite MS. For example, risk of MS may be suggested when an MRI scan of the brain shows lesions that predict a high risk of conversion to definite MS.

Glatiramer acetate is a further example of a secondary agent that may be used in a combination treatment. Glatiramer is presently used to treat relapsing remitting MS. It is made of four amino acids that are found in myelin. This drug is reported to stimulate T cells in the body's immune system to change from harmful, pro-inflammatory agents to beneficial, anti-inflammatory agents that work to reduce inflammation at lesion sites.

Another potential secondary agent is mitoxantrone, a chemotherapy drug used for many cancers. This drug is also FDA-approved for treatment of aggressive forms of relapsing remitting MS, as well as certain forms of progressive MS. It is given intravenously, typically every three months. This medication is effective, but is limited by cardiac toxicity. Novantrone has been approved by the FDA for secondary progressive, progressive-relapsing, and worsening relapsing-remitting MS.

Another potential secondary agent is natalizumab. In general, natalizumab works by blocking the attachment of immune cells to brain blood vessels, which is a necessary step for immune cells to cross into the brain, thus reducing the immune cells' inflammatory action on brain neurons. Natalizumab has been shown to significantly reduce the frequency of attacks in people with relapsing MS.

In the case of relapsing remitting MS, patients may be given intravenous corticosteroids, such as methylprednisolone, as a secondary agent, to end the attack sooner and leave fewer lasting deficits.

Other common drugs for MS that may be used in combination with the betulinic acid derivatives include immunosuppressive drugs such as azathioprine, cladribine and cyclophosphamide.

It is contemplated that other anti-inflammatory agents may be used in conjunction with the treatments of the current invention. Other COX inhibitors may be used, including arylcarboxylic acids (salicylic acid, acetylsalicylic acid, diflunisal, choline magnesium trisalicylate, salicylate, benorylate, flufenamic acid, mefenamic acid, meclofenamic acid and triflumic acid), arylalkanoic acids (diclofenac, fenclofenac, alclofenac, fentiazac, ibuprofen, flurbiprofen, ketoprofen, naproxen, fenoprofen, fenbufen, suprofen, indoprofen, tiaprofenic acid, benoxaprofen, pirprofen, tolmetin, zomepirac, clopinac, indomethacin and sulindac) and enolic acids (phenylbutazone, oxyphenbutazone, azapropazone, feprazone, piroxicam, and isoxicam. See also U.S. Pat. No. 6,025,395, which is incorporated herein by reference.

Histamine H2 receptor blocking agents may also be used in conjunction with the compounds of the current invention, including cimetidine, ranitidine, famotidine and nizatidine.

Treatment with acetylcholinesterase inhibitors such as tacrine, donepizil, metrifonate and rivastigmine for the treatment of Alzheimer's and other disease in conjunction with the compounds of the present invention is contemplated. Other acetylcholinesterase inhibitors may be developed which may be used once approved include rivastigmine and metrifonate. Acetylcholinesterase inhibitors increase the amount of neurotransmitter acetylcholine at the nerve terminal by decreasing its breakdown by the enzyme cholinesterase.

MAO-B inhibitors such as selegilene may be used in conjunction with the compounds of the current invention. Selegilene is used for Parkinson's disease and irreversibly inhibits monoamine oxidase type B (MAO-B). Monoamine oxidase is an enzyme that inactivates the monoamine neurotransmitters norepinephrine, serotonin and dopamine.

Dietary and nutritional supplements with reported benefits for treatment or prevention of Parkinson's, Alzheimer's, multiple sclerosis, amyotrophic lateral sclerosis, rheumatoid arthritis, inflammatory bowel disease, and all other diseases whose pathogenesis is believed to involve excessive production of either nitric oxide (NO) or prostaglandins, such as acetyl-L-carnitine, octacosanol, evening primrose oil, vitamin B6, tyrosine, phenylalanine, vitamin C, L-dopa, or a combination of several antioxidants may be used in conjunction with the compounds of the current invention.

For the treatment or prevention of cancer, compounds of the invention may be combined with one or more of the following: radiation, chemotherapy agents (e.g., cytotoxic agents such as anthracyclines, vincristine, vinblastin, microtubule-targeting agents such as paclitaxel and docetaxel, 5-FU and related agents, cisplatin and other platinum-containing compounds, irinotecan and topotecan, gemcitabine, temozolomide, etc.), targeted therapies (e.g., imatinib, bortezomib, bevacizumab, rituximab), or vaccine therapies designed to promote an enhanced immune response targeting cancer cells.

For the treatment or prevention of autoimmune disease, compounds of the invention may be combined with one or more of the following: corticosteroids, methotrexate, anti-TNF antibodies, other TNF-targeting protein therapies, and NSAIDs. For the treatment of prevention of cardiovascular diseases, compounds of the invention may be combined with antithrombotic therapies, anticholesterol therapies such as statins (e.g., atorvastatin), and surgical interventions such as stenting or coronary artery bypass grafting. For the treatment of osteoporosis, compounds of the invention may be combined with antiresorptive agents such as bisphosphonates or anabolic therapies such as teriparatide or parathyroid hormone. For the treatment of neuropsychiatric conditions, compounds of the invention may be combined with antidepressants (e.g., imipramine or SSRIs such as fluoxetine), antipsychotic agents (e.g., olanzapine, sertindole, risperidone), mood stabilizers (e.g., lithium, valproate semisodium), or other standard agents such as anxiolytic agents. For the treatment of neurological disorders, compounds of the invention may be combined with anticonvulsant agents (e.g., valproate semisodium, gabapentin, phenyloin, carbamazepine, and topiramate), antithrombotic agents (e.g., tissue plasminogen activator), or analgesics (e.g., opioids, sodium channel blockers, and other antinociceptive agents).

For the treatment of disorders involving oxidative stress, compounds of the present invention may be combined with tetrahydrobiopterin (BH4) or related compounds. BH4 is a cofactor for constitutive forms of nitric oxide synthase, and may be depleted by reactions with peroxynitrite. Peroxynitrite is formed by the reaction of nitric oxide and superoxide. Thus, under conditions of oxidative stress excessive levels of superoxide can deplete normal, beneficial levels of nitric oxide by converting NO to peroxynitrite. The resulting depletion of BH4 by reaction with peroxynitrite results in the "uncoupling" of nitric oxide synthases so that they form superoxide rather than NO. This adds to the oversupply of superoxide and prolongs the depletion of NO. Addition of exogenous BH4 can reverse this uncoupling phenomenon, restoring the production of NO and reducing the level of oxidative stress in tissues. This mechanism is expected to complement the actions of compounds of the invention, which reduce oxidative stress by other means, as discussed above and throughout this invention.

For the purposes of the present invention, the use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Methods and Materials

Nitric Oxide Production and Cell Viability. RAW264.7 macrophages were pre-treated with DMSO or drugs for 2 hours, and subsequently treated with recombinant mouse IFN-γ (Sigma) for 24 hours. NO concentration in media was determined using the Griess reagent system (Promega). Cell viability was determined using WST-1 reagent (Roche).

Example 2

Synthesis of TP-342

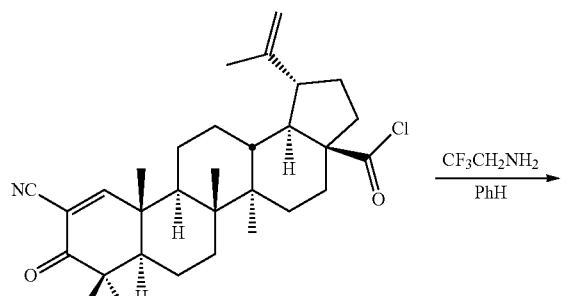

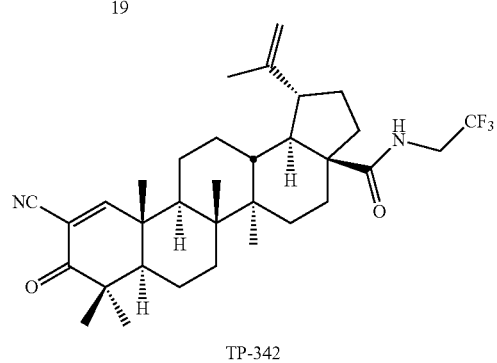

A solution of 19 (100 mg, 0.2 mmol) and 2,2,2-trifluoroethylamide (120 mg, 1.2 mmol, 6 equiv) in dry benzene (2.6 mL) was heated under reflux for 1 hour. The mixture was diluted with ethyl acetate (20 mL). The mixture was washed with saturated $NH_4Cl$ solution (three times) and brine (once), dried over $MgSO_4$, and filtered. The filtrate was concentrated in vacuo to give a residue (80 mg). The residue was purified by flash chromatography [hexanes-ethyl acetate (3:1)] to give 19 (11 mg) and TP-342 as a solid (47 mg, yield 42%, yield on consumed starting material 47%).

2-Cyano-N-(2,2,2-trifluoroethyl)-3-oxolupa-1,20(29)-dien-28-amide (TP-342): $^1$H-NMR (300 MHz, $CDCl_3$): δ 7.82 (1H, s), 5.99 (1H, t, J=6.4 Hz), 4.74 (1H, s), 4.62 (1H, s), 4.09 (1H, m), 3.74 (1H, m), 3.10 (1H, ddd, J=11.0, 11.0, and 4.4 Hz), 2.58 (1H, ddd, J=12.2, 12.2, and 3.1 Hz), 1.68, 1.18, 1.112, 1.106, 1.00, 0.98 (each 3H, s); $^{13}$C-NMR (75 MHz, $CDCl_3$): δ 198.6, 176.3, 171.3, 150.4, 128.2 (q, J=277 Hz), 115.3, 114.0, 110.0, 56.0, 52.8, 50.0, 46.6, 45.2, 44.1, 43.0, 42.1, 41.0, 40.5, 40.1, 38.2, 37.8, 33.61, 33.60, 30.7, 29.2, 27.9, 25.5, 21.6, 21.5, 19.6, 19.0, 18.6, 16.6.

Example 3

Synthesis of TP-343

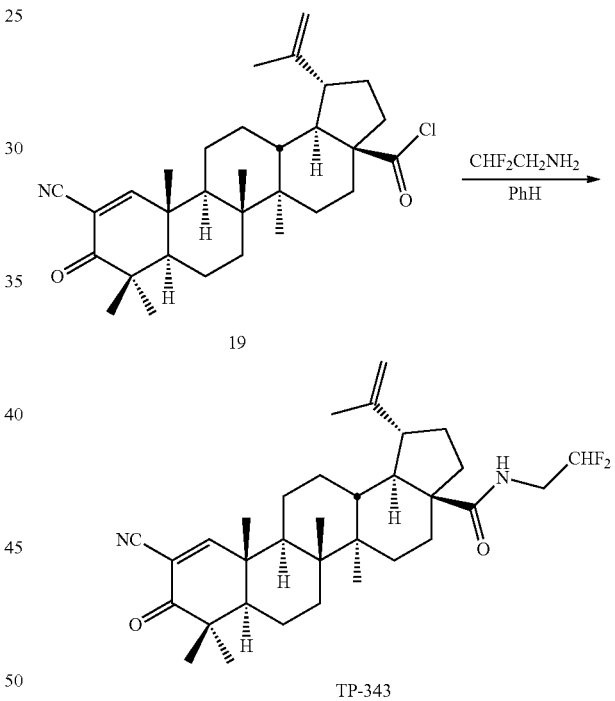

A solution of 19 (50 mg, 0.1 mmol) and 2,2-difluoroethylamide (58 mg, 0.7 mmol, 7 equiv) in dry benzene (1.0 mL) was heated under reflux for 1 hour. The mixture was diluted with ethyl acetate (10 mL). The mixture was washed with saturated $NH_4Cl$ solution (three times) and brine (once), dried over $MgSO_4$, and filtered. The filtrate was concentrated in vacuo to give a residue (47 mg). The residue was purified by flash chromatography [hexanes-ethyl acetate (2.5:1)] to give TP-343 as a solid (31 mg, yield 57%).

2-Cyano-N-(2,2-difluoroethyl)-3-oxolupa-1,20(29)-dien-28-amide (TP-343): $^1$H-NMR (300 MHz, $CDCl_3$): δ 7.82 (1H, s), 5.91 (1H, t, J=6.2 Hz), 5.86 (1H, dt, J=56.4 and 4.0 Hz), 4.75 (1H, d, J=1.5 Hz), 4.63 (1H, dd, J=1.8 and 1.1 Hz), 3.73 (1H, m), 3.55 (1H, m), 3.10 (1H, ddd, J=11.0, 11.0, and 4.4 Hz), 2.55 (1H, ddd, J=12.8, 12.8, and 3.7 Hz), 1.69, 1.18, 1.12, 1.11, 1.02, 0.98 (each 3H, s); $^{13}$C-NMR (75 MHz, CDCl$_3$): δ 198.6, 176.9, 171.2, 150.4, 115.3, 114.1, 113.8 (t, J=241 Hz), 110.1, 55.9, 52.8, 50.0, 46.7, 45.2, 44.1, 43.0, 42.1, 41.7, 41.3, 41.0, 38.3, 37.9, 33.7, 33.6, 30.8, 29.4, 27.9, 25.5, 21.6, 21.5, 19.6, 19.0, 18.6, 16.7.

Example 4

Synthesis of TP-344

Example 5

Synthesis of TP-345

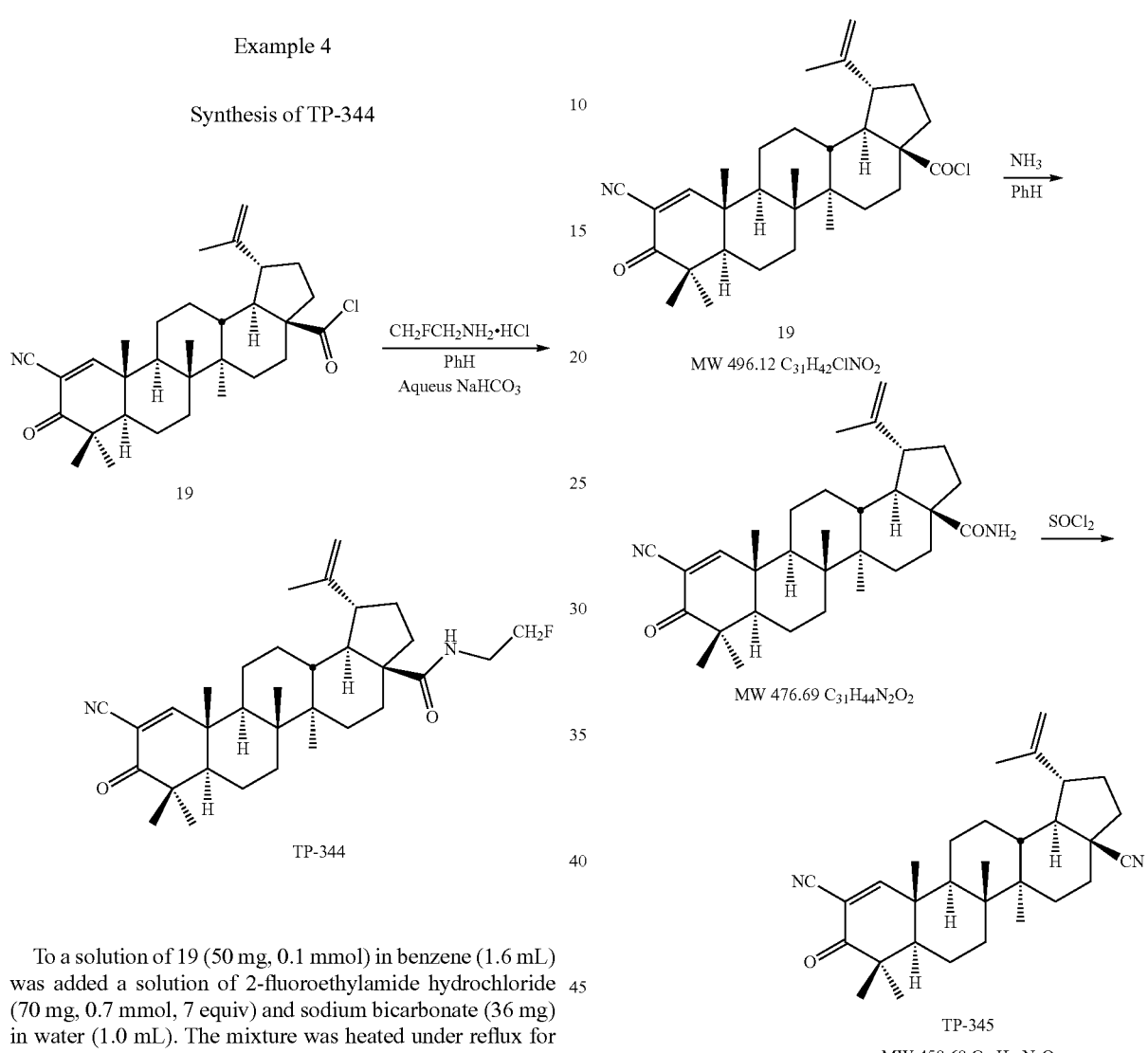

To a solution of 19 (50 mg, 0.1 mmol) in benzene (1.6 mL) was added a solution of 2-fluoroethylamide hydrochloride (70 mg, 0.7 mmol, 7 equiv) and sodium bicarbonate (36 mg) in water (1.0 mL). The mixture was heated under reflux for 1.5 hours. To the reaction mixture was added 5% aqueous HCl solution. The resultant mixture was extracted with ethyl acetate (10 mL, three times). The extract was washed with saturated sodium bicarbonate solution (twice) and brine (once), dried over MgSO$_4$, and filtered. The filtrate was concentrated in vacuo to give a residue (46 mg). The residue was purified by flash chromatography [hexanes-ethyl acetate (2:1)] to give TP-344 as a solid (31 mg, yield 59%).

2-Cyano-N-(2-fluoroethyl)-3-oxolupa-1,20(29)-dien-28-amide (TP-344): $^1$H-NMR (300 MHz, CDCl$_3$): δ 7.82 (1H, s), 5.98 (1H, t, J=5.7 Hz), 4.75 (1H, d, J=1.8 Hz), 4.62 (1H, dd, J=1.8 and 1.1 Hz), 4.57 (1H, t, J=4.4 Hz), 4.41 (1H, t, J=4.4 Hz), 3.56 (2H, m), 3.13 (1H, ddd, J=11.4, 11.4, and 4.8 Hz), 2.58 (1H, ddd, J=12.8, 12.8, and 3.7 Hz), 1.69, 1.18, 1.12, 1.11, 1.03, 0.99 (each 3H, s); $^{13}$C-NMR (75 MHz, CDCl$_3$): δ 198.6, 176.6, 171.2, 150.6, 115.3, 114.1, 110.0, 83.1 (d, J=165 Hz), 55.8, 52.8, 50.0, 46.8, 45.2, 44.2, 43.0, 42.2, 41.0, 40.1, 39.8, 38.4, 37.9, 33.8, 33.6, 30.9, 29.4, 27.9, 25.5, 21.6, 21.5, 19.6, 19.0, 18.6, 16.7.

To a solution of 19 (83 mg, 0.17 mmol) in benzene (4 mL) was bubbled ammonia gas for 50 min at room temperature. The mixture was diluted with ethyl acetate (20 mL). The mixture was washed with water (twice) and brine (twice), dried over MgSO$_4$, and filtered. The filtrate was concentrated in vacuo to give amide (known compound, Honda, et al. (2006) supra) as an amorphous solid (76 mg, yield 96%).

A solution of the amide (74.4 mg, 0.16 mmol) in thionyl chloride (1 mL) was heated under reflux for 10 minutes. The thionyl chloride was removed in vacuo to give a residue (76 mg). The residue was purified by flash chromatography [hexanes-ethyl acetate (3:1)] to afford TP-345 as a crystalline solid (28 mg, yield 40%).

2-Cyano-3-oxolupa-1,20(29)-dien-28-onitrile (TP-345): crystalline solid; $^1$H-NMR (500 MHz, CDCl$_3$): δ 7.81 (1H, s), 4.79 (1H, brs), 4.69 (1H, t, J=1.7 Hz), 2.68 (1H, ddd, J=16.6, 11.0, and 5.6 Hz), 1.69, 1.19, 1.18, 1.139, 1.135, 0.97 (each 3H, s); $^{13}$C-NMR (125 MHz, CDCl$_3$): δ 198.4, 170.7, 147.9, 123.5, 115.2, 114.2, 111.5, 52.7, 49.14, 49.06, 48.7, 45.2, 44.0, 42.8, 42.0, 41.4, 40.9, 35.9, 33.7, 31.1, 29.6, 29.1, 27.9, 24.8, 21.6, 21.3, 19.5, 19.0, 18.6, 16.7, 14.9.

Example 6

Synthesis of TP-346

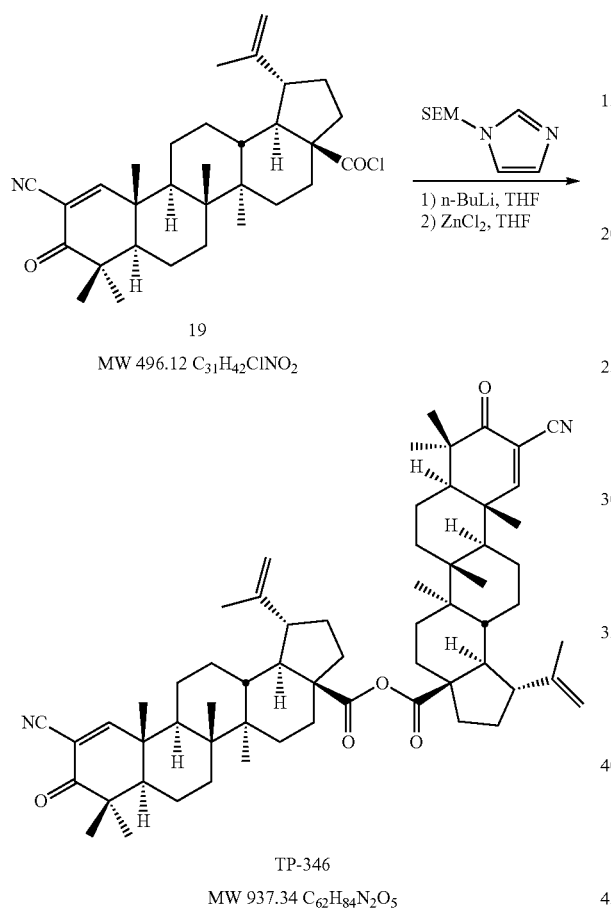

To a solution of N-SEM-imidazole (64 mg, 0.32 mmol) in anhydrous THF (2.4 mL) was added n-BuLi (2.5 M in hexanes, 150 mL, 0.375 mmol) at −78° C. (isopropanol-dry ice bath). The mixture was stirred at −78° C. for 20 minutes. To the stirred mixture was added ZnCl$_2$ (1 M in diethylether, 350 mL, 0.35 mmol) at −78° C. The stirred mixture was allowed to reach room temperature over 20 minutes. To the mixture was added a solution of 19 (80 mg, 0.16 mmol) in anhydrous THF (1.6 mL) at −78° C. The mixture was stirred at room temperature for 3 hours. The mixture was quenched by saturated aqueous NH$_4$Cl solution (2 mL). The aqueous layer was separated and then extracted with ethyl acetate (1 mL, twice). The extracts and the original organic layer were combined. The organic solution was washed with brine (twice), dried over MgSO$_4$, and filtered. The filtrate was concentrated in vacuo to give a residue (209 mg). The residue was treated with hexanes-ethyl acetate (3:1), and then the soluble (100 mg) and insoluble matter (96 mg) were separated. The soluble matter was purified by flash chromatography [hexanes-ethyl acetate (3:1)] to give 19 (amorphous solid, 11 mg), acid 4 (crystalline solid, 32 mg) and TP-346 as an amorphous solid (10 mg, yield 14%, yield on consumed starting material 31%).

2-Cyano-3-oxolupa-1,20(29)-dien-28-oic acid anhydride (TP-346): amorphous solid; $^1$H-NMR (500 MHz, CDCl$_3$): δ 7.82 (1H, s), 4.76 (1H, brs), 4.66 (1H, brs), 3.02 (1H, m), 2.37 (1H, ddd, J=12.7, 11.8, and 3.7 Hz), 2.23 (1H, m), 2.00 (2H, m), 1.85 (1H, m), 1.71, 1.19, 1.13, 1.12, 1.08, 1.00 (each 3H, s); $^{13}$C-NMR (125 MHz, CDCl$_3$): δ 198.4, 172.1, 170.9, 149.7, 115.2, 114.2, 110.6, 58.1, 52.8, 49.1, 46.7, 45.2, 44.1, 43.1, 42.2, 41.0, 38.4, 36.2, 33.6, 31.8, 30.4, 29.7, 28.0, 25.4, 21.6, 21.4, 19.5, 19.0, 18.6, 16.8, 14.7.

Example 7

Biological Activity

Certain compounds of the present invention were tested for inhibition of NO production and induction of HO-1. Compounds tested included TP-292, TP-342 (MW=558.72), TP-343 (MW=540.73), TP-344 (MW=522.74), TP-345 and TP-346.

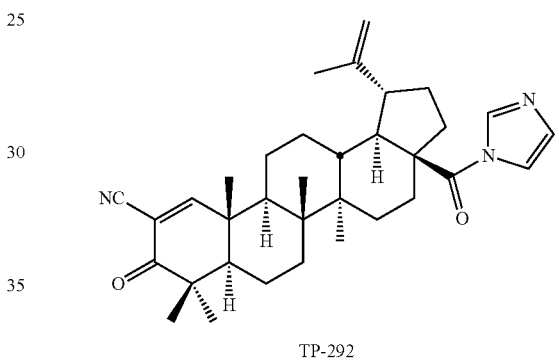

TP-292

The experimental results of NO inhibition are shown in FIG. 1 and in Table 1. The induction of HO-1 in RAW264.7 cells is also presented in Table 1. For comparative purposes, the activity of the non-fluorinated analog TP-321 (MW=504.75) is also provided. TP-321 was reported in Honda, et al. (2006) supra. The structure of TP-321 is as follows:

TABLE 1

| Working ID | MW | RAW264.7 (20 ng/mL IFNγ) NO IC$_{50}$ (nM) | HO Induction |
|---|---|---|---|
| TP-321 | | 88 | +++[2] |
| TP-292 | | 71-100 | ++[1]/+++[2] |

TP-321 structure shown above the table.

TABLE 1-continued

| TP-342 | 380 | +[2] |
| TP-343 | 130 | ++[2] |
| TP-344 | 180 | ++[2] |
| TP-345 | 10-160 | ++[1] |
| TP-346 | 2000-10000 | ±[1] |

[1] Compound at 100 nM
[2] Compound at 300 nM.

HO-1 induction assays were carried out by incubating RAW264.7 cells with the BA derivatives (100 or 300 nM) for six hours and analyzing total cell lysage by immunoblot analysis with an HO-1 antibody.

What is claimed is:

1. A compound selected from the group of:

(1R,3aS,5aR,5bR,7aR,11aR,13aR,13bR)-10-cyano-5a,5b,8,8,11a-pentamethyl-9-oxo-1-(prop-1-en-2-yl)-N-(2,2,2-trifluoroethyl)-2,3,3a,4,5,5a,5b,6,7,7a,8,9,11a,11b,12,13,13a,13b-octadecahydro-1H-cyclopenta[a]chrysene-3a-carboxamide;

TP-342

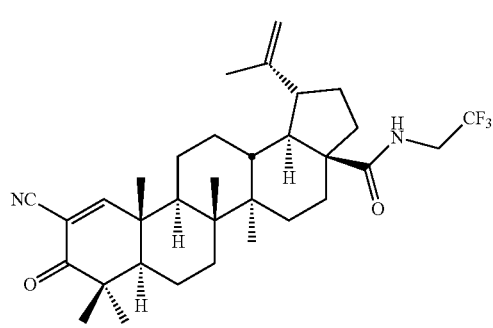

(1R,3aS,5aR,5bR,7aR,11aR,13aR,13bR)-10-cyano-N-(2,2-difluoroethyl)-5a,5b,8,8,11a-pentamethyl-9-oxo-1-(prop-1-en-2-yl)-2,3,3a,4,5,5a,5b,6,7,7a,8,9,11a,11b,12,13,13a,13b-octadecahydro-1H-cyclopenta[a]chrysene-3a-carboxamide;

TP-343

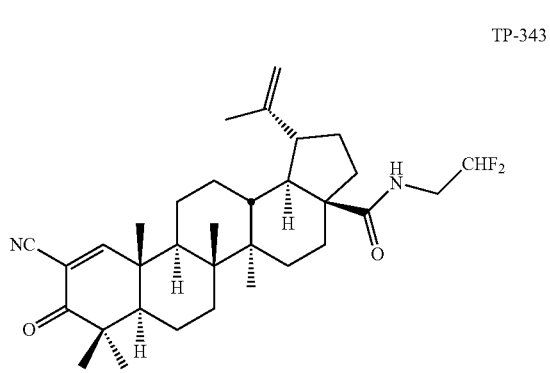

(1R,3aS,5aR,5bR,7aR,11aR,13aR,13bR)-10-cyano-N-(2-fluoroethyl)-5a,5b,8,8,11a-pentamethyl-9-oxo-1-(prop-1-en-2-yl)-2,3,3a,4,5,5a,5b,6,7,7a,8,9,11a,11b,12,13,13a,13b-octadecahydro-1H-cyclopenta[a]chrysene-3a-carboxamide;

TP-344

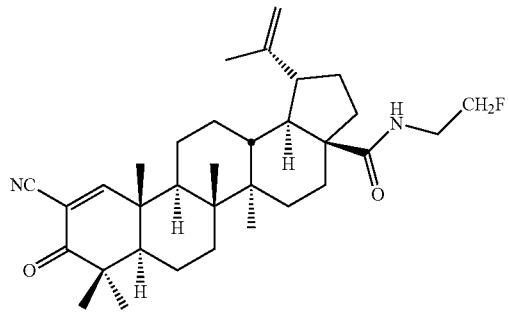

(1R,3aS,5aR,5bR,7aR,11aR,13aR,13bR)-5a,5b,8,8,11a-pentamethyl-9-oxo-1-(prop-1-en-2-yl)-2,3,3a,4,5,5a,5b,6,7,7a,8,9,11a,11b,12,13,13a,13b-octadecahydro-1H-cyclopenta[a]chrysene-3a,10-dicarbonitrile;

TP-345

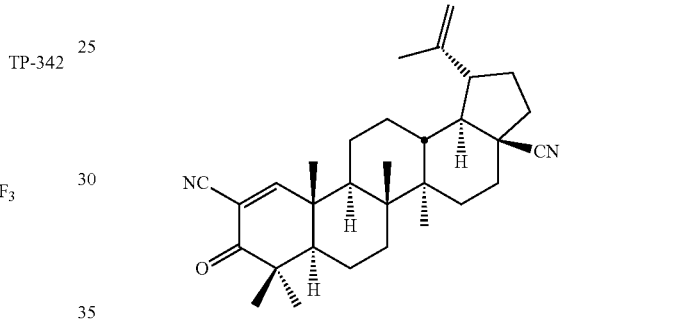

and (1R,3aS,5aR,5bR,7aR,11aR,13aR,13bR)-10-cyano-5a,5b,8,8,11a-pentamethyl-9-oxo-1-(prop-1-en-2-yl)-2,3,3a,4,5,5a,5b,6,7,7a,8,9,11a,11b,12,13,13a,13b-octadecahydro-1H-cyclopenta[a]chrysene-3a-carboxylic anhydride

TP-346

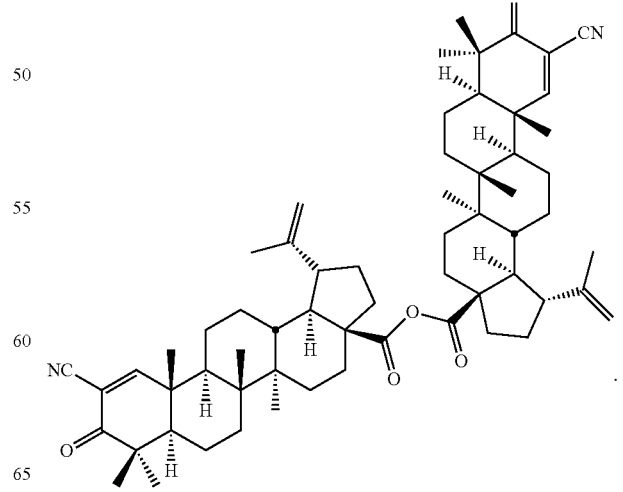

2. A pharmaceutical composition comprising as an active ingredient a compound of claim 1 and a pharmaceutically acceptable carrier.

3. A method for inhibiting IFN-γ-induced nitric oxide production in cells comprising administering to a subject in need thereof a pharmaceutically effective amount of a compound of claim 1 so that IFN-γ-induced nitric oxide production is inhibited in the cells of the subject.

4. A kit comprising a compound of claim 1; and instructions which include one or more forms of information selected from the group of indicating a disease state for which the compound is to be administered, storage information for the compound, dosing information and instructions regarding how to administer the compound.

5. The kit of claim 4, wherein the kit comprises the compound in a multiple dose form.

* * * * *